United States Patent [19]

Crosby et al.

[11] Patent Number: 4,532,930

[45] Date of Patent: Aug. 6, 1985

[54] COCHLEAR IMPLANT SYSTEM FOR AN AUDITORY PROSTHESIS

[75] Inventors: Peter A. Crosby, Drummoyne; Christopher N. Daly, Biglola Plateau; David K. Money, Pennant Hills; James F. Patrick, Lane Cove; Peter M. Seligman, Essendon; Janusz A. Kuzma, Stanmore, all of Australia

[73] Assignee: Commonwealth of Australia, Dept. of Science & Technology, Belconnan, Australia

[21] Appl. No.: 483,806

[22] Filed: Apr. 11, 1983

[51] Int. Cl.³ .............................................. A61N 1/30
[52] U.S. Cl. ................................ 128/419 R; 128/421; 179/107 E; 179/107 BC
[58] Field of Search ................... 128/419 E, 421, 422, 128/1 R, 419 R, 184, 185; 179/1, 107 E, 107 BC

[56] References Cited

U.S. PATENT DOCUMENTS

| 4,390,756 | 6/1983 | Hoffmann et al. | 128/421 X |
| 4,408,608 | 10/1983 | Daly et al. | 128/421 |

FOREIGN PATENT DOCUMENTS

| 0054418 | 6/1982 | European Pat. Off. | 128/419 R |
| 2811120 | 9/1978 | Fed. Rep. of Germany | 128/419 R |

OTHER PUBLICATIONS

Forster, J. Biomed. Eng., vol. 3, No. 2, Apr., 1981, pp. 107–120, "Theoretical Design . . . for Prosthesis Applications".
Gheewalla et al., "A CMOS . . . Auditory Stimulator for the Deaf", IEEE Jrnl. of S.S. Circs., vol. SC 10, No. 6, Dec., 1975, pp. 472–479.
Diller et al., "A Computo-Controlled Test System . . . ", Scand. Andiol. Suppl. 11, 1980, pp. 163–170.
Dovek et al., "A New Approach to the Cochlear Implant", Section of Otology, vol. 70, Jun., 1977, pp. 379–383.

Primary Examiner—Edward M. Coven
Attorney, Agent, or Firm—Alan H. MacPherson; Thomas S. MacDonald; Steven F. Caserza

[57] ABSTRACT

A cochlear implant system includes an electrode array (1) comprising multiple platinum ring electrodes in a silastic carrier to be implanted in the cochlea of the ear. A receiver-stimulator (3) containing a semiconductor integrated circuit and other components is implanted in the patient adjacent the ear to receive data information and power through tuned coil (5) using an inductive link (6) from a patient-wearable external speech processor (7) including an integrated circuit and various components which is configured or mapped to emit data signals from an EPROM programmed to suit each patient electrical stimulation perceptions through testing of the patient and his implanted stimulator/electrode using a diagnostic and programming unit (12) connected to the processor by an interface unit (10). The system allows use of various speech processing strategies including dominant spectral peak and amplitude and compression of voice pitch so as to include voiced sounds, unvoiced glottal sounds and prosodic information. Biphastic pulses are supplied to various combinations of electrodes by a switch controlled current sink in various modes of operation. In-place testing of the implant is also provided. Various safety features are incorporated to insure that harmful impulses are not imposed on the patient.

Transmission of data is by a series of discrete data bursts which represent the chosen electrode(s), the electrode mode configuration, the stimulating current, and amplitude determined by the duration of the amplitude burst.

68 Claims, 30 Drawing Figures

Cochlear Implant System - Pictorial Representation

FIG. 1 The Cochlear

FIG. 2 Cochlear Implant System Block Diagram

Cochlear Implant System – Pictorial Representation

Active Electrode Stimulus Current

Implantable Receiver/Stimulator

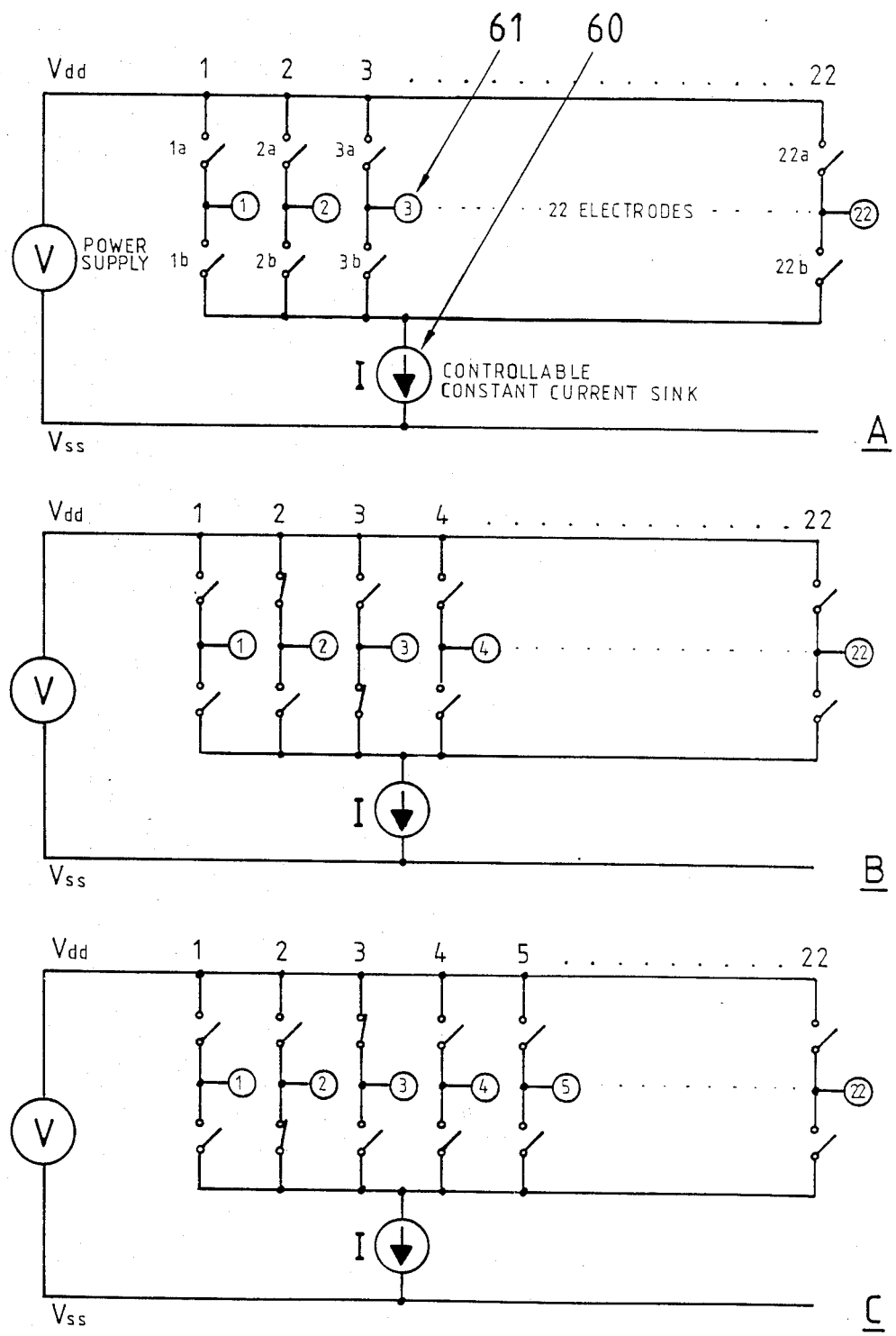
FIG.6: Stimulus Current Generation - Bipolar Mode

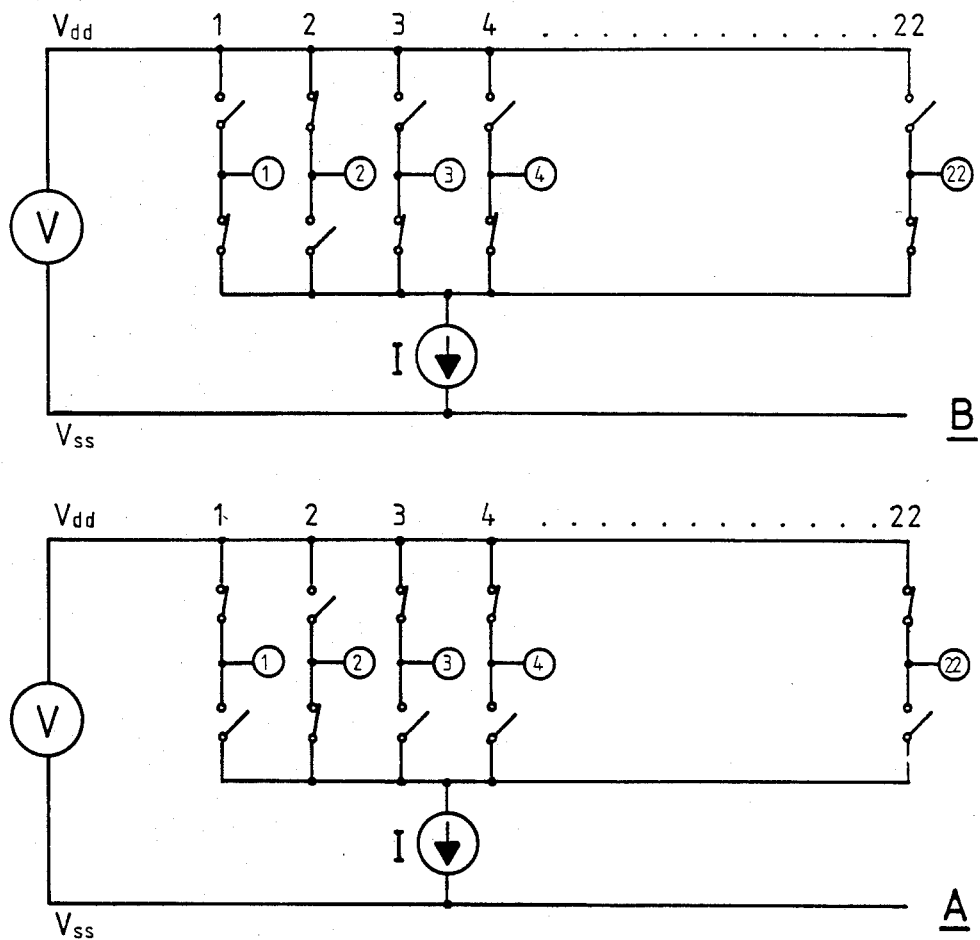
FIG. 7  Distributed Ground Stimulus Current Generation

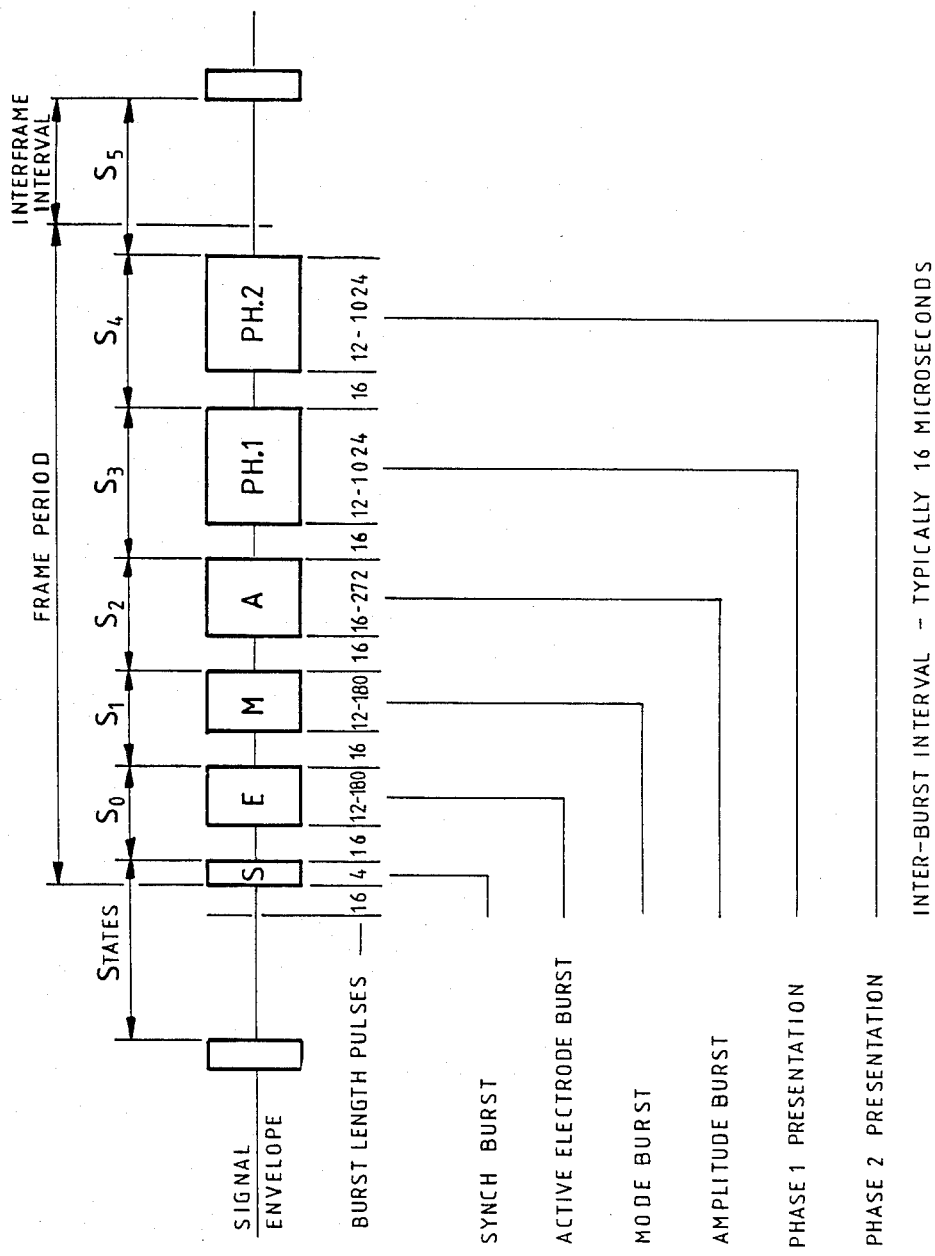
FIG. 8  POWER/DATA SIGNAL FORMAT

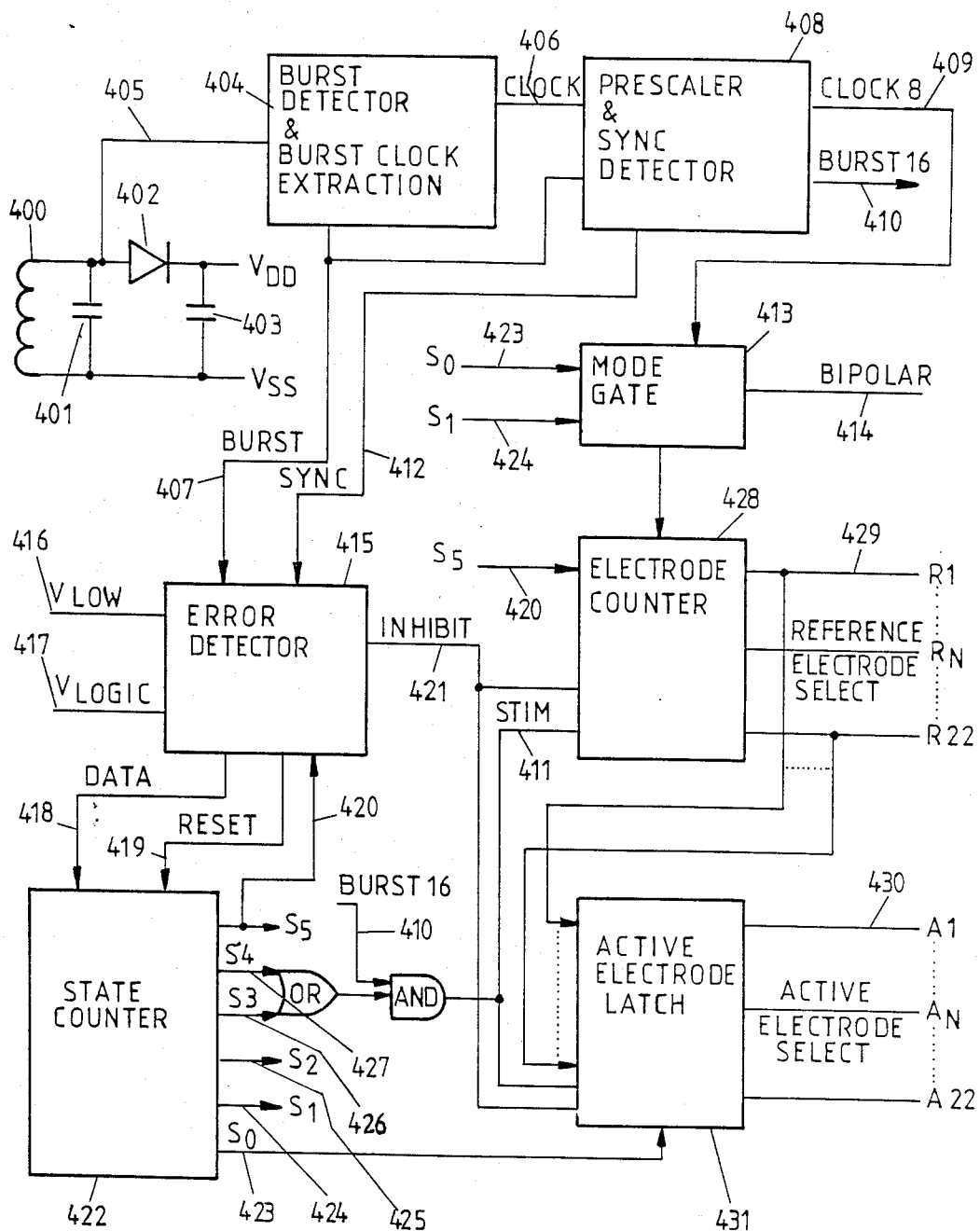
FIG. 9 Receiver Stimulator Digital Circuit. Block Diagram.

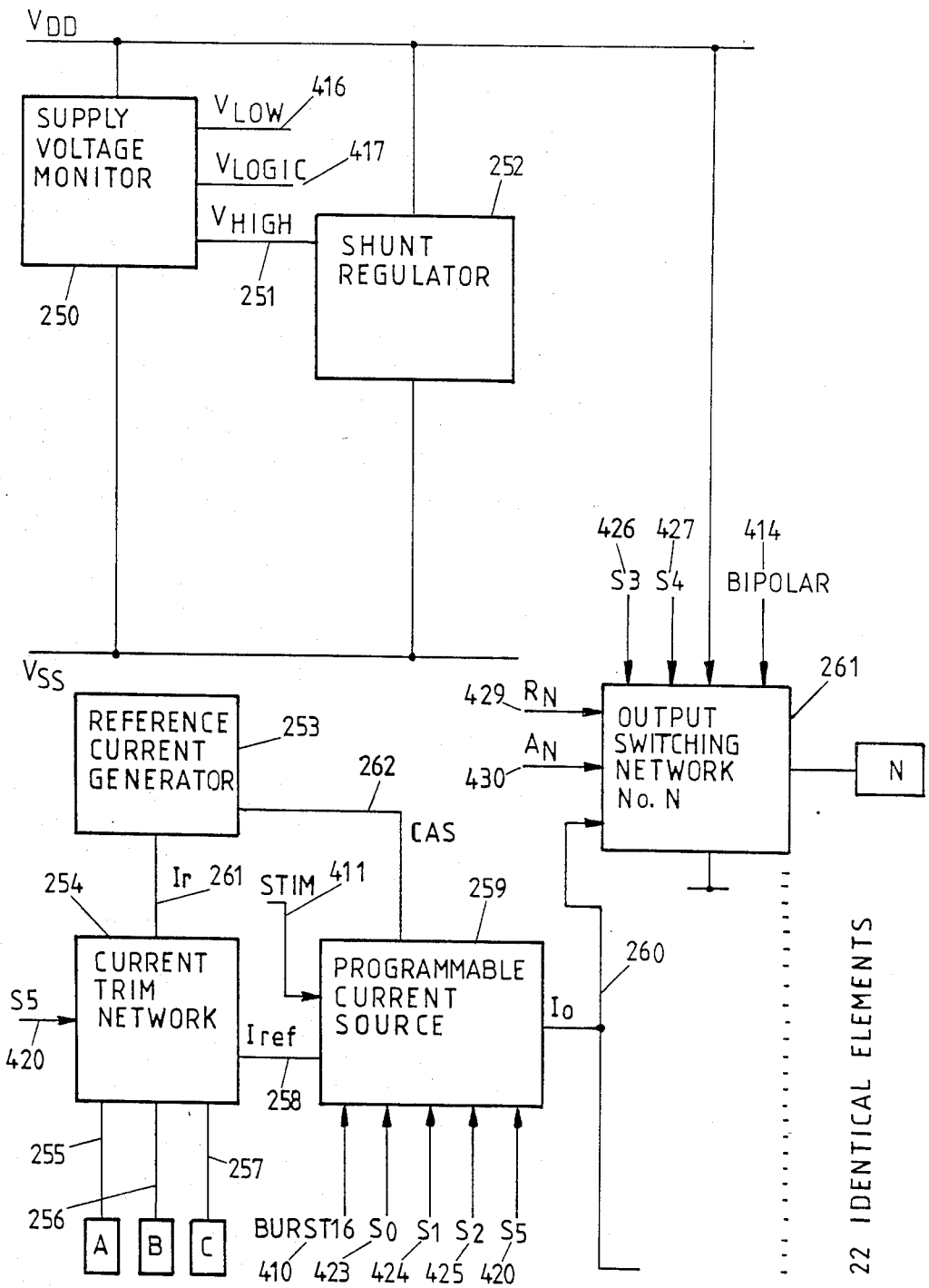
FIG.10: Receiver Stimulator Analog Circuit. Block Diagram

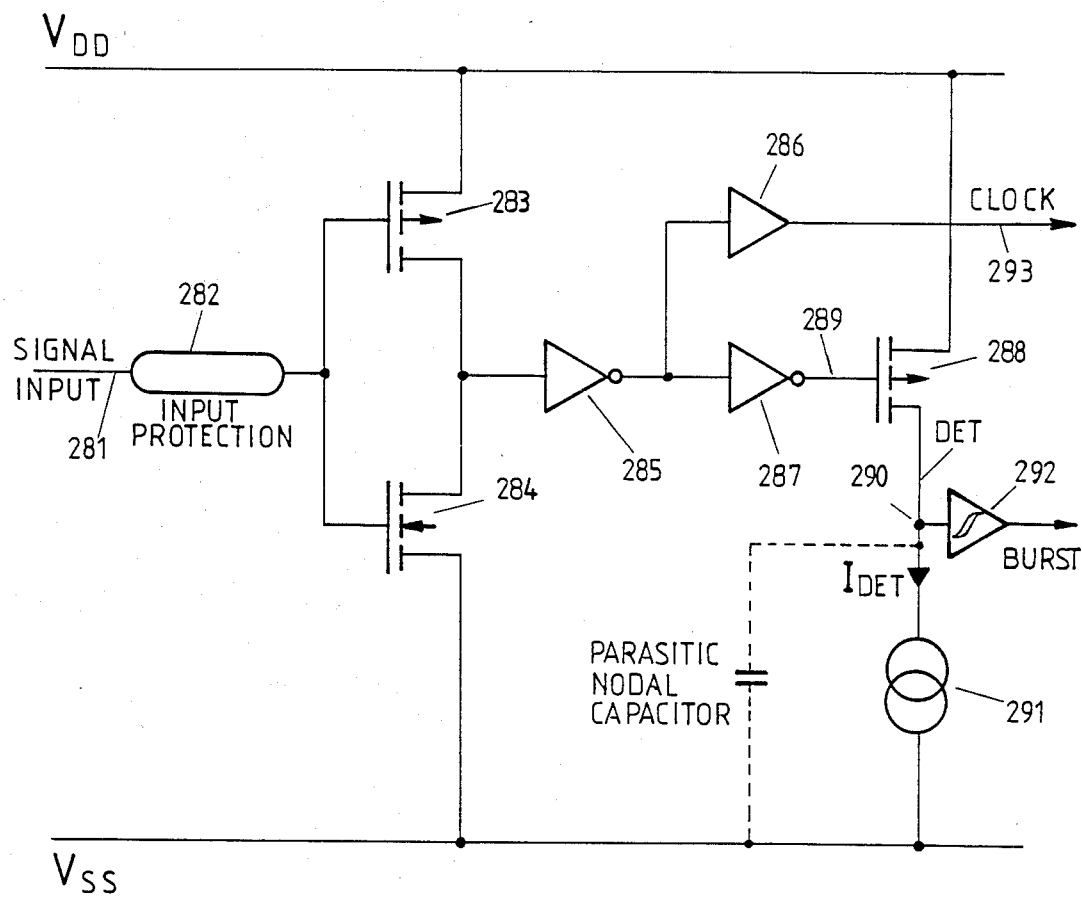
FIG. 11: Burst Detector & Clock Extraction Circuit

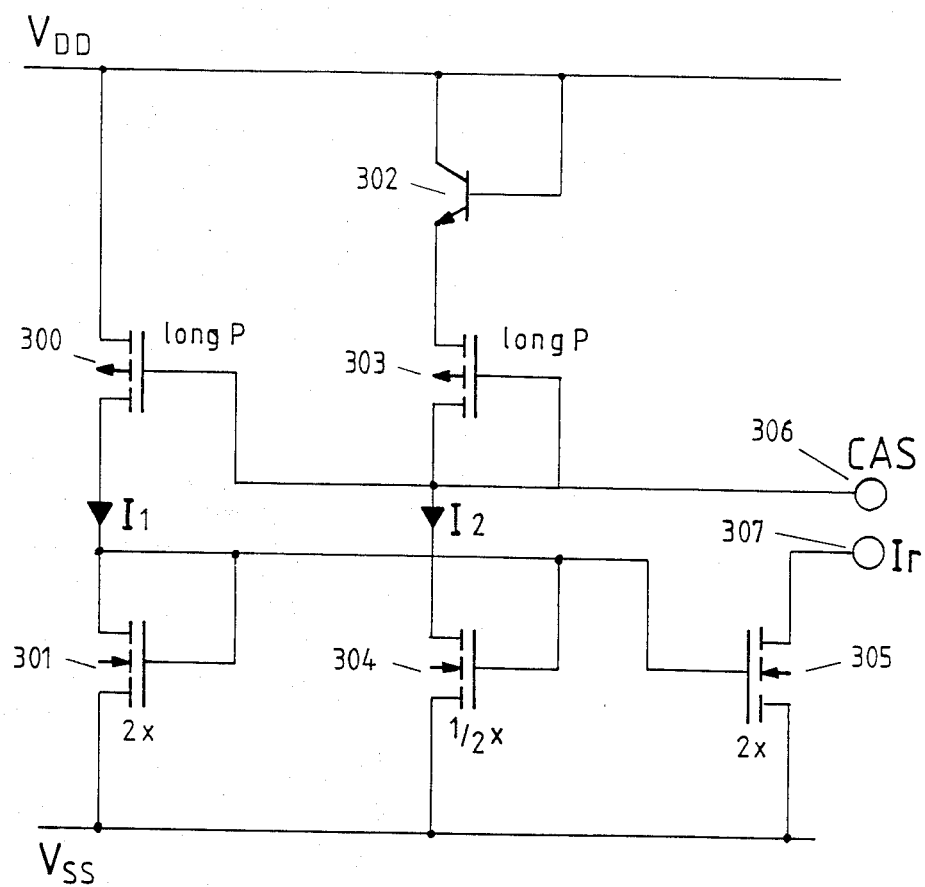
FIG.12: Reference Current Generator

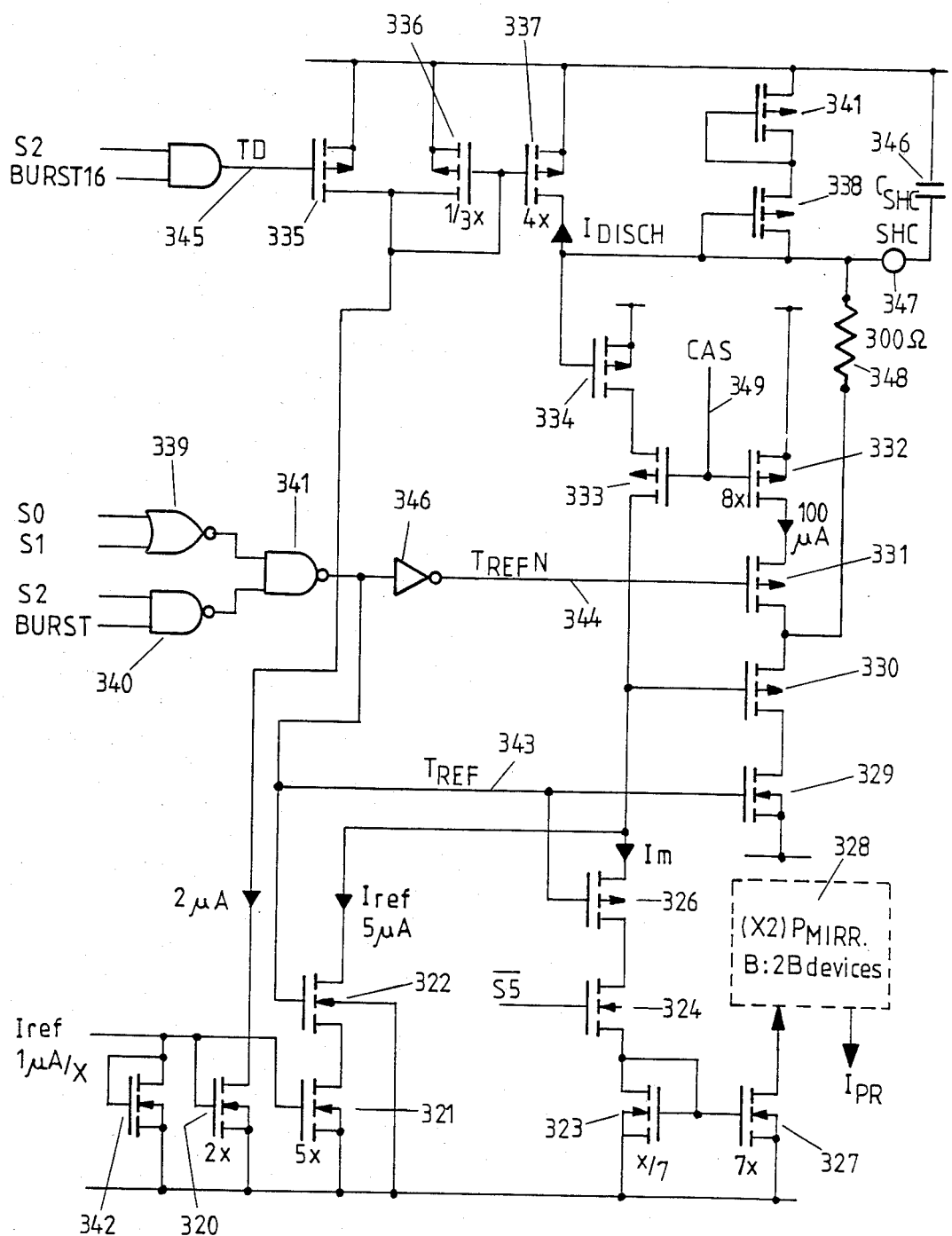
FIG.13: Programmable Current Generator

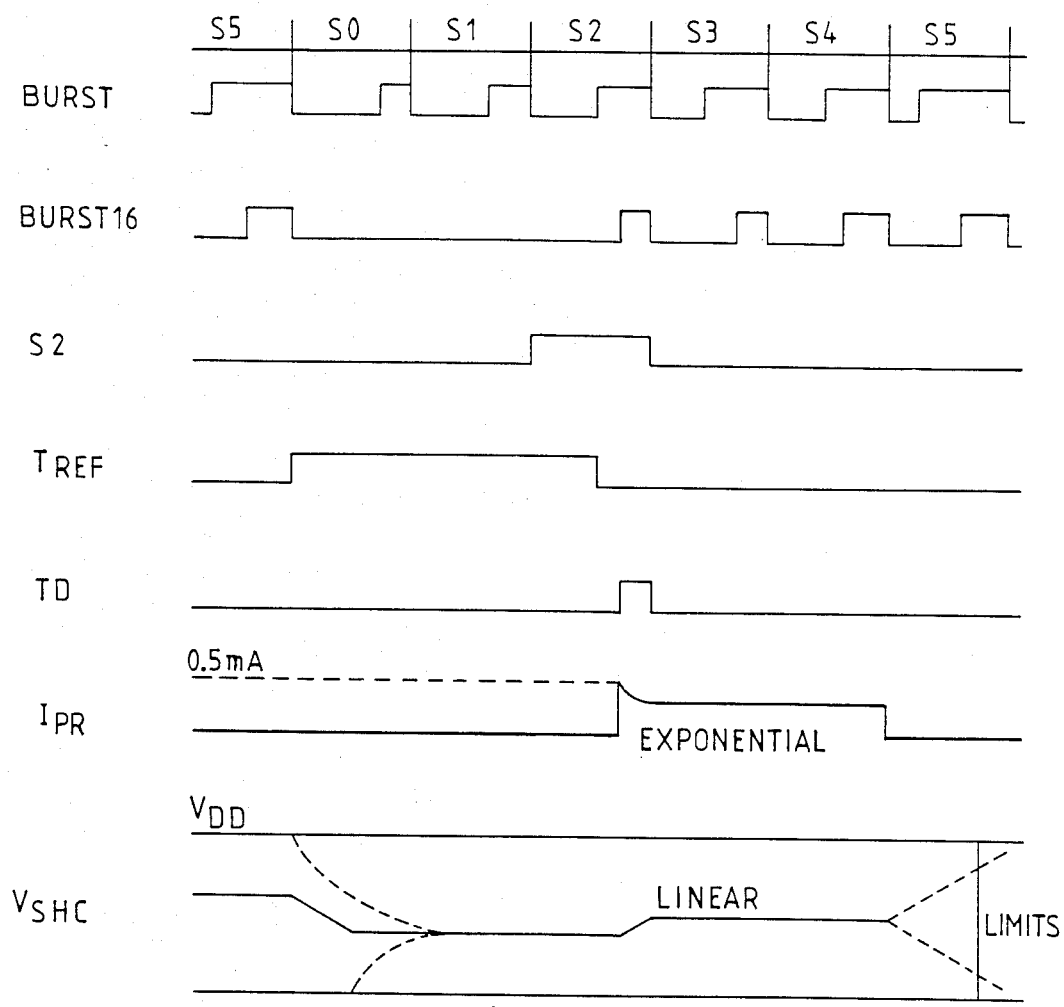
FIG. 14: Programmable Current Generator Timing

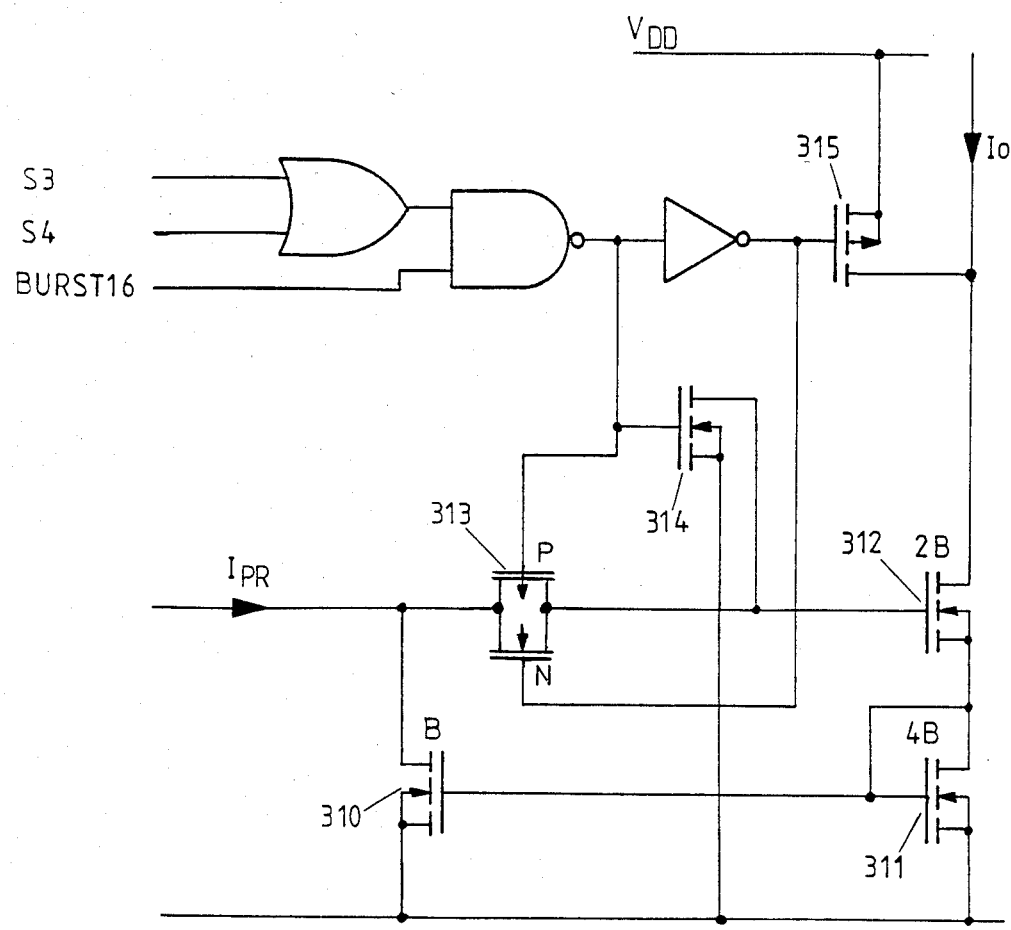
(a) Current source - output circuit
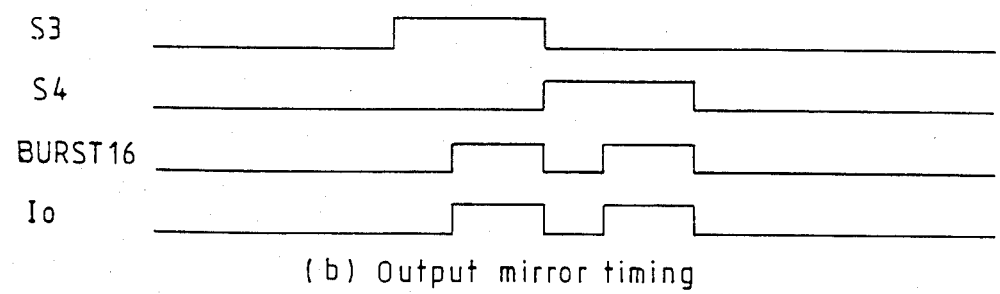
(b) Output mirror timing
FIG.15 Output Mirror

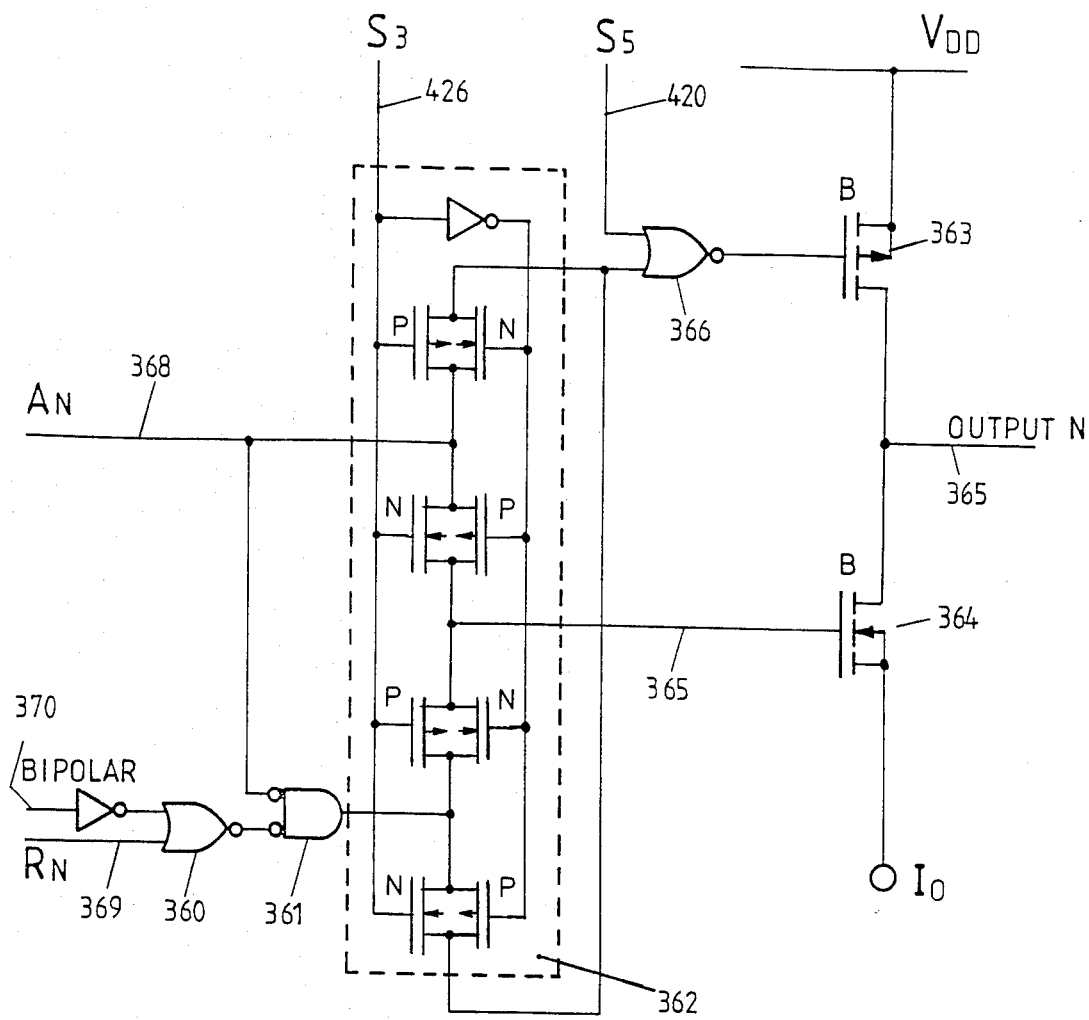
FIG.16: Output Switching Circuit, (output N)

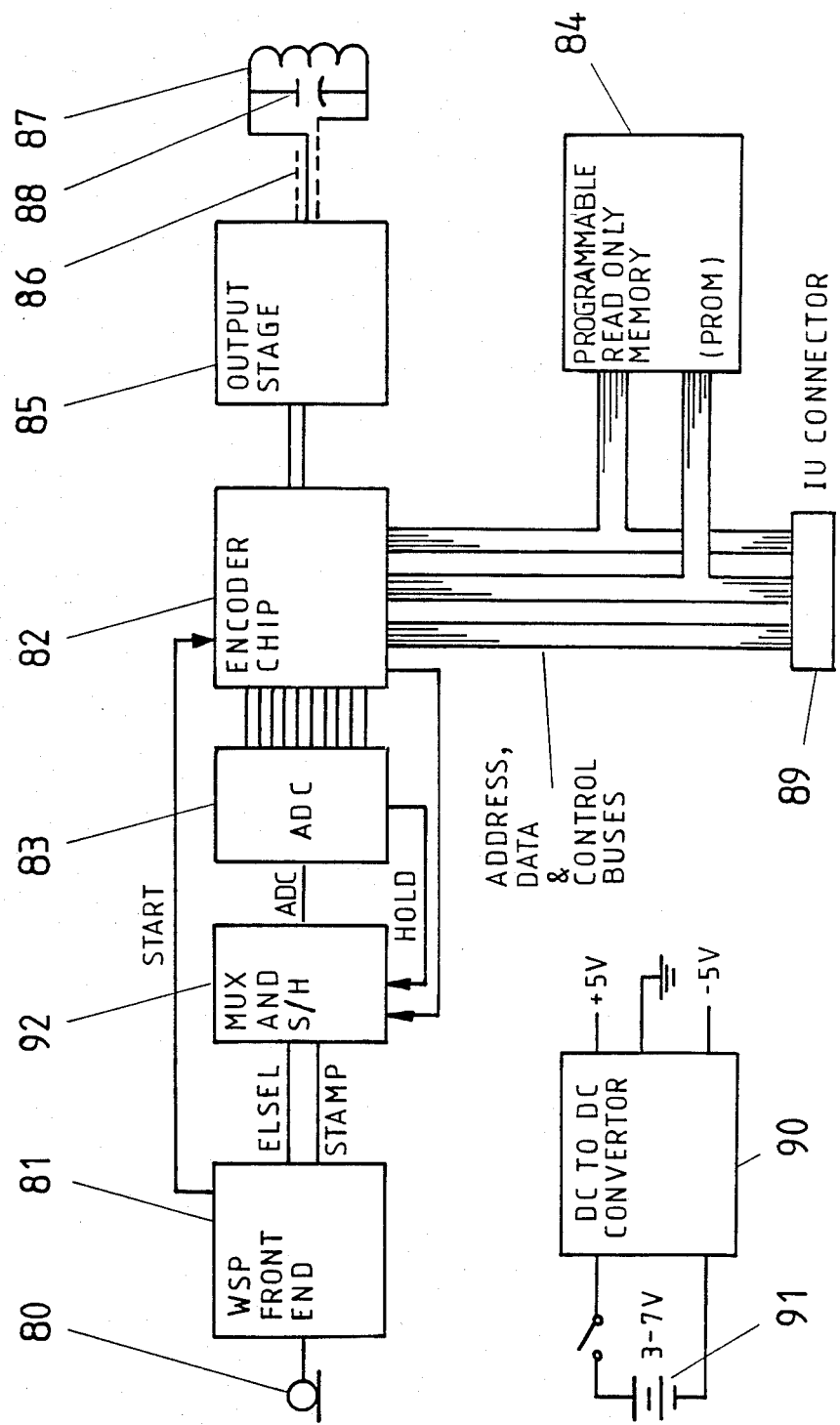
FIG. 17 Wearable Speech Processor Block Diagram

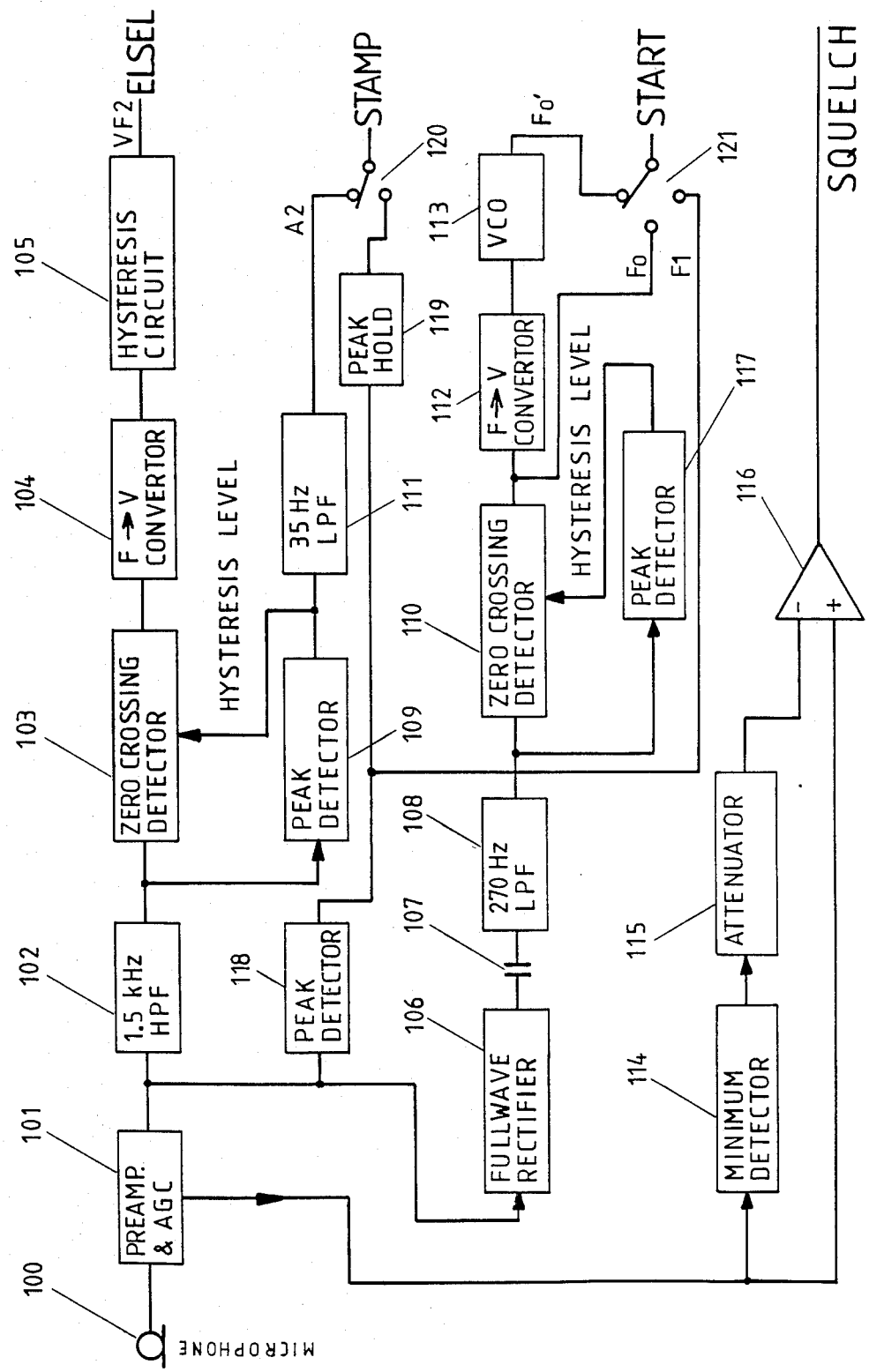
FIG. 18 WSP Front End Block Diagram

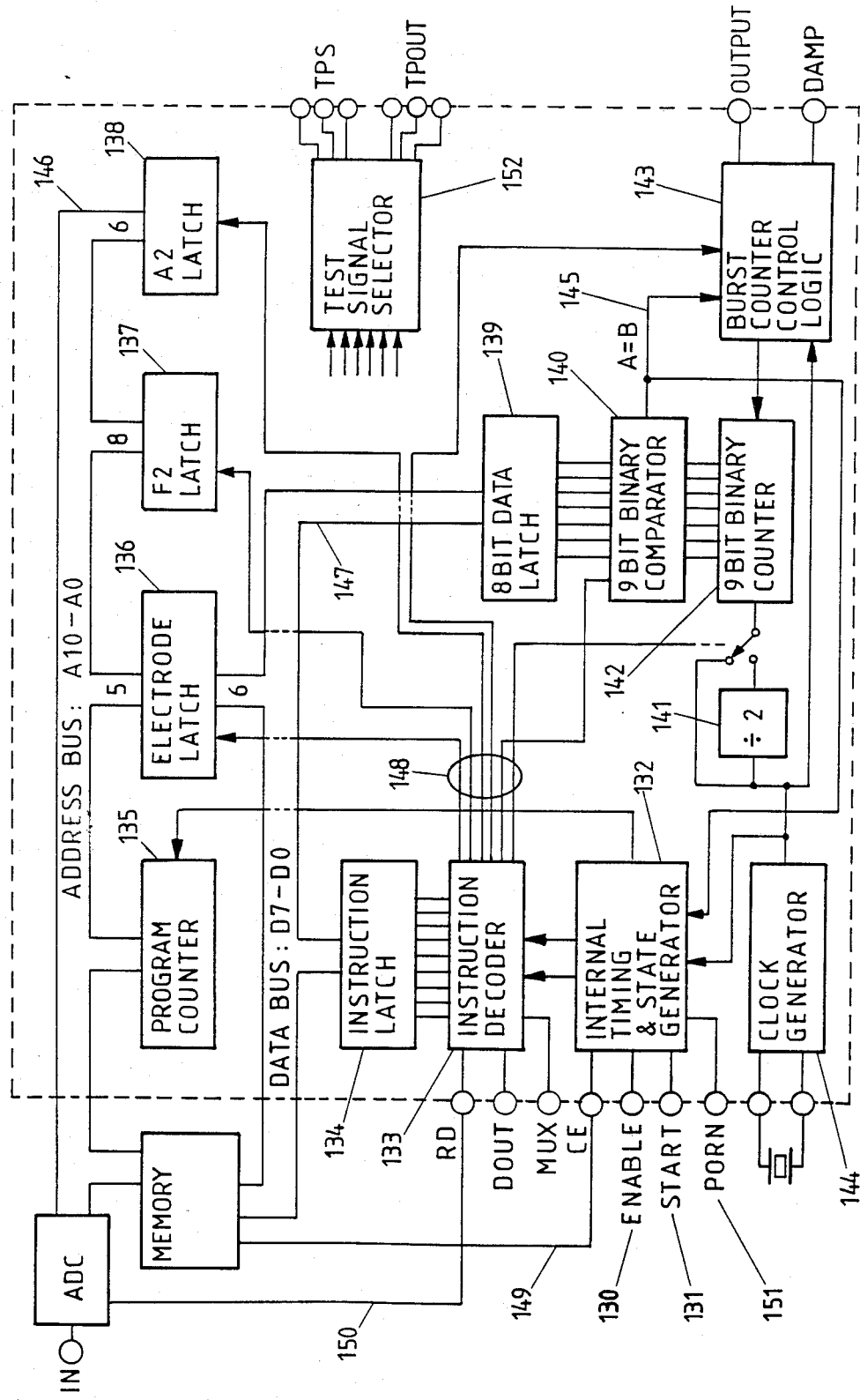
FIG.19 Speech Processor Encoder

PROM ADDRESS MAP

|   | A10 | A9 | A8 | A7 | A6 | A5 | A4 | A3 | A2 | A1 | A0 | DESCRIPTION | D7 | D6 | D5 | D4 | D3 | D2 | D1 | D0 |
|---|---|---|---|---|---|---|---|---|---|---|---|---|---|---|---|---|---|---|---|---|
| a) | 1/0 | ← ADC Value → | | | | | | | | 1 | 1 | F2 Input, electrode output | 0 | ← electrode → | | | | | 1 | 0 |
| b) | 1/0 | 1 | 1 | ← program counter → | | | | | | 1 | 1 | instruction address space | | | | see figure 2 | | | | |
|   |   |   |   | MSB | | | | | | LSB | |   |   |   |   |   |   |   |   |   |
| c) | 1/0 | ← Amplitude → | | | ← Electrode → | | | | | | | amplitude + electrode input, stimulus length output | ← length → | | | | | | | |
|   |   | MSB | | LSB | MSB | | | | | LSB | |   |   |   |   |   |   |   |   |   |

NOTES ON BIT 10 UTILIZATION a) When address input is ADC value (8 bits), the A10 bit is used to select which half of the 2Kx8 PROM space the F2 to electrode mapping is to be found. A10 is thus set by A10D under program control.

b) In the Instruction Address Space, A10 is the most significant bit of the Program Counter.

c) In electrode and amplitude (ADC) input, the A10 bit may be used in two ways:

i. to determine which half of the address space the mapping is to be found ( like in "a") under program control with A10D.

ii. as an extra (least significant) bit of ADC input to extend the precision of amplitude ADC data input from 5 to 6 bits.

The choice of i or ii is under program control.

FIG. 20

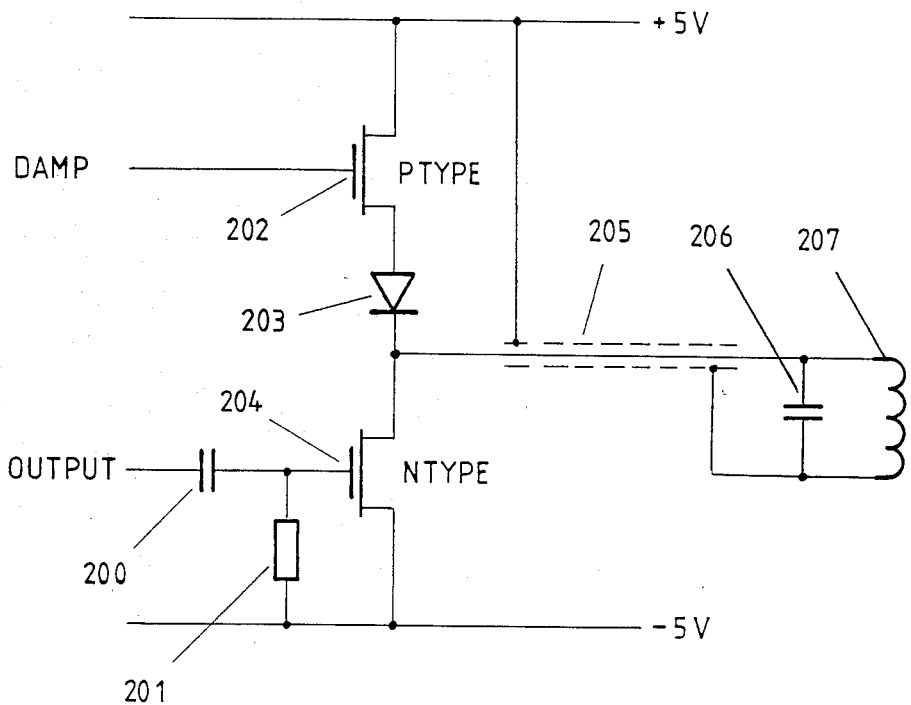
FIG. 21 WSP Output Stage

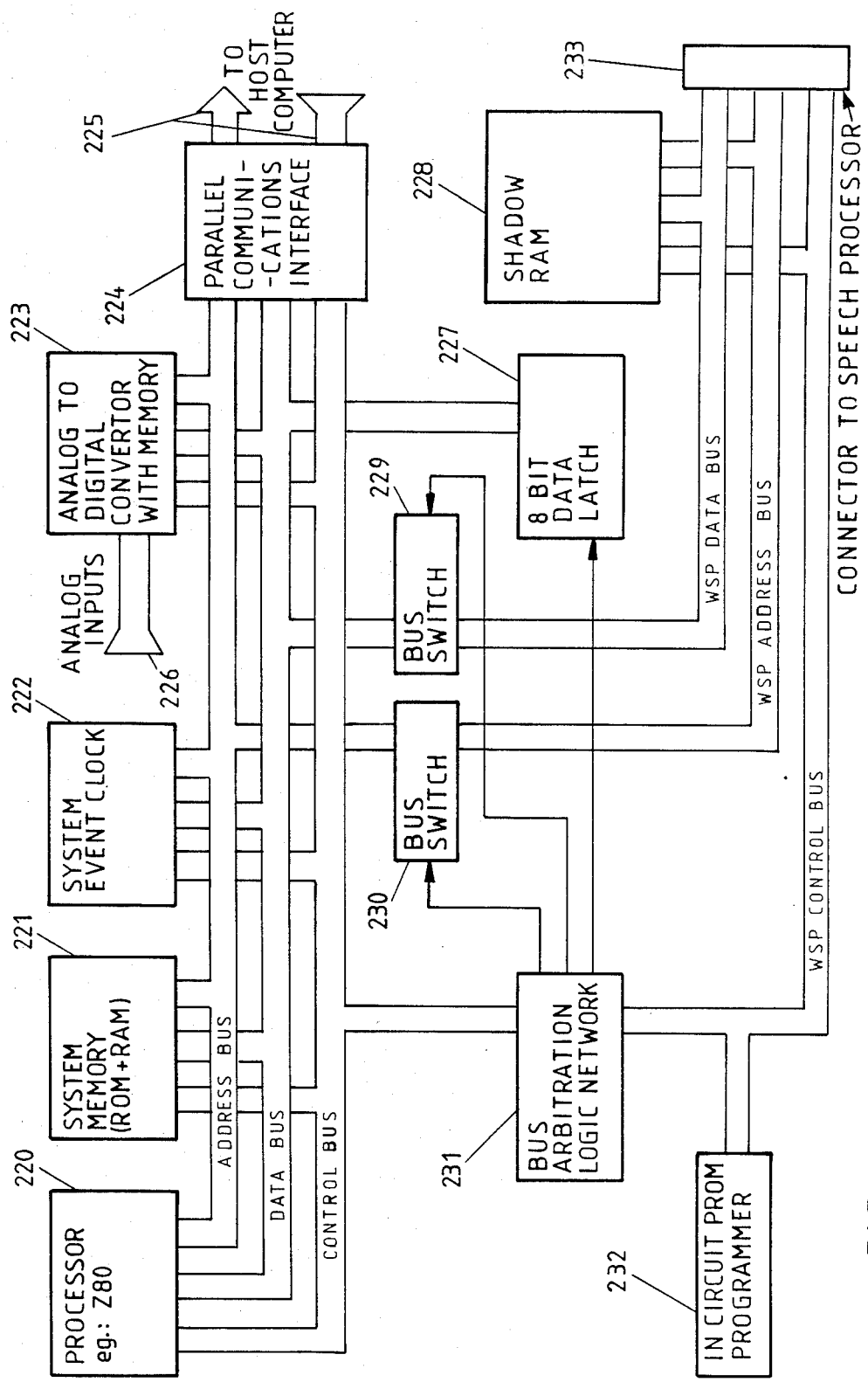
FIG. 22 : Interface Unit

| A | B | C | Io/Iin |
|---|---|---|--------|
| 0 | 0 | 0 | 1 |
| 1 | 0 | 0 | 1.25 |
| 0 | 1 | 0 | 1.5 |
| 1 | 1 | 0 | 1.875 |
| 0 | 0 | 1 | 0.444 |
| 1 | 0 | 1 | 0.555 |
| 0 | 1 | 1 | 0.666 |
| 1 | 1 | 1 | 0.8325 |

Current Trim Network

STATE and OUTPUT TIMING

COCHLEAR IMPLANT SYSTEM FOR AN AUDITORY PROSTHESIS

CROSS-REFERENCE TO RELATED APPLICATIONS

This invention is an improvement over the copending application of C. N. Daly and D. K. Money entitled "Implantable Tissue-Stimulating Prosthesis," U.S. patent application Ser. No. 252,319, filed Apr. 9, 1981, now U.S. Pat. No. 4,408,608. It also relates to copending U.S. patent application Ser. No. 233,585, filed Jan. 27, 1981, for Speech Processor and copending U.S. patent application Ser. No. 402,227, filed July 27, 1982 for "Cochlear Prosthetic Package and Method of Making Same" and U.S. patent application Ser. No. 46,167, filed Jan. 27, 1983 on an invention of Kuzma entitled "A Cochlear Prosthesis Package Connector." The subject matter of all such application is hereby incorporated by reference.

BACKGROUND OF THE INVENTION

The invention described is primarily for a cochlear prosthesis, or implantable hearing prosthesis system, or bionic ear. That is, a system of components designed with the object of restoring some sensations of hearing to the profoundly deaf. The main object of the invention is to improve speech communication, but the importance of awareness of environmental sounds is also taken into account.

In many people who are profoundly deaf, the reason for deafness is absence of, or destruction of the hair cells in the cochlea which transduce acoustic signals into nerve impulses. These people are thus unable to derive any benefit from conventional hearing air systems, no matter how loud the acoustic stimulus is made, because there is no way nerve impulses can be generated from sound in the normal manner.

The cochlear implant system seeks to bypass these hair cells in the cochlea by presenting electrical stimulation to the auditory nerve fibers directly, leading to the perception of sound in the brain. There have been many ways described in the past for achieving this object, including implantation of electrodes in the cochlea connected to the outside world via a cable and connector attached to the patient's skull; to sophisticated multichannel devices communicating with an external computer via radio frequency power and data links.

The invention described herein comprises a multichannel electrode implanted into the cochlea, connected to a multichannel implanted stimulator unit, which receives power and data from an externally powered wearable speech processor, wherein the speech processing strategy is based on known psychophysical phenomena, and is customized to each individual patient, by use of a diagnostic and programming unit.

In order to best understand the invention, it is necessary to be aware of some of the physiology and anatomy of human hearing, and have a knowledge of the characteristics of the speech signal. In addition, since the hearing sensations elicited by electrical stimulation are different from those produced by acoustic stimulation in a normal hearing person, it is necessary to discuss the psychophysics of electrical stimulation of the auditory system.

THE STRUCTURE OF THE COCHLEA

In a normal hearing person, sound impinges on the eardrum as illustrated in FIG. 1 and is transmitted via a system of bones called the ossicles which act as levers to provide amplification and acoustic impedance matching, to a piston, or membrane, called the oval window.

The cochlear chamber is about 35 mm long when unrolled and is divided along most its whole length by a partition. This partition is called the basilar membrane. The lower chamber is called the scala tympani. An opening at the remote end communicates between the upper and lower halves. The cochlea is filled with a fluid with a viscosity of about twice that of water. The scala tympani is provided with another piston or membrane called the round window which serves to take up the displacement of the fluid when the oval window is moved.

When the oval window is acoustically driven via the ossicles, the basilar membrane is displaced by the movement of fluid in the cochlea. By the nature of its mechanical properties, the basilar membrane vibrates maximally at the remote end or apex for low frequencies and near the base or oval window for high frequencies. The displacement of the basilar membrane stimulates a collection of cells called the hair cells situated in a special structure on the basilar membrane. Movements of these hairs produce electrical discharges in fibers of the VIIIth nerve or auditory nerve. Thus the nerve fibers from hair cells closest to the round window (the basal end of the cochlea) convey information about high frequency sound, and fibers more apical convey information about low frequency sound. This is referred to as the tonotopic organization of nerve fibers in the cochlea.

Hearing loss may be due to many causes, and is generally of two types. Conductive hearing loss is where the normal mechanical pathways for sound to reach the hair cells in the cochlea are impeded, for example by damage to the ossicles. Conduction hearing loss may often be helped by use of hearing aids, which amplify sound so that acoustic information does reach the cochlea. Some types of conductive hearing loss are also amenable to alleviation by surgical procedures.

Sensorineural hearing loss results from damage to the hair cells or nerve fibers in the cochlea. For this type of patient, conventional hearing aids will offer no improvement, because the mechanisms for transducing sound energy into nerve impulses have been damaged. It is by directly stimulating the auditory nerve that this loss of function can be partially restored.

In the system described herein, and in some other cochlear implant systems in the prior art, the stimulating electrode or electrodes is surgically placed in the scala tympani, in close proximity to the basilar membrane as shown in cross-section in FIG. 1B, and currents passed between the electrodes result in neural stimulation in groups of nerve fibers.

The human speech production system consists of a number of resonant cavities, the oral and nasal cavities, which may be excited by air passing through the glottis or vocal chords, causing them to vibrate. The rate of vibration is heard as the pitch of the speaker's voice and varies between about 100 and 400 Hz. The pitch of female speakers is generally higher than that of male speakers.

It is the pitch of the human voice which gives a sentence intonation, enabling the listener, for instance, to be able to distinguish between a statement and a question, segregate the sentences in continuous discourse and detect which parts are particularly stressed. This together with the amplitude of the signal provides the so-called prosodic information.

Speech is produced by the speaker exciting the vocal cords, and manipulating the acoustic cavities by movement of the tongue, lips and jaw to produce different sounds. Some sounds are produced with the vocal cords excited, and these are called voiced sounds. Other sounds are produced by other means, such as the passage of air between teeth and tongue, to produce unvoiced sounds. Thus the sound 'z' is a voiced sound, whereas 's' is an unvoiced sound; 'b' is a voiced sound, and 'p' is an unvoiced sound, etc.

The speech signal can be analyzed in several ways. One useful analysis technique is spectral analysis, whereby the speech signal is analyzed in the frequency domain, and a spectrum is considered of amplitude (and phase) versus frequency. When the cavities to the speech production system are excited, a number of spectral peaks are produced, and the frequencies and relative amplitudes of these spectral peaks also vary with time.

The number of spectral peaks ranges between about three and five and these peaks are called FORMANTS. These formants are numbered from the lowest frequency formant, conventionally called F1, to the highest frequency formants, and the voice pitch is conventionally referred to as Fo. Characteristic sounds of different vowels are produced by the speaker changing the shape of the oral and nasal cavities, which has the effect of changing the frequencies and relative intensities of these formants.

In particular, it has been found that the second formant (F2) is important for conveying vowel information. For example, the vowel sounds 'oo' and 'ee' may be produced with identical voicing of the vocal cords, but will sound different due to different second formant characteristics.

There is of course a variety of different sounds in speech and their method of production is complex. For the purpose of understanding the implant system however, it is sufficient to remember that there are two main types of sounds—voiced and unvoiced; and that the time course of the frequencies and amplitudes of the formants carries most of the intelligibility of the speech signal.

PSYCHOPHYSICS

The term Psychophysics is used here to refer to the study of the perceptions elicited in patients by electrical stimulation of the auditory nerve. For stimulation at rates between 100 and 400 pulses per second, a noise is perceived which changes pitch with stimulation rate. This is such a distinct sensation that it is possible to convey a melody to a patient by its variation.

By stimulating the electrode at a rate proportional to voice pitch (Fo), it is possible to convey prosodic information to the patient. This idea is used by some cochlear implant systems as the sole method of information transmission, and may be performed with a single electrode.

It is more important to convey formant information to the patient as this contains most of the intelligibility of the speech signal. It has been discovered by psychophysical testing that just as an auditory signal which stimulates the remote end of the cochlea produces a low frequency sensation and a signal which stimulates the near end produces a high frequency sensation, a similar phenomenon will be observed with electrical stimulation. The perceptions elicited by electrical stimulation at different positions inside the cochlea have been reported by the subjects as producing percepts which vary in "sharpness" or "dullness", rather than pitch as such. However, the difference is frequency perceptions between electrodes is such that formant, or spectral information can be coded by selection of electrode, or site of stimulation in the cochlea.

It has been found by psychophysical testing that the perceived loudness of sounds elicited by electrical stimulation of the auditory nerve has a larger dynamic range than the dynamic range of the stimulation itself. For example, a 2 to 20 dB dynamic range of electrical stimulation may produce perceptions from threshold or barely perceivable, to threshold of pain. In normal hearing people the dynamic range of sound perception is in the order of 100 dB.

It has also been discovered through psychophysical testing that the pitch of sound perceptions due to electrical stimulation is also dependent upon frequency of stimulation, but the perceived pitch is not the same as the stimulation frequency. In particular, the highest pitch able to be perceived through the mechanism of changing stimulation rate alone is in the order of 1 kHz, and stimulation at rates above this maximum level will not produce any increase in frequency or pitch of the perceived sound. In addition, for electrical stimulation with the cochlea, the perceived pitch depends upon electrode position. In multiple electrode systems, the perceptions due to stimulation at one electrode are not independent of the perceptions due to simultaneous stimulation of nearby electrodes. Also, the perceptual qualities of pitch, 'sharpness', and loudness are not independently variable with stimulation rate, electrode position, and stimulation amplitude.

Some systems of cochlear implants in the prior art are arranged to stimulate a number of electrodes simultaneously in proportion to the energy in specific frequency bands, but this is done without reference to the perceptions due to stimulus current in nearby stimulating electrodes. The result is that there is interaction between the channels and the loudness is affected by this.

PRIOR ART

A number of attempts have been made to provide useful hearing through electrical stimulation of auditory nerve fibers, using electrodes placed inside or adjacent to some part of the cochlear structure. Systems using a single pair of electrodes have been proposed by House (Ann. Otol. Rhinol. Laryngol. 85, Supp. 27, 1976), Michelson (U.S. Pat. No. 3,751,605) and Bartz (U.S. Pat. No. 3,752,939).

In each of these systems an external speech processing unit converts the acoustic input into a signal suitable for transmission through the skin to an implanted receiver/stimulator unit. These devices apply a continuously varying stimulus to the pair of electrodes, stimulating at least part of the population of auditory nerve fibers, and thus producing a hearing sensation.

The stimulus signal generated from a given acoustic input is different for each of these systems, and while some degree of effectiveness has been demonstrated for each, performance has varied widely across systems and also for each system between patients. Because the design of these systems has evolved empirically, and has not been based on detail psychophysical observations, it has not been possible to determine the cause of this variability. Consequently, it has not been possible to reduce it.

An alternative approach has been to utilize the tonotopic organization of the cochlea to stimulate groups of nerve fibers depending on the frequency spectrum of the acoustic signal. Systems using this technique have been proposed by Ricard (U.S. Pat. No. 4,207,441), Hochmair (Med & Biol Eng. & Comput., 1981, 19, 141–148), Doyle (U.S. Pat. No. 3,449,753), and Kissiah (U.S. Pat. No. 4,063,048).

The system described by Kissiah uses a set of analog filters to separate the acoustic signal into a number of frequency components, each having a predetermined frequency range within the audio spectrum. These analog signals are converted into digital pulse signals having a pulse rate equal to the frequency of the analog signal they represent, and the digital signals are used to stimulate the portion of the auditory nerve normally carrying the information in the same frequency range. Stimulation is accomplished by placing an array of spaced electrodes inside the cochlea.

This system utilizes electrical stimulation at rates up to the limit of normal acoustic frequency range, say 10 kHz, and independent operation of each electrode. Since the maximum rate of firing of any nerve fiber is limited by physiological mechanisms to one or two kHz, and there is little perceptual difference for electrical pulse rates above 800 Hz, it may be inappropriate to stimulate at the rates suggested. No consideration has been given to the interaction between the stimulus currents generated by different electrodes which in our experience may cause considerably, uncontrolled loudness variations, depending on the relative timing of stimulus presentations. Also, this system incorporates a percutaneous connector which has with it the associated risk of infection.

The system proposed by Doyle limits the stimulation rate for any group of fibers to a rate which would allow any fiber to respond to sequential stimuli. It utilizes a plurality of transmission channels, with each channel sending a simple composite power/data signal to a bipolar pair of electrodes. Voltage source stimulation is used in a time multiplexed fashion similar to that subsequently used by Ricard and described below, and similar uncontrolled loudness variations will occur with the suggested independent stimulation of neighbouring pairs of electrodes. Further, the requirement for a number of transmission links equal to the number of electrode pairs prohibits the use of this type of system for more than a few electrodes.

The system proposed by Ricard again utilizes a filter bank to analyze the acoustic signal and a single radio frequency link to transfer both power and data to the implanted receiver/stimulator, which presents a time-multiplexed output to sets of electrodes implanted in the cochlea. Monophasic voltage stimuli are used, with one electrode at a time being connected to a voltage source while the rest are connected to a common ground line. An attempt is made to isolate stimulus currents from one another by placing small pieces of silastic inside the scala, between electrodes. Since monophasic voltage stimuli are used, and the electrodes are returned to the common reference level after presentation of each stimulus, the capacitive nature of the electrode/electrolyte interface will cause some current to flow for a few hundred microseconds after the driving voltage has been returned to zero. This will reduce the net transfer of charge (and thus electrode corrosion) but this charge recovery phase is now temporarily overlapped with the following stimulus or stimuli. Any spatial overlap of these stimuli would then cause uncontrolled loudness variations.

The system described by Forster et al. (U.S. Pat. No. 4,267,410) utilizes biphasic current stimuli of predetermined duration, providing good temporal control of both stimulating and recovery phases. However, the use of fixed pulse duration prohibits the variation of this parameter which may be required by physiological variations between patients. Further, the data transmission system described in this system severely limits the number of pulse rates available for constant rate stimulation.

A common feature of all implanted receiver/stimulator units has been that the energy needed to power the implanted electronics (if any) and deliver the stimulus signal has been derived from an external power source, either directly from the data signal or from a separate power signal.

The simplest and thus more reliable systems are those utilizing a single link, such as those described by Ricard and Hochmair. The Hochmair multichannel system uses FM data coding to transfer energy continuously, even during long intervals between stimuli. The energy efficiency of this approach is inherently less than that of approaches which transfer energy only when stimulation is imminent or actually in progress such as the Ricard system, and the system described herein.

In the Ricard system a start pulse providing enough energy to power the electronics is sent at the start of every stimulation sequence. Each electrode is stimulated only once during each sequence, so for a series of stimuli to any single electrode the number of start bursts is equal to the number of stimuli. An improvement to this technique is to eliminate the need for the start pulse by minimizing the energy consumption of the electronics between stimuli (when no energy being received), allowing the electronics to still be in an active or powered state when the second and subsequent stimulus data sequences are received. This concept is utilized in the invention described herein.

It is necessary to be able to configure the cochlear implant system to take account of each individual patient's psychophysical response to stimulation. The system by Merzenich uses an interconnection pad between the implanted stimulator unit and the electrode array which enables him to select the electrode configuration to suit the patient's responses. This is done in a second surgical procedure after implantation. Other systems may use several implanted electrodes, and after testing, a choice is made of which electrode or electrodes are to be stimulated as a single channel.

SUMMARY OF THE INVENTION

The primary aim of the invention to be described is to provide hearing sensations by electrical stimulation of the auditory nerve to alleviate the handicap in people suffering from profound sensironeural hearing loss, by means of an improved cochlear implant system.

Considering the requirements of a cochlear implant system, and some of the deficiencies of prior art systems pointed out above, the aims and objects of this invention are:

to provide a means where known and controllable electrical stimulation may be delivered to an electrode(s) of an electrode strip array positioned inside the cochlea;

to provide a means satisfying the above object in a sufficiently small package that is suitable for implantation inside the human body;

to provide a means for transmitting power and information to the implanted cochlear stimulator across the skin without requiring a break in the skin;

to provide a means for generating the information on which electrode to stimulate and at what amplitude on a stimulus to stimulus basis and derived from an acoustic signal;

to provide a means for configuring the cochlear implant system to take account of each patient's unique characteristics, and to be able to perform this function without resort to extra surgery, or custom-made implantable components; and to design the cochlear implant system with the primary aim to improved speech communication, but also providing an awareness of environmental sounds.

The invention operates efficiently with low power consumption and is sufficiently flexible in design to be capable of other (as yet undefined) speech processing strategies.

The invention contemplates that several of the subsystems will have separate utility in general in various other tissue stimulating prosthesis.

This invention will be more fully understood in view of the following detailed description taken together with the drawings.

BRIEF DESCRIPTION OF THE DRAWINGS

FIG. 6 is the electrode switching circuit for bipolar stimulus current generation.

FIG. 7 is a block diagram of the distributed ground stimulus current generation.

FIG. 8 illustrates the power/data signal format from the speech processor.

FIG. 9 is a block diagram of the implanted receiver/stimulator digital circuit.

FIG. 10 is a block diagram of the implanted receiver/stimulator analog circuit.

FIG. 11 is the burst detector and clock extraction circuit.

FIG. 12 is the reference current generator.

FIG. 13 is a programmable current generator.

FIG. 14 shows the programmable current generator timing waveforms.

FIG. 15 shows the output circuit (a) and output timing waveforms (b) of the output mirror.

FIG. 16 is the output switching circuit of the receiver/stimulator.

FIG. 17 is a block diagram of the speech processor.

FIG. 18 is a block diagram of the speech processor front end.

FIG. 19 is a block diagram of the speech processor encoder.

FIG. 20 is an address map for the programmable read only memory.

FIG. 21 is a circuit diagram of the speech processor output stage.

FIG. 22 is a block diagram of the speech processor interface unit.

DETAILED DESCRIPTION

The Cochlear Implant System

Figure 2:
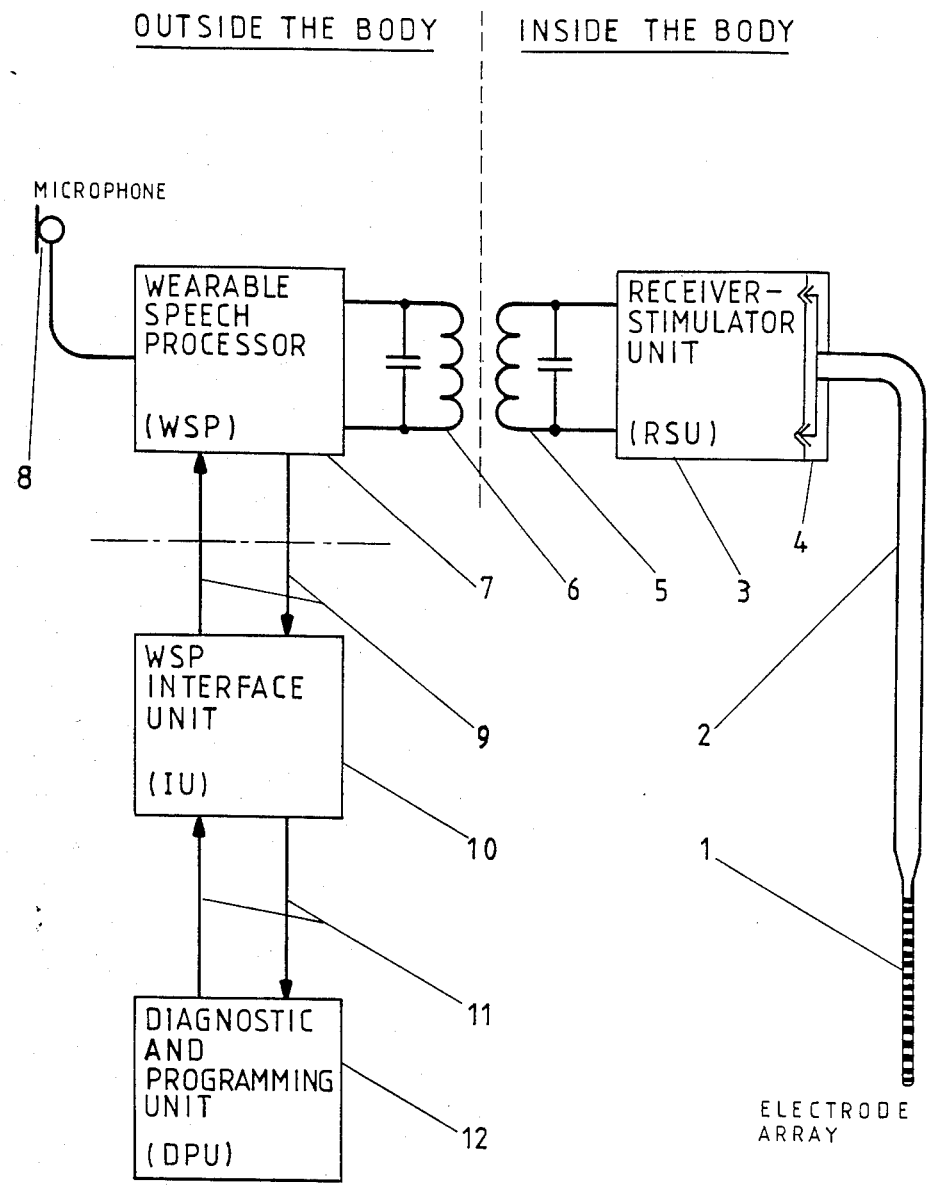
FIG. 2 is a block diagram of the overall cochlear implant system of this invention.

The cochlear implant system of this invention shown in FIG. 2 comprises several components.

An Electrode Array 1 is implanted into the cochlea. In the embodiment of the invention described, the electrode comprises a number of rings or bands of platinum moulded with a flexible silastic carrier. There are 32 bands of platinum in total, and the distal 22 bands are active electrodes, and have connecting wires welded to them. The proximal 10 electrode bands are used for stiffening, and to act as an aid to surgical insertion. In a typical array, the electrode rings are about 0.05 mm in thickness with a width of 0.3 mm, and have outside diameters ranging from 0.6 mm at the proximal end to about 0.4 mm diameter at the distal end. The diameter of the rings changes smoothly so that the array is tapered over the distal 10 mm or so. The rings are spaced on 0.75 mm centers, over the distal 25 mm of the electrode array, and all of the exposed outside area of the rings is used as active electrode area. Silastic material may be MDX4-4210, manufactured by Dow Corning. The 22 electrode wires pass in a cable 2 from the electrode to the Receiver—Stimulator Unit (RSU) 3 via a connector 4. The invention described is not limited to the use of this design of electrode array, and a number of alternative electrode designs as have been described in the prior art could be used, provided the wires from the active electrode sites could be attached to the connector. Reference may be made to the copending case Ser. No. 402,227 for details on the connector. The RSU receives information and power from an external source through a tuned receiving coil 5 attached to the RSU and just beneath the skin. The RSU also provides electrical stimulating pulses to the electrode. In the invention described herein, the electrical connection between the electrode and the RSU is via a connector to allow the RSU to be replaced without requiring explantation of the electrode.

The power, and data on which electrode to stimulate, and with what intensity, is transmitted across the skin using an inductive link 6 operating at radio frequencies, from an external Wearable Speech Processor (WSP) 7. In normal operation, the WSP picks up acoustic stimuli from a microphone 8 conveniently worn, and extracts from the signal, information which is used to determine stimulation electrode, rate and amplitude.

Because each patient's response to electrical stimulation is different, it is necessary to configure each patient's WSP to his or her own requirements. Thus the WSP has an Eraseable Programmable Read Only Memory (EPROM) which is programmed to suit each patient.

The patient's response to electrical stimulation is tested some short time after implantation of the RSU, using the patient's WSP, and the results of these tests are used to set up the WSP for the patient's own particular requirements. This is done by connecting the WSP, via a connector and cables 9, to an Interface Unit (IU) 10. The IU it itself connected via a cable and connector 11 to a general purpose computer referred to as a Diagnostic and Programming Unit (DPU) 12.

Figure 3:
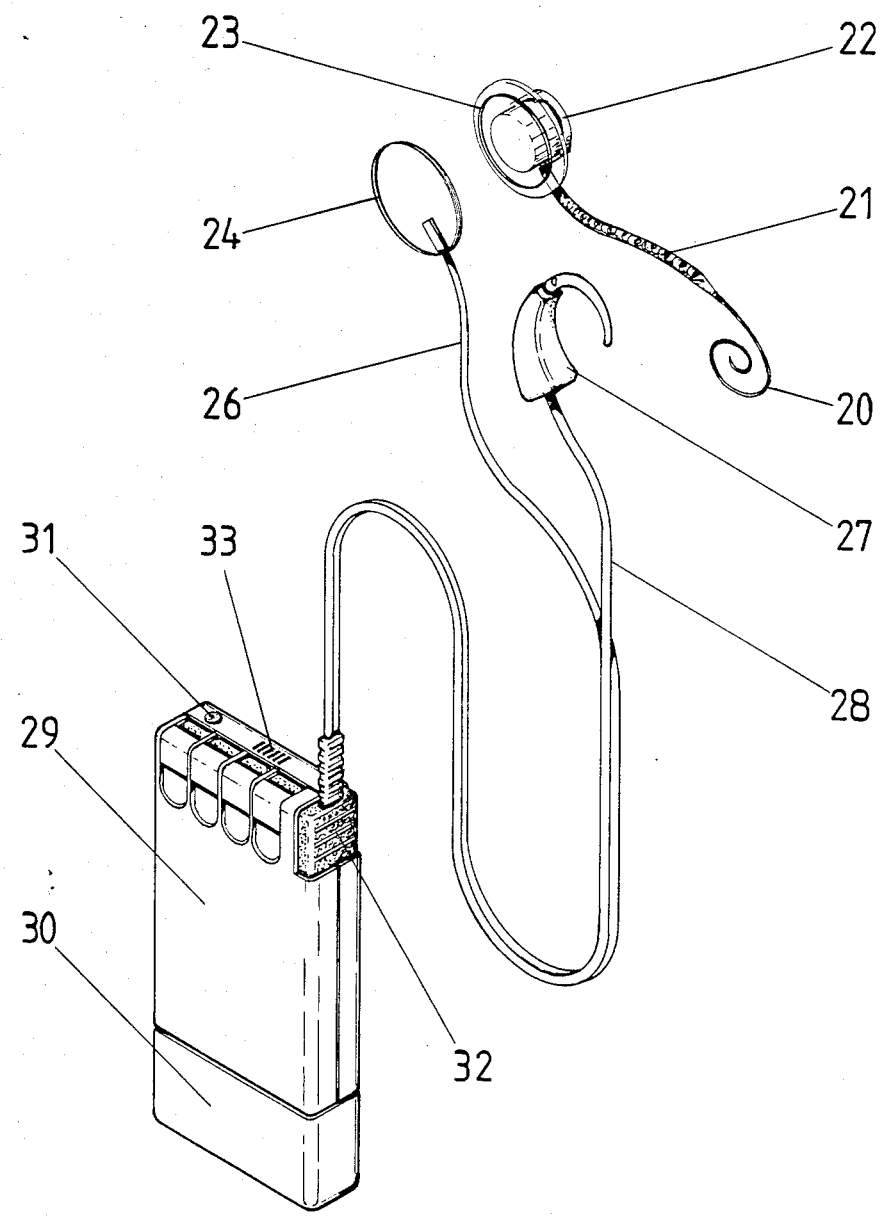
FIG. 3 is a pictorial view of the components of the system, including the implantable parts, and the parts worn by the patient.

A pictorial representation of the system used by the patient is shown in FIG. 3. The electrode array 20 is flexible and fits the shape of the cochlea as it is inserted along the basilar membrane separating the scala tympani from the remainder of the cochlea. The electrode array is connected via a silastic-covered cable 21 to the RSU 22. As pointed out in the previous Kuzma application Ser. No. 402,227, this cable is specially designed to provide some stress relief to prevent wire fracture. The receiving coil for information and power is a single turn of multistrand platinum wire 23 which is transformer coupled to the implanted electronics in the RSU.

An externally worn coil 24 is simply held against the head over the site of RSU implant by (for example) adhesive tape or a fixture, and is connected to the Speech Processor 29 by a coaxial cable 16. A conventional hearing aid microphone 27 is worn on the same ear as the transmitting coil, and a microphone lead 28 is contained in the same cable as the coil coaxial lead. Alternative microphone configurations are possible, including a microphone 33 mounted in the WSP case, or worn on a tie clasp or attached to the clothing, or attached to the fixture holding the transmitting coil.

The cable is attached to the WSP by a demountable connector 32. The WSP is powered by conventionally available batteries (e.g.: 3 AA size cells shown as 30). A facility exists for plugging in external signals sources 31, such as a television, radio, or high quality microphone to be handed around in a social stituation.

Each component of the cochlear implant system will be discussed in more detail in the following sections:

THE SPEECH PROCESSING STRATEGY

The main aim of this invention is to provide improved speech communication to those people suffering from profound hearing loss, and thus the emphasis in design has been to optimize stimulation parameters for speech signals. However, it is also important to be able to convey environmental sounds, for example telephones, doors, warning sirens, doorbells, etc., which form part of a persons life. We have found that the approaches which we have taken, although emphasizing speech communication, also enable good awareness of environmental sounds, and we feel that there is no loss of effectivenes in perception of environmental sounds by this approach.

It is believed by those skilled in the art that it is the second formant which carries most of the intelligibility of the speech signal. This fact can be demonstrated by high passing filtering a passage of speech at 1 kHz. The result is as intelligible as the original signal. Thus whilst the 1st formant contains much of the naturalness of the signal, it contributes little to intelligibility.

It may also be observed that the 3rd and higher formants do not carry as much information as the 2nd. Thus in view of the limitations of knowledge on the interaction between electrodes when a number of electrodes are stimulated simultaneously, at the present time the most effective method of stimulation has been found to be to code the second formant on a appropriate electrode or site in the cochlea to provide the most important formant information. The amplitude of stimulation is derived from the amplitude of the second formant.

The system described also provides prosodic information in the form of pulse rate. However, whereas other systems stimulate at the voice pitch rate, this system compresses the stimulation rate to the range 100 to 250 Hz, the range in which the greatest pitch discrimination from stimulation pulse rate is achieved.

An additional factor is that only the top 10 to 20 dB of current acoustic stimulus level is used to determine stimulus amplitude. That is, instead of compressing the entire acoustic loudness range into the small range of electrical stimulation available, only the top part is used. In fact, the amplitude of the signal is internally represented by a 5 bit binary code, which provides only 25 dB of dynamic range.

In summary, the speech processing strategy is:
1. The dominant spectral peak in the range of about 300 Hz to about 4 kHz is used to encode electrode position.
2. The amplitude of the dominant spectral peak used to encode electrode position is used to determine stimulation amplitude.
3. Voice Pitch (Fo) is compressed and used to determine stimulation rate.

For unvoiced sounds, and environmental sounds, the system will still generate stimuli, but the stimulation rate and electrode position will be determined by the exact nature of the acoustic signal. For example, for sibilant consonants ('s'), the stimulation rate will be fairly fast, but not constant, and the electrode stimulated will be one which elicits a high frequency percept.

A second alternative speech processing strategy has also been found to be useful in some patients, and we have discovered that it is advantageous to be able to offer a choice of strategies to patients. The second strategy is similar to the one mentioned above in that electrode position is encoded from formant frequency. However, the stimulation rate is at the Fl or first formant frequency, and the stimulation amplitude is determined from the value of the peak of the acoustic signal at the time of the Fl peak. This has the advantage that the stimulation rate is faster, and elicits more natural sounding speech perceptions in some patients. In addition, since the Fl signal is amplitude modulated and temporally patterned at the Fo rate, the patients also perceive the Fo or voice pitch which is useful for conveying prosodic information. The two alternative strategies and the method for generating them are later further discussed.

Another speech processing strategy we have considered is to stimulate the patient at the rate of Fl extracted from an incoming speech signal, but to pattern the stimulation such that the stimuli are gated at the Fo rate.

The cochlear implant system described herein is not limited to any one particular speech processing strategy. Indeed, it is one of the strengths of the invention that the implanted receiver unit is 'transparent' to the speech processing or sound encoding strategy adopted, and that future developments in this field will be able to be adapted without changes to the implant necessitating further surgery to the patient.

THE ELECTRICAL STIMULATION PULSE

Figure 4:
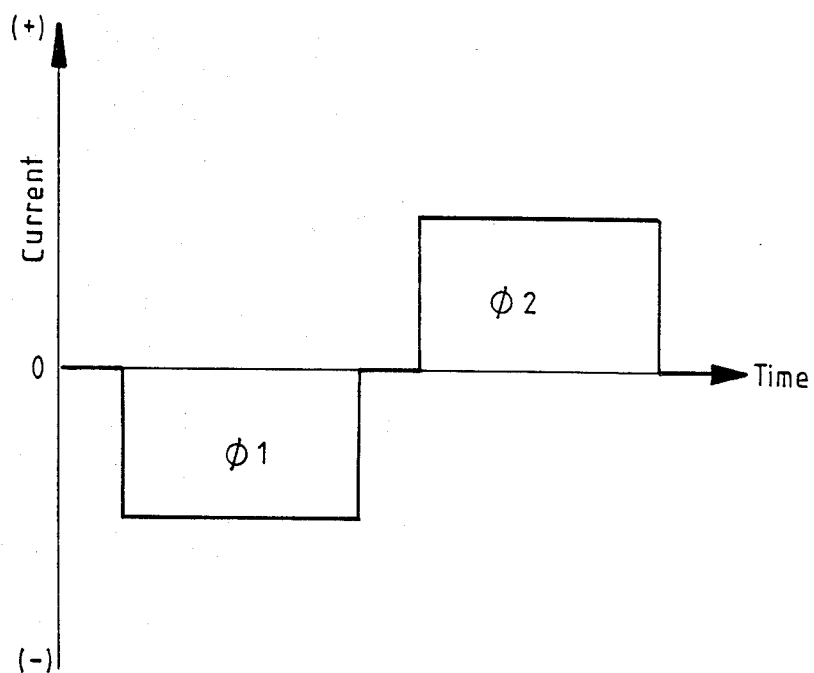
FIG. 4 is the biphasic current waveform utilized in this invention.

The pulse which is used to electrically stimulate the cochlea is BIPHASIC, as shown in FIG. 4. That is, it comprises a period of negative current stimulation, followed by an equal period of positive current stimulation of equal amplitude, the two periods (known as phases phi 1 and phi 2), separated by a short period of no stimulation. Phi 1 and phi 2 may be in the range of 50 to 400 microseconds (typically 200 microseconds), and the intervening interval is typically about 50 microseconds. The amplitude of phi 1 and phi 2, their durations, and the duration of the intervening interval are determined by the information decoded from the signal transmitted by the speech processor. The actual values of these parameters will be set up on an electrode by electrode basis, for each patient, as a result of psychophysical testing of the patient, as will be described. The reversal in polarity of phi 1 and phi 2 is important since it ensures that there is no net DC component in the stimulus. This is important because long term DC excitation might cause electrode corrosion, and possible subsequent damage to the cochlea itself.

The questions of electrode electrochemistry and charge balance are thought to be more important in cochlear implants than in, say, cardiac pacemakers which are well known in the art. This is because a cochlear stimulator will be stimulating nerve fibers, whereas a cardiac pacemaker is designed to stimulate cardiac muscle. It is thought that nerve tissues may be more susceptible to damage due to electrical stimulation, and thus the cochlear implant system described herein has been designed with more stringent safety factors than cardiac pacemakers.

The system is carefully designed so that the same stimulus source is used for both stimulation phases. The biphasic pulse is produced simply by reversal of the connections to the electrodes. Thus, extremely good charge symmetry is obtained resulting in a high level of safety provided the duration of phi 1 and phi 2 are equal. In other systems in the prior art, capacitors are used in series with the electrodes to overcome the problem of charge asymmetry. The need for capacitors in a cochlear implant puts constraints on the minimum volume possible, since one capacitor would be required for each electrode. Thus, for a 22 channel stimulator, 22 capacitors would be required, of typically 0.5 mocrofarad, 25 volt rating chip ceramic capacitor.

The stimulation circuitry is configured as a constant current source. This has the advantage compared to a constant voltage source that if the electrode impedance changes (as has often been observed) the delivered current to the electrode will remain unaltered over a large range of electrode impedances. The current may be varied from a few microamps to 2 mA, allowing a very large range of loudness percepts to be produced and large variations between patients to be accommodated.

In addition, the system has the unique feature that the stimulus currents as delivered to the cochlea are known, as the system of generating the constant current stimulus is very well characterized, and has been designed to be substantially independent of many parameters (such as transmitting coil position) over a wide range.

The stimulus generation circuitry in the RSU has been designed to operate in one of two modes. The first mode is referred to as 'multipolar' or 'common ground' stimulation. In this mode, one electrode is selected to be the 'active' electrode, and all other electrodes operate as a common current source. In phase 2, the connections are reversed so that the 'active' electrode acts as the current source and the common electrodes act as a current sink. The choice of stimulus order is not determined by any limitations or restrictions in the circuit design, and either way may be chosen when implementing the circuit design.

The second mode is 'bipolar' stimulation. In this mode, stimulation is between two selected electrodes, let us say A and B. In phase 1, current is sourced by A, and sunk by B. In phase 2, current is sourced by B, and sunk by A, and no other electrodes play any part in stimulation. The RSU is configured so that any pair of electrodes may be selected for bipolar stimulation. Thus, there is great flexibility in choice of stimulation strategy.

It should be understood that only these two particular stimulation modes have been chosen. Other stimulation modes are not excluded by the system described herein. For example, a multipolar or distributed ground system could be used where not all other electrodes act as a distributed ground, and any electrode could be selected at any time to be a current source, current sink, or inactive during either stimulation phase with suitable modification of the receiver-stimulator.

TESTING AND WSP PROGRAMMING

Once the receiver/stimulator and electrode have been surgically implanted, the patient is allowed to recover for a short time, usually two weeks or so. After recovery, a number of psychophysical tests are carried out to determine the sensitivity and sharpness of perceptions elicited by stimulating the electrodes. This is done by an audiologist using the Diagnostic and Programming Unit ("DPU"), Interface Unit, and the patient's own speech processor.

The testing may be done entirely under control of the audiologist, who can set a stimulus level, present the stimulus, and question the patient on his perceptions. Another technique we have found to be useful is to allow the patient to determine his own threshold stimulus level by adjusting a knob, slider or other patient operated control which can set the stimulus level. Thus, the patient can be instructed to set the stimulus level to threshold, or comfortable, at any level as required. This method allows much faster patient testing.

When the necessary psychophysical information has been gathered, the audiologist uses the DPU to run a program to compile a "MAP" which contains the information needed for the speech processor to operate in its normal mode. This map contains data on which electrode to stimulate, and at what amplitude, for various combinations of F2 frequency and F2 amplitude, for the first speech processing strategy mentioned.

Before committing the information to the speech processor's memory however, the audiologist is able to talk to the patient using the patient's own speech processor via a temporary MAP stored in the DPU. It is possible to make changes to the MAP until it is decided that the information it contains will give the patient the best possible performance. When this has been done, the DPU is used to write the MAP into the speech processor's EPROM (eraseable, programmable, read-only-memory). The speech processor may then be unplugged from the DPU and operated independently from it.

We have also developed a device which enables functioning of the external speech processor to be monitored. This is essentially the electronics from an implantable receiver stimulator to which simple circuits have been added to reconvert the stimulus current outputs to an audio signal. In practice, the monitoring is done by placing the transmitter coil from the patient's WSP over the testing or monitoring device and listening on a pair of headphones. This is useful, as it quickly and easily verifies proper functioning of all components of the system external to the body, and we have found it to be an aid in finding suspected problems with the apparatus.

THE COCHLEAR IMPLANT IN USE

In use, the patient locates the coil unit and microphone behind the ear in a position directly over the implanted package. A distance of no greater than 10 mm between the exterior and interior coils has been found to be satisfactory. The speech processor may be placed in TEST mode to deliver a constant stimulus to aid coil positioning. Once the coil has been correctly positioned, the speech processor may be placed in RUN and used in its normal mode.

In RUN mode, if there is a period where the sound level is relatively constant, the WSP (Wearable Speech Processor) interprets this as background noise and disables the generation of stimulus pulses. This has the effect of reducing unnecessary and annoying stimulation due to background noise. In some situations, however, the patient may not find the background disturbing and may want to hear all of the signal. In these cases the SQUELCH OVERRIDE position may be used.

The WSP may be worn in a shirt pocket, holster or some other fitment to the clothing. The microphone is located on or near the ear and is of a highly directional type to allow the patient to focus his attention towards a particular speaker. Alternatively, a socket is provided into which a hand held microphone, radio or TV input may be plugged.

RECEIVER STIMULATOR (IMPLANT); GENERAL DESCRIPTION

Figure 5:
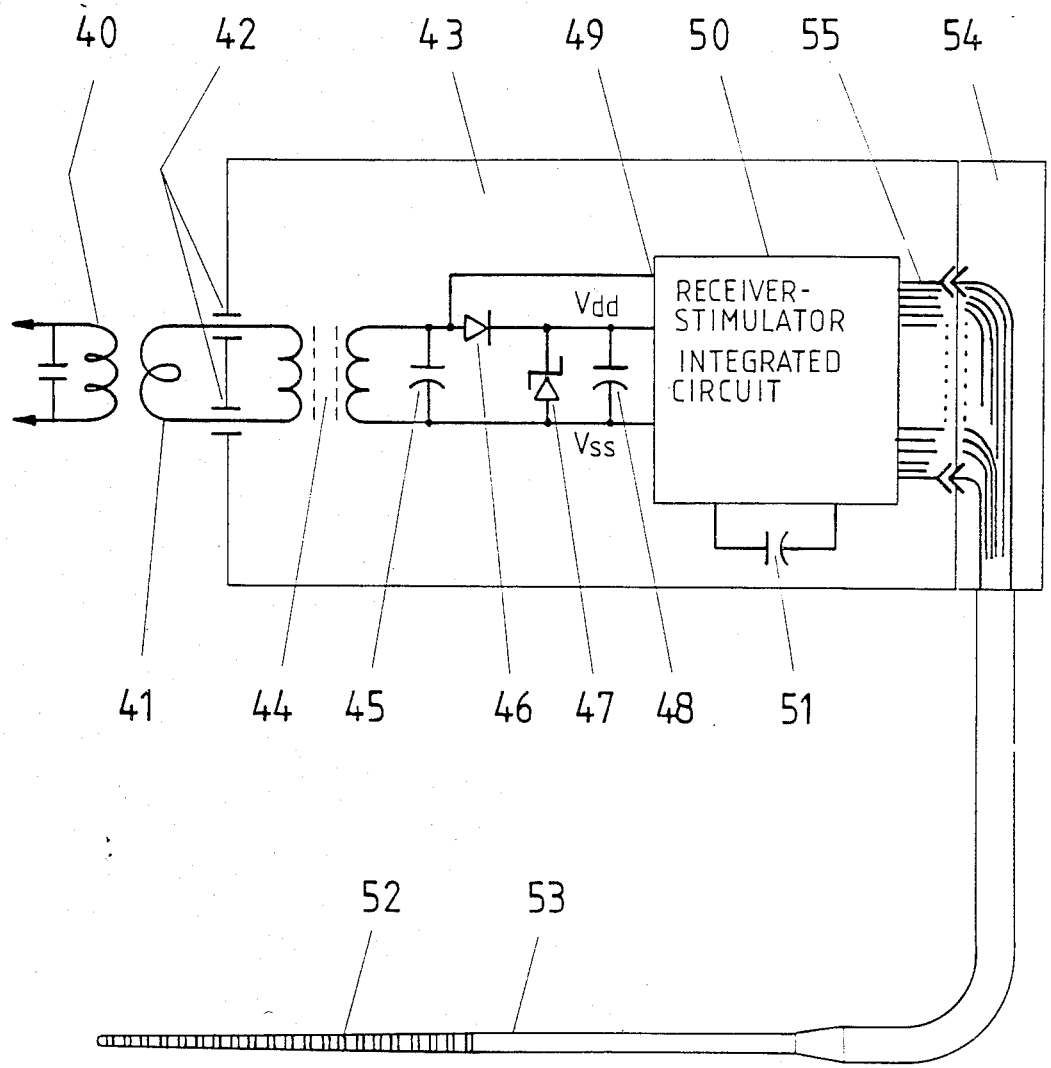
FIG. 5 is a block diagram of the body (ear) implantable receiver/stimulator.

A diagrammatic representation of the Receiver/Stimulator, or cochlear implant, is shown in FIG. 5. Power and data is from a single externally worn coil 40 approximately 30 mm in diameter, and wound from about 8 to 15 turns of insulated copper wire. This coil is driven from the externally worn WSP, and the information to be transmitted is encoded by the WSP from the incoming speech signal.

The power is received by a single turn platinum coil consisting of multiple strands of fine platinum wire wound together, and about 28 mm in diameter 41. Multistrand wire is used to improve the mechanical properties of the coil, and to reduce losses due to 'skin effect', which is significant in platinum at these frequencies. Both coils are "air" cored, that is, they do not make use of magnetic materials to function. This has an advantage over systems which do, in terms of bulk and weight savings.

While the transmitter coil has on the order of eight to fifteen turns to obtain the required inductance, the receiver coil, located inside the body has only one turn. This has the advantages that the single turn can be made very robust, insulation problems are greatly reduced and any electrical leakage to the surrounding tissues will be kept to a minimum due to the very low voltage present on the coil. The low voltage also has the effect that possible electrochemical effects on the coil itself will be kept to a minimum.

Electrical connection to this platinum receiving coil is made via two hermetic and insulated ceramic feedthroughs 42 into a titanium case 43. The design and method of manufacture of the implant package and feed-throughs has been described in the copending Kuzma application, No. 402,227.

The energy received by this coil is stepped up to a usable voltage level by a small transformer specially wound on a ferrite bead 44. The capacitor 45 in the secondary circuit of the transformer serves to tune the entire receiving circuit including the platinum coil and transformer. The transformer has a second function in that it isolates the receiver/stimulator circuit from the external coil. If this was not done, then the external coil could act as an extracochlear electrode, should there be an electrical current path to the surrounding tissue. Use of the transformer to electrically isolate the external coil allows the coil to be in direct contact with such tissue. In the embodiment described herein and the copending Kuzma application, the implantable package is encased in silicone rubber for protection, but electrical isolation and insulation does not depend upon the silicone rubber.

The voltage induced in the transformer secondary is rectified by a silicon diode 46, and filtered by a power supply filter capacitor 48. The performance of the power coupling system has been found to give adequate power transfer over a range of about 10 mm when the transmitter and receiver coils are coaxial and a degree of lateral misalignment is possible at distances less than this. Some measure of overvoltage protection is provided by the zener diode 47.

The coil/transformer is also connected through conductor 49 directly to the Receiver/Stimulator integrated circuit 50 for data recovery.

Because of the nature of the inductive coupling, it is possible that pulses at the start of stimulus bursts may be missed (i.i., not detected), and the inductive system may store sufficient energy to produce a few extra cycles of oscillation on the receiver side even when the transmitter has ceased sending energy. These effects mean that the number of detected pulses at the receiver may differ from the number of transmitted pulses by one or two pulses, and the information encoding strategy must take this into account.

Figure 1:
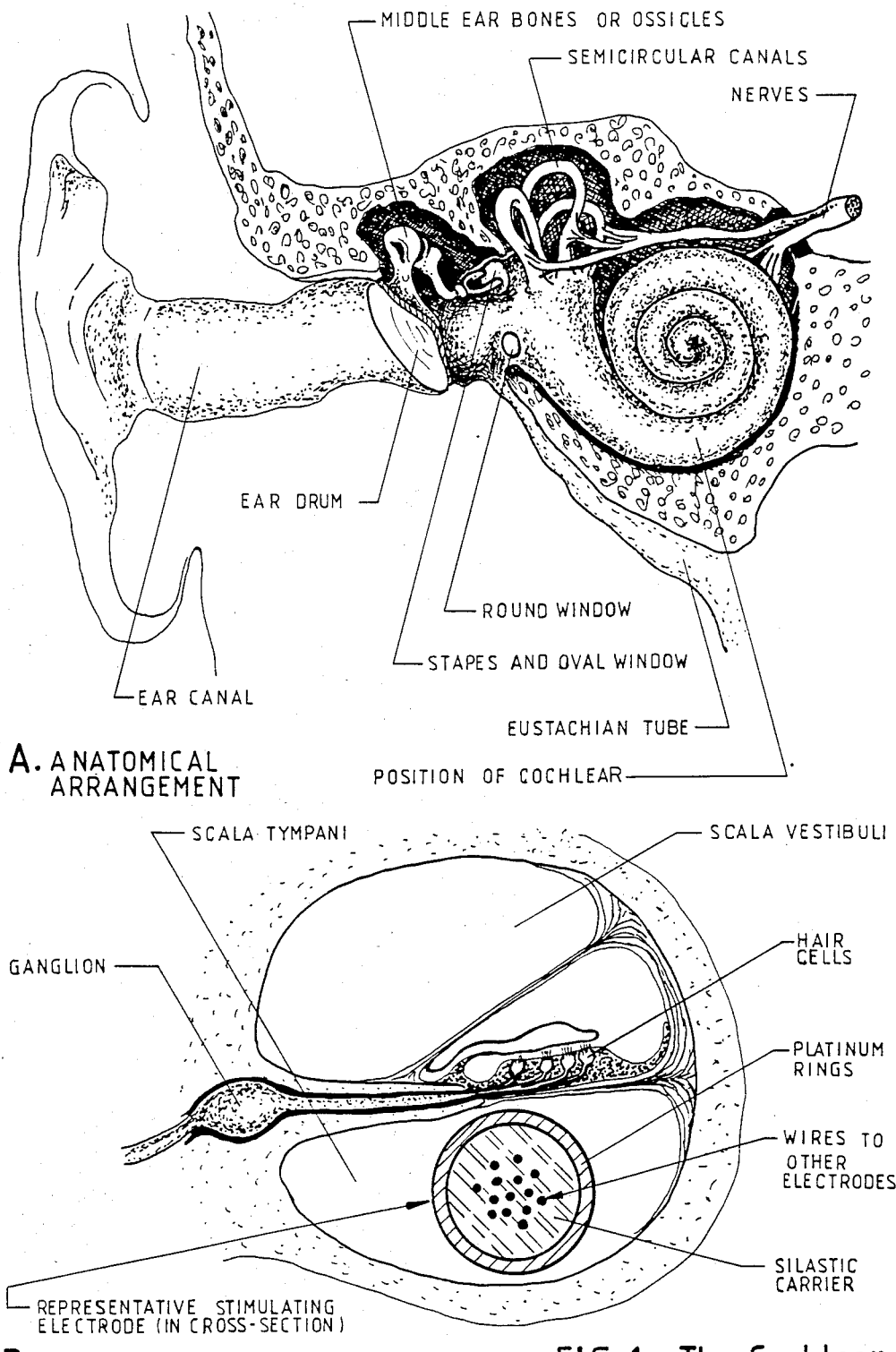
FIGS. 1A and 1B are interior views of the anatomy of the human ear and a cross-section of the cochlea, respectively.

An electrode array with platinum rings 52 (of which twenty-one are shown in FIG. 5) is implanted surgically into the scala tympani (FIG. 1B) in contact with the basilar membrane of the cochlea. The rings are embedded in a tapered carrier shaped to fit loosely in the decreasing cross-section of the scala tympani, and is inserted, for example, through an opening made in the round window membrane. The distance that the electrode will be able to be inserted will be different for each patient, and depends upon each patient's physiology, anatomy and aetiology of deafness. Typically, the electrode array can be inserted a distance of 17 to 22 mm. The electrode array is connected via a cable 53 to a connector 54 described in the previous Kuzma application. Connector 54 makes connection to the integrated circuit outputs 55 to provide stimulus currents of controlled amplitude and duration to the selected electrode.

In the embodiment described here, a separate rectifier diode and zener diode are used to provide power and protection for the implant. Alternatively, the rectifier diode and overvoltage protection may be incorporated in the receiver/stimulator IC itself. This has the obvious advantage of requiring fewer separate components inside the implant, with attendant possible reductions in size, and improvements in reliability.

STIMULUS CURRENT GENERATION

The method of generating the biphasic current pulse is illustrated diagrammatically in FIG. 6. In this diagram, Vdd is the most positive voltage in the RSU, and Vss is the most negative, or ground. Typically, Vdd is 11 Volts, with respect to Vss which is taken as zero volts.

The stimulus generation circuitry comprises a controllable current sink 60, where the current is determined by the data transmitted to the implant. Each of 22 electrodes (e.g., electrode number 3 shown as 61) may be connected either to the Vdd supply potential by switches labelled 'a' (e.g., 1a, 2a, 3a, etc.) or the controlled current sink by switches labelled 'b' (e.g., 1b, 2b, 3b, etc.). These switches are realized by enhancement mode MOS transistors, and are described in more detail in a later section. In A, no electrodes are connected to any active circuitry, and thus electrode potentials are 'floating'. This is the condition when the implant is unpowered.

In B, electrode number 2 (designated the Reference electrode) is connected to the positive supply by switch 2a being closed, and electrode number 3 (designated the Active electrode) is connected to the current sink by switch 3b being closed. Thus, current flows out of electrode 2, through the cochlear structures, and into electrode 3. The voltage across the electrodes is dependent upon the electrode impedances, but the amount of charge delivered is precisely known. This is phase 1, or phi 1.

In C, the connections are changed so that now electrode 2 is connected to the current sink, and electrode 3 is connected to the positive supply, so that the direction of current flow is exactly reversed. Since the current sink is the same for both phases, the current is identical in magnitude, but opposite in sign. Thus, if the time of current flow is the same for both phases, then the amount of charge delivered in phase 1 is equal to that in phases 2, and the net DC charge delivered is zero.

In the bipolar configuration, two electrodes only are connected to the current sink and all other electrodes are left open circuited. For simple bipolar operation adjacent electrodes are selected as Active and Reference, although any pair of electrodes may be selected as Active and Reference. Thus, bipolar electrodes may be separated by any desired distance, up to the length of the array. This capability provides the advantage of selecting an alternative electrode if the adjacent electrode is unsuitable, or the possibility of utilizing different stimulation strategies which may become identified in the future. In addition, it is possible to select the Active electrode numerically preceding, or following the Reference electrode to allow the capability to control the order of current flow in the electrodes.

The other mode of stimulation uses the 'common ground' or 'multipolar' electrode configuration, and is illustrated in FIG. 7. In this mode, one electrode is stimulated against all the other electrodes which are connected together. That is, in phase 1 (FIG, 7A), electrode 2 is connected to the current sink, and all other electrodes connected to the positive supply. Thus current is sunk by electrode 2, and sourced by all other electrodes. The current distribution between the common ground electrodes is dependent upon a number of factors, including (predominantly) electrode impedance.

In phase 2, the connections are changed, as shown in FIG. 7B, so that the Active electrode is now connected to Vdd, and all other electrodes are connected to the current sink. Thus, the current in the Active electrode (electrode 2 in this case) is the controlled biphasic current pulse. The other electrodes will have current waveforms which are also biphasic, but of lower amplitude, since the return current is shared between all other electrodes. A wider spread of current in the cochlea is thus produced by this configuration.

Between stimuli, and while the implant is powered, all electrodes are connected to Vdd by closing the 'a' switches and opening the 'b' switches in FIG. 6. Thus, since all electrodes are shorted together, any residual electrode polorization will be dissipated. Charge imbalance could occur, for example, if phi 1 were not equal to phi 2, such as might occur if a different number of data pulses were received by the RSU for the phi 1 and phi 2 times due to coil coupling variations. If this were the case, if the electrodes were not connected together between stimuli, then the electrodes could end up polarized after stimulation and, over a period of years, corrosion of electrodes could occur. Corrosion of electrodes can adversely affect the performance of the electrode, and may result in toxic corrosion products remaining in the cochlea. Polarization of all electrodes relative to the body is not theoretically possible because the system is closed. It can be seen that the maintenance of charge balance between electrodes is also done without the need for output capacitors, as mentioned previously.

The advantage of having a number of possible modes of stimulation is that the most natural sounding percepts or those having the highest intelligibility may be selected once the patient has been implanted, rather than having to make this decision beforehand.

DATA TRANSMISSION FORMAT

The power/data link comprises two magnetically linked inductors, having a coefficient of coupling which depends on the placement of the external primary coil relative to the implanted secondary. Data is transmitted by controlling the number of cycles of excitation to the transmitter coil, which is heavily damped between bursts of pulses. At the receiver, the data signal energy is used for stimulation and also to provide power for the stimulator electronics.

Digital data is encoded in the number of cycles in a burst, while analog functions are directly controlled by the duration of the burst. At the receiver, both the number of pulses detected and the received burst length depend on the coupling between coils. Tests using the coil configuration described below have shown a difference between transmitted and received pulse counts of one and occasionally two pulses, depending on coil position. Thus, a method of coding digital data is used which is tolerant to error counts of at least three pulses.

At the transmitter, the number N which is to be transmitted, is encoded as the burst length 8N+4 pulses, while the receiver divides the received pulse count by eight in its decoding process. This process is summarized in the following table for the first few integers:

| Integer | Encoded Length | Decoder range (no error) |
|---------|----------------|--------------------------|
| 0       | 4              | 1–7                      |
| 1       | 12             | 8–15                     |
| 2       | 20             | 16–23                    |
| 3       | 28             | 24–31                    |

| Integer | Encoded Length | Decoder range (no error) |
|---|---|---|
| 4 | 36 | 32–39 |

FIG. 8 shows the format of the data transmission to the implant. Each time a stimulus is required, a data frame comprising six bursts of pulses at a pulse rate of 2.5 MHz is transmitted. This frequency of transmission was selected to allow presentation of stimuli in excess of 1 kHz, but it is understood that alternative embodiments using different frequencies would be within the spirit of this invention. The data coding described above provides a robust, self-clocking data format without requiring elaborate error checking. This is in contrast to other systems in which the data is digitally encoded, where the addition or loss of one or two pulses can produce a gross error.

The choice of transmission frequency depends upon a number of factors. Firstly, in order to inductively couple power through body tissues for any reasonable distance, low frequencies (preferably less than a few tens of MHz) are desirable. At frequencies in excess of 10 MHz or so, it is not possible to efficiently transfer the power required. Low frequencies are typically used in pacemaker prior art for coupling information (and sometimes power) into a pacemaker encased in a metal package, and a frequency of 16 KHz may be used. At frequencies greater than about 50 KHz it is not possible to couple power into a metal container with acceptable efficiency, and receiver coils must be exterior to the container, as is used in this embodiment. Alternative packaging technologies which did not use metal would allow transfer of power to a receiver coil inside the package at higher frequencies. For the coding system described above, and for any other coding system which could be used to transfer the equivalent amount of information at the same rates, the minimum frequency which could be used is determined by the information transfer rate of the channel, at the times it is in use (i.e., in order to deliver a stimulus pulse with minimum delay). Finally, the technology which has been chosen for other reasons is CMOS, and contemporary CMOS technology has reliable operating frequencies of only a few MHz. Of course, it would be possible to use a modulation-demodulation scheme (such as FSK, FM or phase encoding) at a higher frequency to transmit the information, but this would merely add complexity for no advantage.

Sequential pulse bursts must be separated by at least a sufficient interval to allow the 'end of burst' to be detected: an interburst interval of 20 clock periods is used, and the system is designed to be tolerant of interburst intervals in excess of this time. This feature offers an advantage in that a constant time interval may be allocated for each stimulus frame, and thus there will be no jitter between stimulus pulses on different electrodes. Otherwise, encoded frames would be of different lengths, and thus the stimulus time relative to the start of the frame would vary with encoded data.

The stimulator circuit has six possible states (S0 to S5), and the detection of the end of each burst is used to change the circuit state to the next sequential state. These states are also shown on FIG. 8. A uniquely defined burst (the SYNC burst, for which N=0) is used to reset the system.

SYNC BURST

The SYNC burst is sent at the start of the frame to reset the system state to state S0. The received burst length must be less than 8 pulses, and a transmitted burst length of 4 pulses is preferred.

ELECTRODE SELECTION

The Active electrode is selected by the number decoded from the second burst. For example, electrode 5 is selected as the Active electrode if the number 5 is decoded from the second burst.

MODE SELECT

There are two basic stimulation modes possible as described, Bipolar and Multipolar. With bipolar stimulation, however, the reference electrode may be selected from any of the remaining, i.e., not active, electrodes. The number decoded from the third, or mode select, burst is used to define the reference electrode as detailed herein. This number is described as the Stimulation Mode. For multipolar stimulation where an Active electrode is stimulated against all other electrodes connected together, Mode=1.

For bipolar stimulation the Reference electrode number is equal to the Active electrode number + (Mode−1). For example, if the Active electrode is 6 and Mode=4, then the Reference electrode is 6+4−1=9. With this arrangement, it would appear that the Active electrode number must always be lower than the Reference electrode. If, however, the selected Reference electrode number exceeds 22 then the actual Reference electrode will be that selected minus 22, for example:
Active electrode=10
Mode=15
Reference electrode use=(10+15=25) −22=3

CURRENT AMPLITUDE CONTROL

The amplitude of the output current is determined by the duration of the amplitude burst. This burst has a minimum length of 16 pulses, which produces the maximum stimulus current of about 1 mA, and the amplitude is reduced in steps of about 3% for every 400 nS increase in burst duration. This is the increase in burst duration caused by adding a single cycle of that period in the burst. The relationship between perceptual loudness and stimulus amplitude is also logarithmic, allowing best use of the current steps available.

This approach of reducing amplitude with increasing burst length was preferred over the alternative of increasing amplitude with duration since it defines the maximum stimulus which can be delivered. Further, because sensations of equal loudness may be elicited by stimuli of approximately equal charge, this approach allows use of maximum stimulus rates to be investigated using high amplitude short duration stimuli.

Although the current amplitude is not coded numerically to eliminate the effects of coupling variations (like the electrode selection pulse burst), it can be seen that an error of one or two received pulses will result in only a small error in the stimulation current.

PULSE DURATION CONTROL

The durations of the two phases of the stimulation pulse, phase 1 and phase 2 as shown in FIG. 4, are determined directly by the duration of the two stimulation bursts. Since each burst is an integral number of transmission cycles (each of duration 400nS for a 2.5

MHz transmission frequency), then the pulse duration can be adjusted in steps of 400nS. With the existing speech processor encoder, the maximum length of a stimulation burst is 1022 pulses, or 408.8 microseconds. However, there is nothing in the receiver circuitry itself to prevent use of longer bursts, if this is required. In normal use the durations of the two stimulus phases are equal, but they are set independently and may be different if so desired.

FUNCTIONAL DESCRIPTION

The receiver/stimulator embodiment described below uses standard and conventional metal gate CMOS technology, with the circuits being realized using a gate array sometimes known as an uncommitted logic array available from AMI, TI, IMI, LSI, Logic and Motorola. Logic arrays in general are available from a number of suppliers such as those listed. The particular logic array used is available from AWA Microelectronics and none of the suppliers listed. Many design features may also be realized using alternative technologies and techniques, for example, silicon gate technology and standard cell design philosophy, and such alternative embodiments are understood to be within the spirit of this invention.

The gate array used in this embodiment comprises some 2000 n and p channel enhancement mode devices of similar dimensions in a central array, and additional devices located around the perimeter of the circiut.

For a single N channel array device having a threshold of Vthn, the drain current at sufficient drain source voltage (Vds) is given (in the strong inversion region) by the expression:

$$Ids = Kn * ((Vgs - Vthn)^2)$$

While for two devices connected in series, with a common gate connection, $$Ids = (Kn/2) * ((Vgs - Vthn)^2)),$$

and for two parallel devices $$Ids\ (2*Kn) * ((Vgs - Vthn)^2)$$

The convention used in this description is to define a single array device as a "IX" device, two devices in series as a "½X" device, two devices in parallel as a "2X" device, and so on, since this is how their drain currents are related for equal Vgs. This convention applies to connections of any number of devices.

Typically, $Kp = 10$ uA/$(V^2)$ and $Kn = 20$ uA/$(V^2)$ for array devices.

The peripheral devices include buffer transistors for which $Kpb = Kbn = 500$ uA/$(V^2)$. Single, series or parallel connections of these devices are indicated by B, ½B and 2B. The perimeter also includes "long" devices of low transconductance, typically $Kpl = Knl = 0.15$ uA/$(V^2)$. In addition area two zener diodes located on the periphery.

FUNCTIONAL DESCRIPTION OF DIGITAL CIRCUITS

The stimulator integrated circuit contains both digital and analog circuit functions.

A block diagram of the digital circuitry is shown in FIG. 9. Received signal energy from the tuned transformer 400, 401 is rectified by the diode 402 and used to power the circuit. A filter capacitor 403 maintains the supply voltage between data frames. The Burst Detector and Burst Clock Extraction circuit 404 is used to detect when a signal is present, and to recover a clock signal from the data signal 405, taken directly from the tuned circuit. The envelop detector output BURST 407 is asserted during signal bursts, while a threshold detector generates the CLOCK signal 406 from the unrectified signal input.

The CLOCK signal is fed to the Prescaler and Sync Detector circuit 408 which has three functions. First, it carries out the divide by eight operation required to decode digital data and generate CLOCK8 409. Second, it asserts SYNC 412 for signal bursts of less than eight pulses, and third, it asserts BURST16 during the time for which a burst exceeds 16 clock cycles in length. BURST16 output 410 is used to control various analog functions as described below.

At the heart of the circuit is the State Counter 422. It has six outputs S0–S5 (423–427, 420) which control the overall operation of the circuit. Only one output can be asserted at any time, and thus the system State is defined at any time as the output asserted at that time.

In normal operation, the State Counter is left in State S5 between data frames, and the SYNC burst 412 generates a RESET 419 signal which sets the system State to S0. The State Counter is incremented through to S5 during the remainder of the frame by DATA signal 418, which is asserted at the end of every data (that is, not SYNC) signal burst.

DATA and RESET are generated by the Error Detector circuit 415 which also detects if a DATA burst is received when in state S5, or if a SYNC burst occurs in a state other than S5. These are error conditions, and stimulation is inhibited through assertion of the INHIBIT signal 421. INHIBIT is also asserted under two other conditions related to the level of the supply voltage. These conditions are detected by analog sections of the circuit and signalled by assertion of VLOW 416 and VLOGIC 417. VLOW is asserted if the supply voltage at the start of the first stimulus phase is less than the voltage required for sufficient voltage compliance for the output current source, while VLOGIC is asserted if the supply voltage falls so low that there may be possible loss of data. INHIBIT is reset by a subsequent SYNC burst, received when in state S5.

The Electrode Counter 428 is reset by the signal S5 420 and incremented during State S0 as described below. At the end of S0 its value is latched in the Active electrode latch 31, having 22 outputs A1–A22, shown as 430. During S1 the counter 428 may be further incremented and its output is used directly to select the Reference electrode outputs R1–R22, shown as 429.

The Mode gate 413 applies the CLOCK8 signal 409 directly to the Electrode Counter during state S0, while during state S1 the initial CLOCK8 pulse is gated out. The signal BIPOLAR 414 is asserted if the Mode burst generates two or more CLOCK8 clock pulses. When Mode=1, in the multipolar mode, a single CLOCK8 pulse will be generated during the MODE burst, the Active electrode will always be the same as the Reference electrode and BIPOLAR will not be asserted, while for bipolar operation the Active and Reference electrodes will be different. The counter used in the Electrode Counter circuit is cyclic, that is the next count after 22 is 1, thus enabling the Reference electrode number to be selected as lower than the Active electrode.

Combinational logic is used to derive the signal STIM 411, which is asserted during both state S3 and state S4, provided that BURSTI6 is asserted. The Active and Reference electrode select signals AN and RN are asserted only if STIM is asserted and INHIBIT 421 is not asserted.

FUNCTIONAL DESCRIPTION OF ANALOG CIRCUITS

A block diagram of the analog circuit functions is shown in FIG. 10.

The Supply Voltage Monitor 250 asserts the digital signals VLOW 416 and VLOGIC 417 under the conditions described above, while VHIGH 251 is asserted if the supply voltage exceeds a preset limit. VHIGH is used to control the Shunt Regulator circuit 252, and typically limits the maximum supply voltage to 2.0 volt above the VLOW value.

The Reference Current Generator 253 produces the current Ir 261 which will vary from device to device as a result of manufacturing process variations. The Current Trim Network 254 is then used to set Iref to within 10 percent of its nominal value of 1 uA. Trimming is carried out by connecting the inputs A, B and C (255, 256, 257) to Vss or Vdd as required.

The amplitude of the output current Io 260 of the Programmable Current Source 259 is set by the duration of the amplitude burst, as expressed by the approximate relationship $$Io = Imax*\exp(-k*t)\text{mA, where typically } Imax = 2.0 \text{ mA}$$
$$k = 0.1$$

for $t$ = amp burst length (in usec)

The output stage of this current source 259 has an output impedance exceeding 1 Megohm. The current source is connected to the selected electrode through the selected Output Switching Networks (261 for example) during S3 and S4, as described below.

During intervals between data frames, when the circuit is in state S5, all analog circuits except the Reference Current Generator and Supply Voltage Monitor are shut down. The digital circuitry draws only leakage current, and the total circuit current drain is less than 5 microamp.

The power supply capacitor is chosen to be as large as possible to maintain the supply voltage above the VLOW level for as long as possible in the absence of incoming data signals, while being sufficiently small in value to enable VDD to be raised above VLOW in as few stimulus frames as possible when starting from VDD=0. Too large a capacitor will result in missing stimuli at the start of a stimulus sequence (e.g., a sequence drived from a speech utterance), while too small a capacitor will result in lost stimuli because the receiver/stimulator is unable to maintain Vdd above Vlogic between adjacent frames of the same stimulus sequence. In the operation of the power supply, the charge on the power supply capacitor does decay between stimuli, whether caused by a speech input or other signal source. It is for this reason that it is important to minimize the power consumption of the circuit between stimuli.

We have found that the best value for the power supply filter capacitor with our circuit realization is 0.5 microfarad, which allows an interstimulus interval of at least 200 mS (for VHIGH−VLOW=2 volt) before the next stimulus may be inhibited due to VDD falling below VLOW. In practice, it has been observed that with normal speech derived inputs this interval is rarely exceeded. With this value of CS, up to 5–10 stimulus frames may be required for precharging at maximum coil separation: again, this brief delay is not perceived by implanted subjects.

DETAILED CIRCUIT DESCRIPTION

Much of the design of the receiver/stimulator circuit uses conventional techniques as well known in the art. However, the stimulator contains a number of novel features, which are described here in detail.

BURST DETECTOR AND CLOCK EXTRACTION CIRCUIT

The Burst Detector and Clock Extraction circuit is shown in FIG. 11. The unrectified input signal 281 is applied, through the standard input protection network 282, to the inverter formed by devices 283 and 284. The characteristics of these devices are chosen so that the inverter threshold is set to 70-80% of VDD, increasing tolerance to ringing in the receiver circuits at the end of bursts. Inverter 285 restores signal polarity, and the buffer 286 distributes the signal CLOCK 293, which is asserted when the input signal is above threshold. The inverter 287 turns on the P channel device 288 when CLOCK is asserted, forcing the node DET 290 high. The constant current sink 291 is used to discharge the nodal capacitance of DET To Vss in the absence of the signal CLOCK. The magnitude of this discharge current is selected to pull DET below the following Schmitt trigger 292 threshold if CLOCK is not asserted for more than 3–5 microseconds. The Schmitt trigger provides noise-free operation, even for this relatively slow transition of the DET node.

REFERENCE CURRENT GENERATOR

The function of the Reference Current Generator is to provide a stable reference current without the need for any external components. It is also required that the current consumption is low, as this circuit is not disabled during state S5, when the circuit is unpowered.

The basic circuit is shown in FIG. 12. A current mirror is formed by devices 301 and 304, which share the same Vgs. Since the K value for device 301 is four times that of device 304, $$I1 = 4* I2$$

Devices 300 and 303 are both "long P" devices, and have similar K values, Klp, and threshold voltages Vthlp. The device 302 is an N channel peripheral device having its drain and P well connected to Vdd, its gate to Vss, and its source to device 303. So connected, it behaves as the bipolar npn device depicted in FIG. 12. The voltage drop across device 302 will be one Vbe.

Suppose device 303 has the gate to source voltage Vgs303 which exceeds the device threshold voltage by Vd, then $$Vgs303 = Vthlp + Vd$$

then $I2 = Klp*((Vgs303 - Vthlp)\,\hat{}\, 2)$ $$= Klp*(Vd\,\hat{}\, 2)$$

For device (300),

-continued
$$Vgs300 = Vgs303 + Vbe$$
$$= Vthlp + Vd + Vbe$$
Thus $I1 = Klp*((Vd + Vbe)^2)$ Since $I1 = 4 * I2$, then either Vd=Vbe, or $I1=I2=0$. That is, the circuit has two stable operating points, either zero current or $$I1 = 4 * Klpl * Vbe^2$$
$$I2 = K1p * Vbe^2$$

With the incorporation of appropriate startup circuitry the zero current operating point can be avoided, and then $$Ir = I1 = 4 * Klpl * Vbe^2$$

The voltage drop Vbe is well defined by the manufacturing process, as are all K value ratios. The dominant cause of variability in Ir is thus the spread in absolute value of Klp to be expected during manufacture. Typically, this will vary across devices by up to 2:1 and it is this variability which required the use of the Current Trim Network.

Those skilled in the art will recognize that sensitivity of this circuit to power supply variations may readily be improved by using cascode configurations for devices 300 and 304.

The value of Ir may be varied by either changing the relative K values for devices 301, 304, 305 or by changing the excess drive to device 300 from the value of one Vbe shown here.

Figures 23A, 23B:
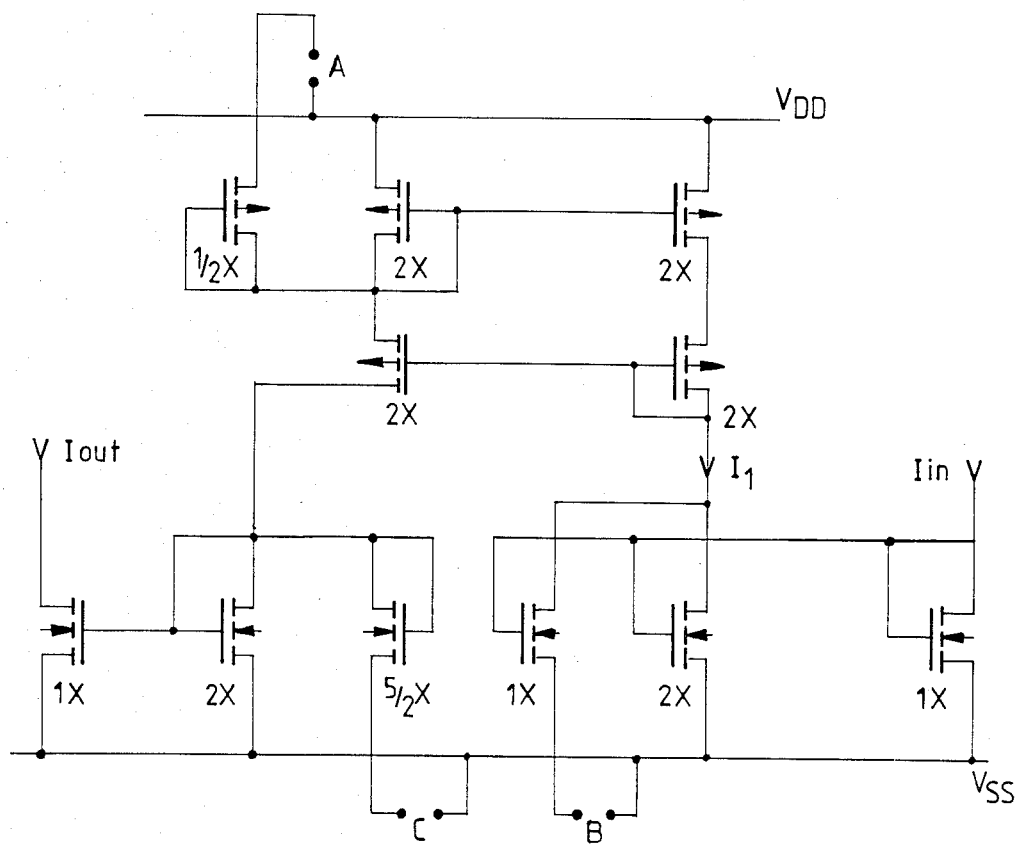
FIG. 23a is a circuit diagram of the current trim network and FIG. 23b illustrates the nominal transfer function as a function of the external trim connections.

The current trim network 254 is shown in full in FIG. 23a. It comprises a series of variable ratio current mirrors, where the ratios and thus the overall current transfer function of the network may be adjusted using external connections to Vss or Vdd. The table in FIG. 23b illustrates the nominal transfer function as a function of the external trim connections. With this circuit no external components are required to trim the reference current source.

The operation of the circuit is illustrated by considering the effect of closing contacts B. With B open, $I1=2 * Iin$, while with B closed $I1=3 * Iin$. With B open, he transfer ratio is nominally 1.0, while it is 1.5 with B closed. Closing contacts A serves to increase the current transfer ratio by a factor of 1.25, while closing contacts C changes it by a factor of 0.444.

PROGRAMMABLE CURRENT SOURCE

The Programmable Current Source circuit is described in two parts: the Programmable Current Generator, and its associated Output Mirror. The circuit of the Programmable Current Generator is shown in FIG. 13 with circuit timing in FIG. 14, while the circuit and timing of the Output Mirror is shown in FIG. 15.

The principles of operation of the Programmable Current Generator are easily understood by considering a large enhancement mode transistor which has its gate voltage adjusted such that it is operating in the subthreshold region, where the Ids to Vgs relationship is dominantly exponential. The Ids of this device is appropriately multiplied through the use of current mirrors to become the output current. A capacitor, called the SHC capacitor, is connected between gate and source, and charged to the Vgs voltage. A current sink is now connected to discharge this capacitor. If the capacitor is discharged at a constant rate, then Vgs will decrease linearly and the output current will decrease exponentially with time. The final output current will be defined by the time for which the SHC capacitor is discharged.

In FIG. 13, the large device described above is 334, and the capacitor SHC is connected between the node SHC and Vdd. Node SHC is discharged through the current mirror formed by devices 335, 336 and 337, provided that S2 and BURSTI6 are asserted, when TD is asserted and device 335 is turned off. The rate of discharge is nominally 24 uA, being Iref=1 uA multiplied by two in the current mirror 320, 342 and again by twelve in the mirror 336, 337. The SHC capacitor is discharged only during state S2, BURSTI6 asserted.

The SHC capacitor is charged during states S0, S1 and the duration of S2 for which BURST is not asserted. During this time the combinational logic 339, 340, 341 and 346 asserts the signals TREF 343 and TREFN ((344), active low), turning on devices 332, 329 and 331. The current mirror 342, 321 generates the current Iref of approximately 5 uA, and the feedback circuit comprising the current source 332 and the controlled current sink 330 charges the SHC capacitor such that Ids of 334 is equal to Iref. Device 333 is used to cascode device 334. The stability of the feedback loop is assured by the addition of resistor 348 to provide phase compensation.

During states S3 and S4, after partial discharge of the SHC capacitor has occurred, device 322 is turned off and devices 326 and 324 are turned on. Ids from device 334 is multiplied by a factor of about 50 by the mirrow 323, 327 and again by another factor of two by a cascoded arrangement of large P channel devices 328. The current Ipr, having a maximum value of 0.5 mA is further multiplied by a factor of four by the Output Mirror.

During S5, Iref=0 and device 324 is turned off, reducing current consumption of this area of circuitry to the leakage value. The P channel devices 338 and 341 limit the drift of the SHC node during this time.

The output mirror (FIG. 15) is enabled during S3 and S4 provided BURSTI6 is asserted. Under these conditions device 314 is turned off and the transmission gate 313 is turned on. A transmission gate is a p channel device connected in parallel with an n channel device—gate to gate, source to source, drain to drain. The current mirror formed by devices 310 and 311 (FIG. 15) defines the magnitude of the output current Io as four times the magnitude of the input current Ipr, while device 312 is used to cascode device 310. The output impedance of this current mirror is very high, even for large output currents, being in excess of 1 Megohm for an output current of 2 mA.

When the output stage is not enabled, the output node is clamped to Vdd by device 315. The initial conditions for this node are thus the same at the start of each output phase, improving the charge balance for equal amplitude, equal duration output pulses.

Device 314 keeps device 312 turned off when the circuit is not enabled and the transmission gate 313 is open.

OUTPUT SWITCHING CIRCUIT

The receiver/stimulator contains 22 Output Switching circuits, one for each electrode output. The schematic for one such circuit is shown in FIG. 16: it connects the output to Vdd if the signal S5 is asserted, and to Vdd or the Programmable Current Source, if selected by the control inputs An 368, Rn 369 and BIPOLAR 370. The signal S3 is used to control the multiplexer 362, directing the An input to the NOR gate 366 during state S3 and device 363 during state S4, and making the opposite connection for the output from NOR gate 361.

During state S5, signal S5 is asserted, and the output of NOR gate 366 is forced low, turning on device 363 and connecting the output to Vdd. At this time all outputs are connected together.

If this output is selected as the Active electrode, then An is asserted during states S3 and S4. When S3 is asserted during state S3 device 364 is on, connecting the output to the current sink, while when S4 is asserted during S4, An is connected to the input of NOR gate 366, forcing its output low and connecting the output to Vdd.

If the output is selected as the Reference electrode (Bipolar mode) then the electrode is connected to VDD when S3 is asserted and to the current sink when S4 is asserted.

For multipolar operation BIPOLAR is not asserted, and either An and Rn are both asserted (for the Active electrode) or neither are asserted (for all other electrodes). If An is asserted, circuit operation is as for the Active electrode (Bipolar mode) described above, with the AND gate 361 being disabled. Otherwise, the output of AND gate 361 is high, and the output node will be connected as described for the Reference electrode (Bipolar mode).

In FIG. 16 the signals An, Rn and BIPOLAR are asserted only during S3 and S4. The signal S4 is thus not required as an explicit input to the Output Circuit. The state map for the output Output Switching Circuit, together with explanatory notes is shown below.

| An (see Note 1) | Rn | BI-POLAR | S3 | S5 | OUTPUT CONNECTIONS | (see note 2) |
| --- | --- | --- | --- | --- | --- | --- |
| 0 | 0 | 0 | 0 | 1 | Vdd and Io | |
| 1 | 0 | 1 | 0 | 0 | Vdd | BIPOLAR |
| 1 | 0 | 1 | 1 | 0 | Io | BIPOLAR |
| 0 | 1 | 1 | 0 | 0 | Io | BIPOLAR |
| 0 | 1 | 1 | 1 | 0 | Vdd | BIPOLAR |
| 0 | 0 | 0 | 0 | 0 | Io | MULTI-POLAR |
| 0 | 0 | 0 | 1 | 0 | Vdd | MULTI-POLAR |
| 1 | 0 | 0 | 0 | 0 | Vdd | MULTI-POLAR |
| 1 | 0 | 0 | 1 | 0 | Io | MULTI-POLAR |

Figure 24:
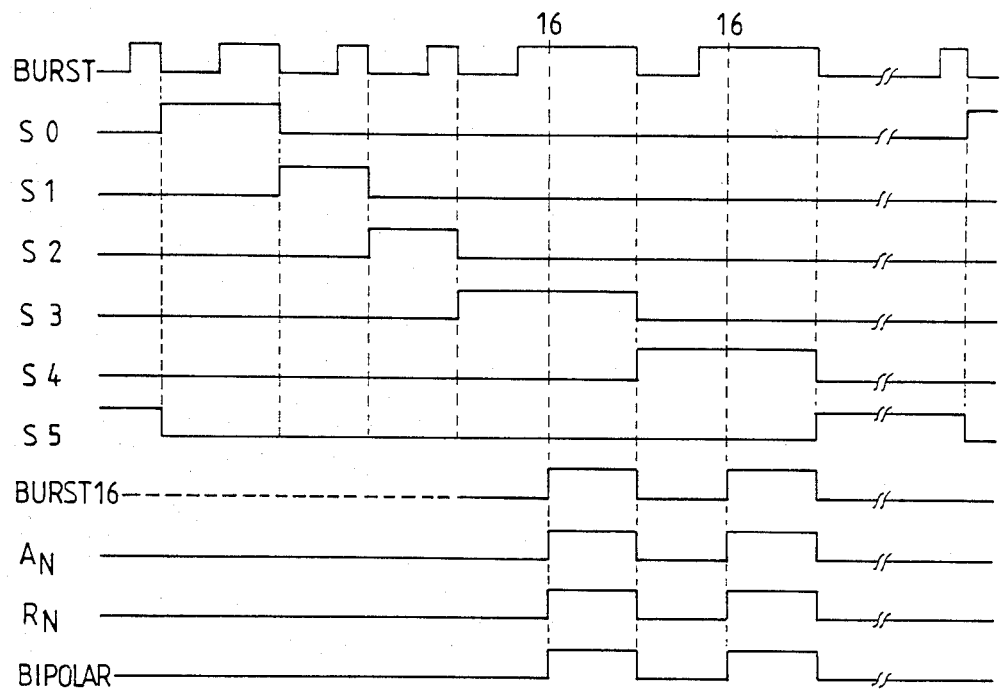
FIG. 24 illustrates the state and output timing of the output switching circuit.

Note 1
An and Rn are asserted only during S3 and S4, provided the BURST16 is asserted.
Note 2
When BIPOLAR is not asserted and An is not asserted, then for S3 not asserted the multiplexer will set the gate of device 364 to high. Device 364 will be on only when S4 and BURST16 are asserted, when the Output Current mirror is enabled and the voltage on the Io line is more than a threshold below Vdd (see FIG. 15). Otherwise, the Io line is held at Vdd and device 364 is off.
All state signal (S0–S5) are generated by the State Counter (422 FIG. 9), at the times indicated in FIG. 8, and as indicated in FIG. 24. This Figure also show the timing of the output control signals An, Rn and BIPOLAR.

WEARABLE SPEECH PROCESSOR (WSP)

The function of the Wearable Speech Processor is to accept an incoming acoustic signal from a microphone, and after suitable processing, send the appropriate stimulation frames to the implanted Receiver Stimulator Unit in the patient. The WSP must be small, light, and low power, as it is intended that the WSP be worn on the body, e.g., in a shirt pocket, and be battery powered. Power consumption must be minimized to achieve longest possible time between change of battery, or recharging. The WSP must also be able to be configured for each patient's unique characteristics of psychophysics.

A block diagram of the speech processor is shown in FIG. 17. A microphone 80 receives the acoustic input. This microphone may be a conventional hearing aid microphone, for example worn over the ear on a hook, or may be a higher quality studio type microphone, or the microphone may be replaced with another signal source such as the audio output from a television or radio. This flexibility of choice of input has advantages for the implant patient.

The main aim of the WSP design is to provide the user with speech communication, and the stimulation strategy and description of terms reflects this. However, it is also important to provide the user with awareness of environmental sounds, and the stimulation strategy makes this possible also, although it is optimized for speech communications. In addition, it is possible to select the most appropriate strategy for each patient from a set of possibilities.

The audio signal is amplified and processed by the WSP front end 81. From this, three signals are produced:
  START used to start the generation of a stimulus pulse frame by the encoder
  ELSEL a voltage used to determine which electrode is to be selected for stimulation
  STAMP a voltage used to determine the amplitude of stimulation on the selected electrode.

The START signal is used to initiate a single stimulus frame of pulse bursts by the Speech Processor Encoder 82 each time it occurs. The ELSEL and STAMP signals are used to determine stimulus parameters of electrode and stimulus level, according to which of the speech processing strategies previously described has been selected. An alternative speech processing strategy based on F1 is also possible using the invention described here.

An 8 bit Analog to Digital Convertor 83 ("ADC") converts the ELSEL and STAMP signals into numbers for use by the encoder. A two input analog multiplexer and sample and hold circuit 92 is under control of the encoder (for signal selection) and the ADC chip (for S/H control) so that the correct signal is presented to the ADC at the correct time. The encoder operates by way of a program stored in a UV erasable PROM 84, which also stores the map between F2 and electrode, and A2 and amplitude of stimulation, for each electrode. The stimulation amplitude is related to STAMP differently for each electrode, according to stimulation thresholds for that electrode.

These three signals are derived from five basic signals produced inside the WSP front end. It is possible to configure each patient's speech processor to select which of two or three alternative stimulation strategies is to be used, and thus which set of three signals from the following six is to be used. The five basic signals are:
  Fo the voicing or fundamental frequency
  Fo' the frequency translated Fo signal
  F2 a voltage proportional to F2 frequency
  A2 a voltage proportional to amplitude of the F2 signal
  F1 a pulse train at the frequency of the dominant spectral peak (F1)

A the overall acoustic signal amplitude.

Data from the front end are encoded by the encoder chip into the format shown in FIG. 8, and described herein, and to the output stage 85, which is connected via a coaxial cable 86 to the transmitting coil 87. The transmitting coil is tuned to the correct frequency with a single capacitor 88 located at the coil.

A connector 89 in the WSP allows connection to the Interface Unit, or IU, which is used during the testing of the patient, and allows the parameters to be programmed into the patient's map in the WSP.

The WSP is powered from +5V and −5V supplies generated by a DC-DC Convertor 90 operating from batteries 91. Battery voltage may be in the range 3 to 7 volts, allowing a wide choice in number and style of batteries, including readily available primary cells, or rechargeable cells.

The speech processor is constructed in a small case designed for easy carrying in a pocket, on a belt, or in a pouch under the clothing. The cable from the microphone and the coil on the ear attaches to the WSP by a connector for ease of use.

WEARABLE SPEECH PROCESSOR FRONT END

Overview

To understand the speech processor front end it is first necessary to be aware of the nature of the speech signal. Speech may be divided into two categories: voiced and unvoiced. Voiced speech is produced by a vibration of the glottis which provides an excitation source for a resonant system consisting of the oral and nasal cavities. A number of resonances (formants) are produced but of these the three lowest contain most of the information.

Unvoiced speech does not use the glottis as an excitation source but rather a noise produced by the passage of air such as between the tongue and teeth (as in 's' and 'th' and 'f'), or by explosive generatin of sound pulses (such as in 'p' and 't'), or by the passage of air in the throat such as 'h').

The WSP is designed to use one of two stimulation strategies, employing sets of three parameter estimates of the acoustic input, as follows:

STRATEGY 1

(a) The frequency of the second formant (resonant frequency) (F2) is encoded into electrode position/selection.

(b) The frequency of glottal excitation, if the sound is voiced (voice pitch or Fo) is encoded into stimulation rate.

(c) The amplitude of the second formant (A2) is encoded into stimulation amplitude.

It has been found that these three parameters contain a large proportion of the intelligibility of speech and particularly information which is not available by lipreading.

However, as pointed out in the section on Psychophysics in the introductory parts above, the perceived pitch with varying stimulus frequency is different to the stimulation frequency. Thus, it is necessary to translate and offset the speech Fo signal via a transformation which will allow the stimulation frequency (Fo') to produce a percepts close to the actual Fo frequency.

STRATEGY 2

(a) The frequency of the second formant (F2) is encoded into electrode position/selection.

(b) The frequency of the first formant (F1) is encoded into stimulation rate.

(c) The amplitude of the overall signal (A) is encoded into stimulation amplitude.

This alternative speech processing strategy has the advantage of providing a faster stimulation rate which we believe may result in more naturally sounding speech for some patients. In particular, since the stimulation rate is F1, and the amplitude of stimulation is encoded from overall amplitude of the acoustic input, for speech signals, the Fo modulation of the speech signal is also perceived by the patient as a modulation of stimulus amplitude. However, this faster stimulation strategy may result in greater power consumption, with accompanying reduction in battery life.

We have found that the best choice of speech processing strategy depends upon the patient, with some patients 'liking' one strategy more than another, even though performance at speech communication tests may be similar in both cases. It is thus an advantage to be able to choose the optimal speech processing strategy for each patient individually, and this feature is not available in the prior art.

FIG. 18 is a block diagram of the WSP front end, with circuit element blocks identified. In general, each block is made in this embodiment with conventinal circuit techniques, and anyone skilled in the art could create a circuit to reproduce the functins described. The choice of stimulation strategy is made in the speech processor by selection of circuit jumpers or switches 120 and 121.

PREAMPLIFIER AND SQUELCH

The microphone or other signal source 100 is amplified by a high gain low power microphone preamplifier 101, incorporating automatic gain control, ar AGC. The AGC allows the front end to operate without limiting, and operates in the conventional manner, with an AGC attack time of about 1 milliseconds, and an AGC decay time constant of about 220 milliseconds. However, the voltage controlling this gain is monitored and during periods of high gain (i.e., low signal) is stored by a minimum detector 114 and used as a reference level.

The preamplifier has a maximum gain of 80 dB, with a full gain bandwidth of 4.4 kHz. Pre-emphasis and deemphasis is possible to compensate for different microphones, as conventional directional miniature hearing aid microphones will require pre-emphasis of 6 dB/octave above about 1 kHz.

Circuitry is included to generate a SQUELCH signal which is used to de-activate the encoder during periods of no signal. When the incoming signal increases a preset amount above the level held in the minimum detector (determined by the attentuator 115), a comparator 116 generates a logic level signal to enable the speech processor encoder. Otherwise it is assumed that background noise only is present and the encoder and output stage is disabled. The squelch circuit has a time out of about 200 milliseconds, such that the encoder is de-activated 0.2 seconds after the end of the last loud signal.

Thus, for speech, the SQUELCH signal will enable the encoder during speech, and will allow up to 0.2 seconds delay between words before disabling the encoder. For nonspeech signals, such as environmental sounds like warnings, telephones, doors, etc., which are impulsive, the SQUELCH circuit will also enable the encoder to produce stimuli.

The squelch circuitry provides the advantage that battery life is conserved, as the encoder and output stage are active only when sufficient signal is present. This also has the advantage that the patient is not subjected to annoying or incomprehensible stimulation when used in environments with a high level of continuous background noise. However, in some circumstances, it is desirable to be aware of all background noise, and the patient has the ability to disable the operation of the squelch circuitry by a switch on the front panel of the WSP to continuously enable the encoder and output stage.

SECOND FORMANT (F2) EXTRACTION

The frequency of the second formant varies according to the utterance and the speaker, between about 800 Hz and 3300 Hz. To extract this formant, a high pass filter 102 is used. Because each successive formant is of lower amplitude than its predecessor, F1 values from some speakers could dominate the output of the filter if it were turned to a lower frequency. The filter is optimized to produce a predominance of F2 for a range of speakers. This filter uses an infinite gain multiple feedback circuit because of the requirement for gain in the passband. Typically the gain is 4.5, Q=1.3 and fo=1.87 kHZ.

The output of the highpass filter is passed through a zero crossing detector 103 which has hysteresis so as to remove extraneous crossings produced by noise or the intrusion of F3 frequencies. In order to accommodate variations in peak signal amplitude, the hysteresis amount is derived from the output of a peak detector 109 which sets the leval appropriately. The magnitude of the hysteresis is about 20%.

The output of the zero crossing detector is input to a Frequency to Voltage Convertor 104 consisting of a monostable followed by a lowpass filter. Because the voltage produced by this circuit is subject to jitter a further hysteresis circuit 105 operates on the voltage representing the F2 frequency, with a hysteresis of about 14%. The final output of the F2 estimation circuitry is a voltage proportional to frequency at 1 kHz per volt.

SECOND FORMANT AMPLITUDE (A2)

The amplitude of the F2 signal after the high pass Filter is obtained via the peak detector 109. The output of a 2 pole linear phase lowpass filter with a corner frequency of 35 Hz provides a smoothed estimate of the formant amplitude A2.

VOICE PITCH (Fo) EXTRACTION

The periodic excitation of the resonant system of the vocal tract during a voiced utterance results in an amplitude modulated signal envelope. The excitation rate or voice pitch is derived from this envelope by full wave rectification using conventional full wave rectifier circuit built around an operational amplifier 106. The rectified signal has the DC level removed by AC coupling in a capacitor 107 which introduces a zero at about 70 Hz, and is then low pass filtered. This filter 108 is a 3 pole 200 Hz low pass filter in the Sallen and Keys configuration. Full wave rectification is used to double the "carrier" or resonance frequency thus easing the problem of separating the first formant frequency from the voice pitch.

The resulting signal is converted to a voltage proportional to frequency with an identical circuit arrangement to the F2 path (except for the appropriate time constants) consisting of a zero crossing detector 110 with hysteresis level set by a peak detector 117. A frequency to voltage convertor 112 produces a voltage proportional to Fo frequency, at 130 Hz per volt.

A voltage controlled oscillator 113 driven by this voltage then produces another frequency Fo' which is proportional to but not necessarily equal to Fo. The VCO has adjustable input voltage range, and also an adjustable offset to give a range of control over the linear conversion from Fo to Fo'. This Fo' frequency is used as the stimulation rate of a patient electrode, selected by F2 and stimulated at a level related to A2.

FIRST FORMANT (F1) AND AMPLITUDE EXTRACTION CIRCUITS

A peak detector 118 following the microphone preamplifier follows peaks in the signal, which will be dominated by peaks at the F1 rate. The value of the peak is held in a Peak Hold circuit 119 and is used to determine stimulation amplitude. This circuit is realized with an operational amplifier charging a capacitor through a diode, with the capacitor voltage returned to the summing junction of the operational amplifier. Thus the capacitor voltage follows the peaks in the signal, and the operational amplifier output will have excursions between the negative supply rail, and the present peak value. The output of the operational amplifier is coupled with a capacitor and a resistor to the START input of the encoder, to start the encoder at the F1 rate, if this is selected. A START pulse will be produced everytime the input signal amplitude falls below the currently held peak value, and thus the encoder will stimulate at the F1 rate, at an amplitude determined by the value of the last peak in the signal.

OTHER CIRCUITS

The two voltages, ELSEL and STAMP are made available to the ADC via a two input analog multiplexer and sample and hold circuit under control of the ADC and encoder, as shown in FIG. 17.

Additional control circuitry (not shown) allows the patient to operate a TEST function by way of the front panel switch on the WSP. The purpose of the TEST function is to generate comfortable level stimulus at a constant rate on the lowest frequency percept electrode. This electrode is usually the most apical electrode. This gives the patient a known and constant percept so that he may easily and simply adjust the coil position. The TEST function merely causes the input to the VCO 113 to be a constant, low level, and the output of the A2 path to be the maximum value. In addition, the TEST function is configured to impose a dummy load on the power supply, and light a LED if sufficient battery power remains. This is a useful feature to warn the patient of battery failure.

SPEECH PROCESSOR ENCODER

Overview

The speech processor encoder chip is used to generate pulse burst sequences which are subsequently transmitted via the output stage to the implantable receiver/stimulator in the patient. The pulse burst sequence is under the control of a program stored in an electronic memory device, such as an EPROM (e.g. 27C16), and the number of pulses in the variable parts of the pulse burst sequence is determined by the output of an ADC, and the program in memory.

The speech processor encoder chip is essentially a flexible, programmable pulse generator. The encoder chip is able to produce sequences of constant frequency pulses with the number of pulses and time between pulse bursts determined either by the internal program or in response to an externally applied analog signal (through an external ADC). The frequency of output pulses is determined by the frequency of the clock, and the system is designed to be able to work from DC to a frequency determined by the practical limits (about 10 MHz) of the CMOS technology in which the invention is embodied.

In this invention, the encoder chip is used to generate the frame of pulse bursts required for powering and controlling the implantable receiver stimulator. The format of these pulse burst frames is illustrated in FIG. 8. However, the encoder chip has been designed to be flexible, and will be useful in a number of applications where it is necessary to produce bursts of pulses. In particular, it is expected that the encoder chip will be useful in applications where a different data encoding format is used, e.g., for use with future generations of receiver stimulation designs.

ARCHITECTURE

FIG. 19 is a block diagram of the encoder, showing all functional blocks. In some ways, the architecture of the encoder is similar to a conventional microprocessor in that there is an Address Bus, a Data Bus, Instruction Decode logic etc. However, in distinction from conventional microprocessors, there is no Arithmetic Logic Unit (ALU), as the encoder is not required to perform any arithmetic.

The encoder also has similarities to a conventional state machine. The encoder, however, is not designed to allow program branches or jumps dependent upon data generated in previous states, and the program running the encoder has each instruction executed exactly once from start to halt.

The function of the encoder is to generate a number of pulses in a burst, dependent upon data presented to it on the data bus, and the contents of the instruction currently fetched from memory. The memory address bus has its contents originating from either the program counter (for instruction fetches, for example), internal registers (Electrode Latch, F2 Latch, and A2 Latch), or the data output from the ADC—or combinations of these.

Circuitry exists in the encoder so that operation is enabled or disabled from external control lines shown symbolically as 130. Provided the encoder chip is ENABLED each START pulse (shown symbolically as 131) initiates a sequence of pulse bursts called a frame, as defined before. START pulses occurring during a frame are ignored. This is important for a cochlear implant encoder since it is essential for the power/data signal format described above for all frames to be properly finished.

Each burst of pulses is numbered sequentially from 0. The number of bursts in each frame is constant and fixed by the program in EPROM. The number of pulses in each burst may be fixed, or determined from the EPROM mapping between ADC value (an address) and the pulse count at that address. A fixed delay between bursts (8 clock times) is required to decode the next instruction, and load the pulse count for the next burst.

There is a start delay between the START pulse and the first burst. This time is the same as the INTER-BURST DELAY, with +2, −0 clock cycles jitter because the START pulses are asynchronous with the internal clock. A frame is only initiated by a START pulse if the chip is enabled. Changes to the enabling inputs to the encoder during a frame will have no effect and all frames will be finished. This is an important safety feature in the cochlear implant system, as it would be potentially dangerous or uncomfortable to the patient if the frame of pulses was not of the format required, because it could lead to generation of incorrect stimulus pulses from the receiver-stimulator in the patient.

The encoder is considered to exist in one of four states as follows:

1. HALT awaiting a START pulse to initiate operation;
2. FETCH an instruction is fetched from the memory location determined by the program counter and loaded into the INSTRUCTION LATCH 134;
3. DATA the instruction so fetched is decoded and data from the PROM is loaded into the DATA LATCH 139. The register used to supply the address of this data is determined by bits set in the instruction latch, and as decoded by the Instruction Decoder 133; and
4. COUNT the 9 stage synchronous binary counter (Burst Counter 142 is enabled and counts up. When the COUNTER value equals the number in the DATA LATCH, the 9 Bit Binary Comparator 140 asserts the A=B signal 145 and the next cycle is initiated in the Internal Timing and State Generator 132.

The operation of the encoder is that a START pulse initiates the first instruction fetch from memory at an address determined by the PROGRAM COUNTER 135. The instruction so fetched is loaded into the INSTRUCTION LATCH 34.

The next state is the DATA state, where data from the memory is loaded into the DATA LATCH 139, and may also be loaded into other latches as needed, including the ELECTRODE LATCH 136, the F2 LATCH 137, or the A2 LATCH 138. The memory address from which the data is obtained is determined by the instruction, and various control signals (shown symbolically as 148) are decoded from the instruction in the INSTRUCTION DECODER 133.

The next state is the COUNT state, where the 9 BIT BINARY COUNTER 142 counts up from its starting value to the value of the number in the DATA LATCH 139 and a ninth bit obtained from the current instruction. During counting, the internal clock signal may be made available to the OUTPUT pin, and is sent to the output stage, under control of the BURST COUNTER CONTROL LOGIC 143. A 9 BIT BINARY COMPARATOR 140 determines when the two numbers are equal, and causes the counting to stop and the next state of FETCH to be entered.

Thus the Encoder Chip continues through the states of FETCH, DATA and COUNT until the HALT instruction is fetched from memory, at which time further operation stops, and the encoder now exists in the HALT state.

The input signals to the encoder are:

START A signal generated externally by the WSP front end (i.e., Fo') at a rate determined by the incoming speech signal.

ENABLE Enabling signal or signals (depending upon the embodiment) which allow the encoder to generate pulse frames in response to a START pulse.

In addition to these control signals, the Address Bus 146 is bidirectional, which the encoder putting out memory addresses, and the ADC data sometimes being applied to the address bus as well for mapping between F2, A2 and number of pulses. Five bits of the 8 ADC data bits are connected directly to the address bus (A7 to A3), and the other three bits are input to special pins which are internally connected to the address bus at the correct time (AD2-AD0).

The data bus 147 is input to the encoder only, and comes from the memory. Note that in the wearable speech processor, the memory is a UV Erasable PROM, but it is not a requirement that this type of memory be used exclusively. In fact, a random access memory is used within the Interface Unit of the Diagnostic and Programming Unit to emulate the PROM. Other memory technologies, such as EE-PROM could also be used.

The outputs for the encoder are:
OUTPUT: Bursts of output pulses sent to the RF output stage of the wearable speech processor.
DAMP: A signal asserted when pulses are not being output to allow damping of the RF output stage.
DOUT: An output line set/reset under program control (as described below). This line is included for expansion in the future, and may be particularly useful for example for adjustment of transmitted power level to conserve power, or expansion into more memory address space under program control.

In addition to these input and output signals, numerous control signals bus are used to interface the encoder to the ADC and memory. Of particular importance is the signal CE 149 which is used as the Chip Enable for the Memory, and also as the Convert Start for the ADC. A separate Chip Enable from the encoder instead of enabling the memory the whole time allows the use of semiconductor memories whose power consumption is less when not enabled.

The instruction fetched from the memory is an 8 bit word with the bit allocation as defined below.

|  | 7 | 6 | 5 | 4 | 3 | 2 | 1 | 0 |
|---|---|---|---|---|---|---|---|---|
| BIT: | MSB | | | | | | | LSB |
| LABEL: | EXT | BC1 | BC0 | RS2 | RS1 | RS0 | A10D | MUX | where the functions of these bits is:

| | |
|---|---|
| MUX | Multiplexer. This bit is directly output to a pin and is used to select one of two analog inputs to the analog to digital converter under program control. For interfacing convenience, the complement of this bit is also output to a pin. |
| A10D | This bit is gated to the most significant bit of the address bus during the data cycle and allows data to be accessed from either half of the 2048 byte address space. The mapping strategy is discussed in further detail below. |
| RS0 | REGISTER SELECT. These bits determine which |
| RS1 | register is to be gated on to the address bus |
| RS2 | during the DATA cycle. A detailed explanation is presented below. |
| BC0 | Burst Counter Control. These bits are used to |
| BC1 | decode the mode of operation of the burst counter as described further below. |
| EXT | (Extend) This bit is used to add an extra bit input to the magnitude comparator to allow for 9 bit counting to extend the burst counter timing interval by an extra 256 pulses of burst counter clock. |

ADDRESS SELECTION

The data stored in the DATA LATCH is read from the memory during the DATA state. The location of this data in memory is determined by the contents of the address bus at the time. The Register Select bits in the control word are used to determine the source of the memory address in the DATA cycle. The bit assignment, and the use of each of the possibilities is described below. The register select bits may also be thought of as defining the instruction to be executed by the encoder from the set of 8 possible instructions.

In order to understand the following descriptions, it is helpful to examine FIG. 20 which graphically describes how the 1024 bytes of each half of the PROM address space is partitioned. The reader should note that this partitioning has been designed for maximum utilization of the available address space and this may explain some of the seemingly unusual bit allocations. In the register select bits, RS2, RS1, and RS0 is shown after the instruction name.

FIX-FIXED DATA (000)

The program counter (which was incremented at the end of FETCH) is gated onto the address bus. Thus the DATA stored in the next byte in memory after the instruction is loaded into the DATA latch. The program counter is then incremented. This mode is used for generation of fixed duration delays or data bursts, as the number of pulses to be sent in the burst is stored in the ROM.

FXDT-FIXED DATA AND TOGGLE DOUT (001)

This instruction is identical to the FIX instruction except that the DOUT output line is changed in state.
NOTE: The DOUT line is always reset to 0 at the start of a frame.

FXAT-FIXED DATA AND TOGGLE A10 SELECT FLIP-FLOP 101.

This instruction is the same as the FIX instruction except that a flip-flop called the A10 select flip-flop is toggled. This flip-flop is in the instruction decoder, and is used to select either the A10D signal or AD2 (the ADC input bit) for the mapping the inputs either to two halves of memory or extending the amplitude precision by one bit. See also notes on FIG. 20 for further explanation.
NOTE: The A10 select flip-flop is always reset to 0 at the start of a frame.

F2ADC-ADC INPUT (F2 VALUE) 111.

The 8 bits output from the ADC is gated onto bits 2 to 9 of the address bus (MSB is A9) and bits 0 and 1 of the address bus are forced to logic 1. The data in this area of PROM is the map between F2 and electrode number. The ADC is so arranged with its reference voltage that it can never reach a value of 11000000 (=224) or greater to guarantee that the ADC value does not intrude into the program address space.

Alternatively, it may be decided that the program in PROM will occupy address space in one-half of the PROM (e.g., A10=1), and the F2 to electrode map will occupy the other half (A10=0). This means that it is then unnecessary to restrict the F2 to electrode mapping address space, and the full 8 bit range may be used.

At the same time the ADC is read, the 8 bit F2 value is also stored in the F2 LATCH 137 of 8 bits, from which it may be read again later.

Additionally, bits D7 to D2 of the DATA so generated from the PROM (i.e., the electrode number) are stored in the ELECTRODE LATCH 136, offset, and in bit reversed order.

The arrangement shown in FIG. 20 is for the electrode number to be encoded into bits 6 to 2 of the output from the PROM, with D1=1, and D0=0. This will encode the electrode number n, as 4*n+2. However, it is possible to also encode the electrode number as 8*n+4, by shifting the electrode number left 1 bit, and setting D2=1, and D0=D1=0. As described in the system description above, the electrode number is encoded in the pulse burst to the implant by 8*n+4. The encoder chip design allows flexibility in encoding electrode number to take advantage of future designs which may utilize a different electrode encoding scheme, which would have advantages in terms of the maximum rate of stimulation.

F2L-LATCH INPUT (011)

The data stored in the F2 LATCH previously generated by an F2ADC instruction (111) (FIG. 18) is again gated onto the address bus. When used in conjunction with instruction bit A10D, this allows a choice of two DATA values for any F2ADC value.

This is important because it allows the use of different stimulation strategies in the future, for example utilizing more than one electrode for each F2 value, such that electrodes are stimulated in pairs. Alternatively, it may be desirable to have different stimulus pulse lengths for each electrode, and this could be stored in the second half of the memory address space, and accessed with this instruction.

ADCE-ADC Input and Electrode (110).

The most significant 5 bits of the ADC are gated onto bits A5–A9 of the address bus. The least significant 5 bits contain the contents of the electrode latch (FIG. 19) in bit reversed order. The electrode number must be constrained in the PROM to be no bigger than 1011 (23) to prevent intrusion of this part of the address space into the other address space. In the present design, this, therefore, limits the number of electrodes to 23.

However, as mentioned above, the electrode latch is of 6 bits in length, and the choice of which five of the six bits are placed onto the address bus depends on the choice of coding of electrode number as 4*n+2 or 8*n+ 4. An external control input to the encoder chip allows the user to choose which encoding strategy is to be used and thus which 5 of the 6 bits are to be placed onto the address bus at this time.

It is possible to use one extra bit of precision in the ADC by gating in onto A10 line if the FXAT instruction has been executed an odd number of times (e.g.:1) since the frame start. Otherwise, A10 will contain the contents of A10D to allow generation of pulse sequences from either half of memory.

At the same time as the ADCE instruction is executed, the 6 most significant bits (A10 to A5) are stored in the internal A2 LATCH 138 for later re-use. The A2 latch data bit from A10 thus contains either AD2 (from ADC) or A10D from the current instruction.

A2L-A2 LATCH AND ELECTRODE (010)

This is identical to ADCE (described above) except that the data previously stored in the A2 latch by an ADCE instruction is used instead of the ADC input. The data is not re-latched into the A2 latch but retained.

HALF-HALT (100)

This is a special instruction which is used to signify the end of a sequence and the initiation of the HALT state. The whole encoder chip exists in the HALT state between stimulation sequences.

The HALT instruction also generates a control signal to read the ADC (RD). This guarantees the ADC will be ready to convert the data available on the first instruction to be executed in the frame so that ADC data, when first read in the frame will be the value at the start of the frame.

BURST COUNTER CONTROL BITS

The burst counter control bits determine whether clock pulses are transmitted during the burst count and whether the burst counter is reset at the end of a burst.

BC0 is used to enable or disable the clock pulses to the output pin for the duration of the burst.

BC1 is used to enable reset of the burst counter upon detection of the equality of the burst counter and the data in the data latch.

If BC0 and BC1 are both zero, then the clock input to the burst counter is divided by two to allow a doubling of the time the clock is enabled to the output and the signals RG (reset gate) on ON are forced high. The choice of the source of the clock to the burst counter from either the divide by two circuitry 141 (FIG. 19) or directly from the clock generator 144 is done by an electronic switch whose state is set by control lines from the instruction decoder 133.

The burst counter and control logic 143 section is used to generate pulses according to the number loaded into the DATA LATCH 139 in the DATA cycle. The BURST COUNTER 142 commences counting at the end of the DATA cycle and counts until the value in a bit binary counter 142 equals the number in the DATA LATCH 139 at which stage counting ceases and a new fetch cycle is initiated.

The BURST COUNTER 142 is a 9 stage synchronous binary up counter. The control of the BURST COUNTER 142 is by the bits EXT, the BC0 and BC1 in the current instruction The EXT bit effectively extends the 8 bit data to 9 bits by adding an extra (most significant) bit. The state of BC0 determines whether or not the clock is enabled to the OUTPUT pin for the duration of the burst (i.e., an ON BURST or an OFF burst), BC1 determines whether or not the BURST COUNTER is reset at the end of the current burst.

It is thus possible to generate a variable number of pulses within a constant time interval. This feature is important because by using it, it is possible to guarantee that all stimulus frames are of constant time duration. This is important to eliminate timing jitter between stimulus pulses to the patient, as will be required for some psychophysical research, and may be essential in some speech processing strategies. For example, if a constant time interval of 256 clock pulses was required, the following sequence of events would occur.

1. At END of last instruction, BURST COUNTER is reset (BC1=1 for that instruction).
2. The data for the number of pulses required (N) is loaded into the DATA LATCH via the mapping in PROM, and the output is enabled and the BURST COUNTER is not reset at the end of the BURST (BC0=1, BC1=0).
3. The next instruction loads fixed data of 248 (248 pulses counted +8 pulses for FETCH and DATA time =256) with output not enabled and burst counter reset at end (BC1=1, BC0=0). Thus the counter counts from the last data value to the total pulses value without output and the time interval from start of pulse generation to end of OFF burst is constant.

This facility eliminates the need for any arithmetic to be done inside the encoder chip.

A further condition where BC0=0=BC1 (which would normally be meaningless) is used for generating very long bursts of pulses. In this condition, the input clock to the burst counter is pre-divided by two so that the time the counter is counting is exactly twice that when the normal clock is used. Thus the number of output pulses can be doubled for the same number in the data latch. This condition is detected by the Instruction Decoder circuit which asserts the appropriate internal control signals.

The equality of the 9 bit up counter and 8 bit data latch plus EXT bit from the current instruction is detected by a combinational logic network arranged as a 9 bit binary comparator 140. The equality signal (A=B) is fed back to the internal timing and state generator 132 which asserts signals to inhibit further counting of the up counter.

If the ON signal is asserted (decoded from the current instruction) the clock signal is gated to the OUTPUT pin and the DAMP signal is asserted).

INTERNAL TIMING AND STATE GENERATOR

The function of the internal timing and state generator 132 is to
generate power on reset of encoder chip;
generate the clock from the on chip crystal oscillator 144;
generate the initialization sequence which starts the program in EPROM when a START pulse is received if the chip is enabled.

The power on reset is detected from a pin PORN 151 which will go high sometime after power is applied. This signal may be easily generated from a resistor and capacitor network. The function of the power on reset is to ensure that the encoder chip powers up to a known state. In addition, in this embodiment, circuitry is included in the speech processor front end to prevent the encoder from operating if the power supply voltage is inadequate, as may occur towards the end of battery life. This is an important safety feature in the system to prevent spurious pulse frames being transmitted to the implant due to faulty operation of the logic circuits because of low supply voltage.

A crystal oscillator is formed conventionally from a chain of an odd number of inverters. This is then gated into a divide by two circuit and the resulting clock is buffered heavily and distributed to the rest of the chip.

The divider is only enabled while the encoder chip is running to conserve power. This is important because, in CMOS technology, practically all power consumption of the chip is derived from capacitive charging and discharging of nodal capacitance, whereas the DC power consumption is effectively zero. The divide by two circuit guarantees exactly equal mark/space ratio of the internal clock, and thus the external output signal, which is important for best efficiency of the output stage.

The initializing sequencer is set up so that all enable inputs must be asserted to allow the START pulse to initiate operation of the encoder. After the program in memory has been started, further changes to START or the Enable inputs will have no effect until the current frame is complete (i.e., HALT instruction executed).

INSTRUCTION LATCH AND INSTRUCTION DECODER

The INSTRUCTION LATCH 134 is an 8 bit gated D latch which is loaded with the current instruction in the FETCH cycle. The contents of RS0-RS2 in the instruction latch are then decoded by combination logic 133 and are used to determine the source of the address bus bits for obtaining the burst count as described above. The memory contains data on pulse burst length mapped from the ELSEL data and the STAMP data from the Speech Processor Front End. The INSTRUCTION DECODE LOGIC decodes the RS0-RS2 bits in the current instruction and sets signals to enable the appropriate latched data or ADC data to the ADDRESS BUS in the DATA cycle.

The timing during the DATA cycle is such that the ADDRESS bus is set up by the various latch enable or ADC read signals prior to the time when the memory data is read into the DATA LATCH (and other latches as the case may be). Thus the memory has about 2.5 clock cycles for the data to be stable (about 1 uS), which should be adequate for even slow memories.

A network of gates is used to decode the current instruction and assert the appropriate internal control signals for gating signals on to the Address Bus. Also, signals are generated for gating the contents of the Data Bus into the electrode latch, the F2 latch or the amplitude latch at the S2 time, depending on the instruction. Various internal control signals 148 are distributed to parts of the encoder circuit.

ADDRESS BUS ARBITRATION LOGIC AND PROGRAM COUNTER

The memory contains both the program and the data for the mapping between F2 and electrode number and electrode number combined with amplitude data to number of pulses (which will eventually control stimulus strength or duration). Thus provision is made so that the address bus input to the memory may come from the following sources.
1. Program Counter 2. ADC (8 bits) 3. F2 latch (latched ADC data) 4. Electrode latch plus most significant 5 bits of ADC 5. Amplitude latch plus electrode latch.

The address space is mapped as shown in FIG. 20 and there are also gates to guarantee 1 states when using program counter, ADC input or F2 latch as input on some address bits.

The F2 LATCH 137 (FIG. 19), the A2 LATCH 138 and the ELECTRODE LATCH 136 are all simple gated D-flip-flops, which are loaded in the DATA cycle if the appropriate condition codes are set up in the INSTRUCTION LATCH 134. These latch outputs are gated to the ADDRESS BUS for the whole of the DATA cycle by transmission gates if selected by the instruction decode logic.

The PROGRAM COUNTER 135 is a 6 stage synchronous binary down counter which is decremented once each FETCH cycle, and once in the DATA cycle if fixed data is called for. The PROGRAM COUNTER is reset by an internal signal generated from a START pulse in the Internal Timing and State Generator, or by PORN. The most significant bit of the PROGRAM COUNTER is enabled to A10 during the FETCH cycle. In the DATA cycle, and A10D bit from the INSTRUCTION LATCH may be gated to A10 to enable either half memory mapping (except in FIX type instructions).

The reason that the PROGRAM COUNTER is a down counter is to reduce the possibility of ADC data intruding into the program space in memory and generating erroneous pulse bursts. Thus, the program always starts at address 7FF (HEX) (the highest address) and goes down to address 783 (HEX), the continues from address 3FF (HEX) and down to 383 (HEX) for a total program space of 64 bytes. This program space is adequate for even complicated pulse bursts, such as might be used for multiple electrode stimulation.

In fact, in this embodiment described here, it is possible to determine the most significant bit of the starting address of the program (i.e., A10) by strapping an externally available pin to either logic high or low. This has the advantage that it is possible to configure the EPROM with two different programs in it, which may be chosen by the user. For example, two different programs may be established for noisy environments, and quiet environments, or for music or speech, etc. Thus the starting address may be set to be either 7FF (Hex) or 3FF (Hex).

Since the whole 8 bits of ADC input are not always used, the least significant 3 bits are gated onto the address bus by tri-state buffers enabled by signals generated by the instruction decode logic in response to instructions which require all bits (i.e., F2ADC). This is not shown in the circuit diagram, as anyone skilled in the art could duplicate this function.

The A10 bit may come from one of 3 sources:
1. The LSB of the AMPLITUDE LATCH
2. The MSB of the Program Counter
3. The A10D bit in the current instruction
4. The AD2 bit input of the analog to digital converter.

Logic is provided to select between these inputs at the appropriate time.

The electrode latch is a 6 bit latch and the six bits of electrode number mapped from F2 input in response to the F2ADC instruction are stored in the latch. Either the upper 5 or lower 5 bits may be enabled to the address bus for an ADCE or A2L instruction by means of an array of multiplexors. This is to allow coding the electrode pulse burst as either 4N+2 OR 8n+4 (according to receiver design) without affecting EPROM addressing. The choice of which 5 bits are gated to the bus is made by strapping the externally available ELOPT pin to VCC or GND. This logic circuitry is not illustrated in FIG. 19 as it is only incidental to the operation of the encoder.

The external address bus is driven by TRI-state bus drivers. Address bits 5, 6, 7, 8 and 9 are put to TRI-state level when the ADC is to be read as the ADC data is then gated to the Address Bus. These output pins are also fed back into the chip for storage in the internal latches as needed.

TEST SIGNAL SELECTOR (TEST)

Because of the limitation on number of pins, it is not possible to have access to all internal signals directly. However, all important internal signals are brought to three 8 to 1 multiplexers in a Test Signal Selector 152. The select signals for these multiplexers are brought outside, and are labelled TPS0, TPS1 and TPS2. Thus 24 internal signals are available using only six pins. In normal operation, TPS0, TPS1 and TPS2 are tied to logical 1, and the signals available to outputs are signals which are useful during normal operation of the encoder.

In addition, all address bus pins may be set to TRI-state when the chip is in test mode (i.e., TPS0, TPS1, and TPS2 not all tied to logic 1), and one of the enable lines is asserted. This condition allows access to the address bus externally (e.g., to program the EPROM while in circuit).

This is an important feature for the ease of use of the system as a whole, because it eliminates the need to remove the EPROM from the circuit during psychophysical testing of the patient. Apart from the advantages of ease of use, it also means that it is possible to take advantage of denser packaging technology (such as leadless chip carriers) which are not amenable to non-permanent fixation to the printed circuit board in the WSP. In addition, it allows the future possibility of more than one device sharing the same address bus, for example if it was desired to incorporate a microprocessor controlled speech processing strategy, and it was desired to store the controlling memory in the same PROM as the encoder program, and the patient data map.

SAMPLE PROGRAM FOR SPEECH PROCESSOR ENCODER

An example program for sending stimulus frames to the implant is shown below and will be used as the basis of the following discussion. This program will generate a train of pulse bursts according to the stimulus pulse frame definition shown in FIG. 8. It should be understood that other programs could be used to generate the same stimulus frame, and may be used for different patients (e.g., to generate bipolar stimulation, or stimulus frames with different stimulus pulse lengths-phi 1 and phi 2).

|      | ADDRESS | INSTRUCTION | | | | | | | DATA | |
|------|---------|-----|-----|-----|-----|-----|-----|-----|-----|-------|----------|
| STEP | (HEX)   | EXT | BC1 | BC0 | RS2 | RS1 | RS0 | A10 | MUX | (HEX) | MNEMONIC |
| 1    | 7FF     | 0   | 1   | 1   | 0   | 0   | 0   | 0   | 1   | 61    | FIX      |
|      | 7FB     | 0   | 0   | 0   | 0   | 0   | 1   | 0   | 0   | 04    | CONST 4  |
| 2    | 7F7     | 0   | 0   | 1   | 1   | 1   | 1   | 0   | 0   | 3C    | F2ADC    |
| 3    | 7F3     | 0   | 1   | 0   | 0   | 0   | 0   | 0   | 0   | 40    | FIX      |
|      | 7EF     | 1   | 1   | 1   | 1   | 1   | 0   | 0   | 0   | F8    | CONST 248|

-continued

| STEP | ADDRESS (HEX) | INSTRUCTION EXT | BC1 | BC0 | RS2 | RS1 | RS0 | A10 | MUX | DATA (HEX) | MNEMONIC |
|---|---|---|---|---|---|---|---|---|---|---|---|
| 4 | 7EB | 0 | 1 | 1 | 0 | 0 | 0 | 0 | 0 | 60 | FIX |
|   | 7E7 | 0 | 0 | 0 | 0 | 1 | 1 | 0 | 0 | 0C | CONST 12 |
| 5 | 7E3 | 0 | 1 | 0 | 0 | 0 | 0 | 0 | 0 | 40 | FIX |
|   | 7DF | 0 | 0 | 0 | 1 | 0 | 1 | 0 | 0 | 14 | CONST 20 |
| 6 | 7D7 | 0 | 1 | 1 | 1 | 1 | 0 | 1 | 0 | 7A | ADCE |
| 7 | 7D3 | 0 | 1 | 0 | 0 | 0 | 0 | 0 | 0 | 40 | FIX |
|   | 7CF | 0 | 0 | 0 | 1 | 0 | 1 | 0 | 0 | 14 | CONST 20 |
| 8 | 7CB | 0 | 1 | 1 | 0 | 0 | 0 | 0 | 0 | 60 | FIX |
|   | 7C7 | 1 | 1 | 1 | 1 | 1 | 1 | 1 | 1 | FF | CONST 255 |
| 9 | 7C3 | 0 | 1 | 0 | 0 | 0 | 0 | 0 | 0 | 40 | FIX |
|   | 7BF | 0 | 0 | 0 | 1 | 0 | 1 | 0 | 0 | 14 | CONST 20 |
| 10 | 7BB | 0 | 1 | 1 | 0 | 0 | 0 | 0 | 0 | 60 | FIX |
|   | 7B7 | 1 | 1 | 1 | 1 | 1 | 1 | 1 | 1 | FF | CONST 255 |
| 11 | 7B3 | 0 | 0 | 0 | 1 | 0 | 0 | 0 | 1 | 11 | HALT |

This program consists of 11 steps. Each step will consist of a FETCH, DATA, and COUNT cycle. The detailed timing for the first step is given, and other steps will have similar timing.

The program is initiated by the arrival of a START pulse from the speech processor front end, assuming the encoder is enabled. The START pulse causes the program counter to be reset to 11111, the burst counter is reset to 0, and starts the internal timing and state generator. In the first FETCH cycle the address bus contains 7FF, the address of the first instruction. The contents of this address (61 HEX) are strobed into the instruction latch during the first FETCH cycle. The program counter is decremented at the end of the FETCH cycle.

In addition, the encoder and ADC is arranged so that the ADC conversion is initiated when the first instruction is fetched from memory. In this way, the ADC will be converting the value presented to its input at the same time as the encoder is executing the first instruction or so. The ADC used is an Analog Devices AD 7574, and has the desirable characteristic that further start convert signals are ignored until the previous data is read.

In the data cycle, the instruction is decoded as a fixed data instruction so the program counter is again enabled to the address bus. The contents of the next byte (at 7FB) in the program (04 HEX) are strobed into the data latch during the DATA cycle and the program counter is decremented again at the end of the DATA cycle. The burst counter control bits have been set by the contents of the instruction latch.

At the end of the DATA cycle, the COUNT cycle begins, and the burst counter is enabled to count to 4 cycles. After 4 cycles, the equality of the burst counter and the data latch is detected, and a pulse is generated which initiates the next FETCH cycle. These four pulses are output to the OUTP pin and the bursts counter is reset at the end. These four cycles transmitted to the receiver/stimulator are the Synch Burst referred to in FIG. 8.

For step 2, the next instruction (3C HEX) is loaded from address 7F7(HEX) and the program counter is decremented. The data from the ADC is read. The ADC had a conversion started during the first instruction read by the same line which is used to chip enable the EPROM. The output of the ADC (8 bits) is enabled to the address bus bits 2 to 9 as shown in FIG. 20, and a number is read from the EPROM at the address so generated. This number will encode the electrode selected as 8*n+4, and the number is output as a number of pulses. The electrode number is also stored in the ELECTRODE LATCH during the DATA cycle. The actual electrode selected depends upon the way that the ELSEL signal is mapped into electrode number for this particular patient. A detailed discussion on the mapping algorithms appears later in this disclosure.

The number mapped from the F2 ADC input is output as a burst of pulses. At the end of this burst, the burst counter is not reset but is left in the state at which EQ was detected. In step 3, the next instruction (40) is gated into the INSTRUCTION LATCH at the next FETCH. The constant data, 248 is gated into the DATA LATCH during the DATA cycle. The burst counter is enabled to continue counting from its end value to 248 at which time the counter is reset and the next instruction is fetched. Thus the active electrode burst and subsequent inter-burst delay will take the time for 256 clock times, regardless of the actual number transmitted to the receiver/stimulator.

Step 4 will result in the transmission of a 12 pulse burst which, in this example, will code the stimulation mode as 1, or multipolar. Other stimulation modes could be used. Step 4 is followed by a constant period of no output with the FIX instruction in Step 5 to provide the inter-burst delay.

In Step 6, the instruction is ADCE, and the 5 bits in the electrode latch are gated to Bits 4 to 0 of the address bus in bit reversed order as shown in FIG. 20, and the 5 most significant bits of the ADC output are gated to bits 9 to 5 of the address bus. The data at the location in EPROM will then code the stimulus amplitude for the selected electrode at the value of the input signal (STAMP) represented by the number read from the ADC. Step 7 generates the interburst delay for the delay after the amplitude burst generated in Step 6.

Steps 8, 9 and 10 generate the Phi 1 and Phi 2 times which, in this example, are shown to be 255 clock pulses long, although other Phi 1 and Phi 2 times could be chosen.

Finally, the last instruction in Step 11 is a HALT instruction. This instruction causes the encoder to stop sending data, and also reads the ADC to make sure that the ADC is ready to begin a conversion on the first instruction fetch of the next pulse frame. In addition, as shown in this example, the HALT instruction changes the state of the MUX bit so that the data presented to the ADC for the start of the next frame will be ELSEL. Note that the MUX bit is caused to change value with Step 1 of the program, so that the next ADC conversion (for amplitude burst) will cause the conversion of the STAMP signal. The MUX bit operates a signal control line to select one of two analog signals to the ADC convertor as shown in FIG. 17.

OUTPUT STAGE

The output stage is a Class D RF output stage using two enhancement mode power Field Effect Transistors (FETs), and is illustrated in FIG. 21. The signal 'OUTPUT' from the Encoder is level shifted from the logic levels of the encoder by a capacitor 200 and resistor 201. An N channel FET 204 selected to have a low ON resistance and a threshold of less than the logic swing is turned on by this level shifted signal. The drain of the FET is connected to the coil 207 worn by the patient by a coaxial cable 205. A capacitor 206 is selected to tune the coil. The value of the capacitor depends upon the length of the coaxial cable, as the parallel capacitance of the coaxial cable itself will contribute to the tuning capacitance.

The other end of the coil is connected to the most positive supply. When the N channel FET turns on, current is sunk through the coil. When this FET turns off, the voltage across the coil rises sinusoidally to about 35 volts. The timing and tuning is arranged such that the voltage across the coil is thus typical of a class D output stage, consisting of half sine wave shaped pulses, of about 35 Volt amplitude.

A P channel enhancement mode FET 202 is in parallel with the coil via a silicon diode 203. This FET is turned on, and thus short circuits the coil, when the DAMP signal from the Encoder is asserted. The purpose of this is to damp out any residual oscillations in the tuned circuit system at the end of each burst so that the correct number of pulses will be received by the implanted receiver/stimulator.

The design of the coil takes into account many factors, such as:
1. The number of turns such that the turns ratio from the external coil to the internal coil yields the correct voltage at the receiver/stimulator.
2. The inductance to give the correct resonant frequency, with high Q for high efficiency, not requiring too large a tuning capacitor.
3. The diameter to give the best coupling efficiency to the internally worn coil, and to allow some lateral tolerance in position of coil.
4. The construction, so that the coil may be of simple, flat construction, to allow the coil to be worn inconspicuously under the patient's hair, over the site of the implant.

DIAGNOSTIC AND PROGRAMMING UNIT AND INTERFACE UNIT

The Diagnostic and Programming Unit (DPU) and Interface Unit (IU) are used together with a Wearable Speech Processor during the testing of the patient's psychophysics, and to set up the program and map in the WSP. The DPU is a conventional, off-the-shelf microcomputer system, to which software has been added. The IU is a specially designed device to interface between the DPU and the WSP.

The DPU has available a communications interface which enables communication between it and the IU. In the embodiment described here, a 16 bit parallel communications link is used, but other formats or configurations could be used equally well, such as serial, or parallel with a different width of the data path.

As described in the previous section, the WSP encoder works by fetching instructions from the EPROM in the WSP, and mapping the incoming formant data (F2 and A2) from the speech processor front end into the appropriate selection of electrode and amplitude to be sent to the implanted receiver stimulator. The algorithims for mapping are discussed in a subsequent section. During testing and setup of the patient's WSP, the following functions must be performed:

1. Presentation of known and controlled stimuli to the patient, on nominated electrodes. The stimuli result in a response from the patient which is recorded. Several tests such as measurement of thresholds, pitch ranking of electrodes, and loudness scaling of stimulus intensity are performed.
2. Use of the psychophysical data obtained from the tests above to generate a map between F2 and electrode to be stimulated, and A2 and amplitude of stimulation on each electrode.
3. Test the map so generated using the patient's own speech processor using live audio input, such as speech.
4. If suitable, install this program and data into the PROM on the WSP. This involves erasing any data which may have been previously in the PROM, and programming the PROM with the new data which has been generated on the basis of the patient's psychophysical testing results.

A block diagram of the Interface Unit is shown in FIG. 22. The IU is a microprocessor based device with conventional structure. A processor 220 which is a Z80 in this embodiment but which could be any of a number of available processors, is the heart of the machine, and drives a Data Bus, Address Bus, and a number of control lines referred to as a Control Bus. System memory 221 comprises ROM and RAM, with necessary associated memory decoding and interfacing circuitry.

A system event clock 222 is used for timing of events such as presentation of stimuli, or time of erasure of the PROM. A parallel communications interface 224 comprising 16 input and 16 output lines 225, with associated handshaking lines, allows communication with the DPU. The rest of the circuitry is used to control the WSP.

The principal of control of the WSP is that the PROM in the WSP is disabled, and a SHADOW RAM 228 is made available to the encoder instead. This RAM appears to the WSP like the PROM, and is accessed through the Address, Data and Control Buses on the WSP from the Encoder mentioned in the previous section. However, this RAM may also be accessed by the IU processor, so that the IU can set up any programs or data in the shadow RAM, and thus control the operation of the WSP.

Bus arbitration logic 231 is used to arbitrate between the WSP or the IU processor for access to the shadow RAM. It is possible to disable the address bus on the Encoder by using the test signal selectors mentioned in the section on the encoder. The WSP data bus in input only to the Encoder. The bus arbitration logic thus disables the encoder address bus, and disables the WSP PROM to make the shadow RAM available to the IU processor, by enabling an address bus switch 230 and a data bus switch 229. At the same time, the Encoder itself is disabled to prevent generation of any stimulus frames which might contain spurious data and present unwanted stimuli to the patient.

The WSP uses the time varying data from the speech processor front end to map and encode electrode number and stimulus amplitude. When using the IU, it is necessary to be able to present stimuli which are also time varying. The way this is done is by use of an 8 bit latch 227 which is loaded from the IU processor. In normal operation of the encoder, when variable data is required, the ADC value is input to the address bus, and the output data appears on the data bus from the PROM. The mapping between the variable ADC address, and the output data to be sent to the implant, is fixed in the PROM.

Under control of the IU, the bus arbitration logic determines when an ADC read is to occur by decoding the WSP control lines. At this time, the WSP PROM, and the IU shadow RAM are disabled, and the 8 bit data latch is enabled to the data bus. Thus, the IU processor is able to update the data latch on a byte by byte basis to present variable data to the WSP encoder. In other words, the normal process of mapping variable ADC data from an address to data is bypassed. The IU is arranged so that the data in the data latch may be updated on a pulse burst by pulse burst basis, so that it is possible to send bursts with variable numbers of pulses to the implant, under control of the IU via the DPU.

The communications protocol between the DPU and the IU is designed in the form of transactions which include hardware handshaking (embedded in the circuit design) and software handshaking, to enhance the reliability of data communications. This is important to make sure that erroneous data received by the IU from the DPU as a result of a hardware fault or 'glitch' in the system will not cause improper stimuli to be delivered to the patient.

The normal stimulus protocol for patient testing is to use stimulus sequences where the amplitude of stimulus pulses delivered to the patient follows a trapezoidal waveform. In other words, starting from minimum possible stimulus, rising to the desired stimulus level in a known time and staying at that level for the required time, and then falling linearly to the minimum stimulus again. In order to present this shape of stimulus envelope, the IU processor must be able to update the data latch very rapidly, at the same time as performing other tasks such as communications with the host DPU computer. The software inside the IU is structured to facilitate this, in that all input and output of communications, and also variable data to the encoder, is done via ring buffers in the conventional manner, with output to the data latch awarded the highest priority.

In addition, the IU is able to generate the rising, falling and constant sections of the trapezoidal stimulus amplitude envelope with internal software in response to concise instructions from the DPU. This is an important feature as it allows the best economical use of the IU processor, without always tying up the DPU to calculate stimuli on a burst by burst basis. However, it is possible as well to present stimuli in any random fashion where all variable bursts may be set upon on a burst by burst basis from the DPU. This has an advantage in that hitherto unused or unthought of stimuli may be presented in the future if it is found to be useful for psychophysical testing or research.

Thus communication transactions between the DPU and IU are defined which include loading and reading the contents of the shadow RAM or WSP PROM; setting up stimuli with controllable time between stimuli, and definable contents of each burst in the frame; and various housekeeping functions such as PROM erasure, reset, and queue management.

The process of patient testing is to present stimuli on specified electrodes at known stimulus levels, and question the patient for a response. The stimulus presentation is under control of the DPU, from instructions typed in at the keyboard by the user (e.g., an audiologist). The software in the DPU has been carefully written to make it difficult to present stimuli to the patient which may be uncomfortably loud, although the levels able to be presented by the implant are insufficient to be physiologically damaging.

The patient may be asked to nominate thresholds, comfortable levels, and maximum comfortable levels on each or a subset of electrodes. Another test the patient may be asked to participate in is called pitch ranking, where the patient is asked to rank order psychophysically equally loud stimuli on different electrodes in order of pitch. This pitch ranking process is facilitated by the DPU software which generates random pairs of electrodes to be stimulated, to which the patient is required to nominate if the second is higher or lower in pitch than the first. When all possible pairs have been tested, a confusion matrix may be constructed, and the electrodes are then pitch ranked.

An additional test is called Loudness Scaling, where the patient is asked to assign loudness weights to different stimuli levels on an electrode (or electrodes), so that the relationship between stimulus current and psychophysical loudness perceptions may be developed.

Once the patient testing is complete, the data from the tests is used to generate a map or translation table from VF2 to electrode number, and from A2 to amplitude. This translation process is done by the software in the DPU. One of the powerful features of the system is the ability to use any mapping algorithm between acoustic signal parameters and stimulation parameters merely by altering the software in the DPU. Thus, as experience with cochlear implants accrues, and more psychophysics information is available, more stimulation strategies or mapping algorithms may be adopted to advantage. The mapping algorithms used in this embodiment are discussed in detail in a subsequent section.

The map so generated must be programmed into the PROM in the patient's WSP. Thus it is necessary to be able to erase and reprogram the PROM in the patient's WSP. One way of doing this would be to have the operator (e.g., audiologist) remove the PROM from the speech processor, erase using conventional erasing devices, and program the PROM using conventional programming equipment. However, it would be an obvious advantage if this error prone process could be avoided, and thus circuitry is included in the IU to enable erasing and reprogramming of the EPROM while still plugged into the WSP.

The ability to erase and reprogram the PROM without removing it from the WSP has the following advantages:

1. less error prone process, as unskilled people are not required to handle delicate electronic components;
2. more reliable construction possible, as the PROM may be permanently soldered into the circuit. In addition, it makes it possible to take advantage of newer packaging technologies (such as leadless chip carriers) which will allow a reduction in the size of the WSP;
3. more robust construction of the WSP, as the only externally accessible parts required are battery access and the connector for connection to the IU. A small window for exposure to ultraviolet light for PROM erasure may easily be incorporated in the WSP case; and 4. less internal volume required in the WSP as a PROM socket is not required.

MAPPING OF ACOUSTIC PARAMETERS TO STIMULATION PARAMETERS

One of the most powerful features of the system described in this disclosure is the ability to configure the system on a patient to patient basis. After implantation, the patient is tested with the DPU/IU system to measure the patient's psychophysical characteristics. These characteristics are used to generate a map between acoustic signal parameters and stimulation parameters, which is stored in an EPROM in the patient's own wearable speech processor. In essence, the psychophysical variables are separated from the acoustic variables, with the link being through the map.

In generating the map, two major parameters are of importance. These are the selection of electrode based on F2 frequency, or the way in which the electrodes are allocated portions of the frequency spectrum; and the way in which acoustic stimulus level (or acoustic loudness) is mapped into electrical stimulus level which results in perceptual loudness.

As mentioned above, advantage is taken of the tonotopic arrangement of electrodes spaced along the basilar membrane. Thus it should be the case that electrodes further from the round window (the apical electrodes) will elicit the lowest frequency percepts, and electrodes closest to the round window (the basal electrodes) will elicit the highest frequency percepts and the perceived frequency should increase in a monotonic function from low to high from apical to basal. In an ideal system, equally spaced electrodes should be allocated logarithmically equal portions of the acoustic spectrum of F2 range. Thus, for an F2 range from about 800 Hz to about 3kHz, each of the 22 electrodes used in this embodiment would have about a tenth of an octave allocated to it. The Output of the WSP front end produces an F2 signal which is a voltage linearly proportional to F2 frequency. In order to provide equal logarithmic frequency separations of electrodes, it is thus necessary to map the linear F2 signal logarithmically, and 8 bits of precision in the ADC is needed to do this.

However, the situation is complicated in real life, because it is sometimes necessary to allocate nonequal frequency portions to electrodes. For example, it may be found that a patient may not have all electrodes operating correctly, for example due to an absence of functioning nerve fibers in one part of the basilar membrane. Thus an equal logarithmic partitioning of the frequency spectrum would be inappropriate, and a different scheme would be necessary. The system described herein has the powerful feature that any arbitrary allocation of frequency bands to electrode (provided that bands are not overlapping) in the map, and the DPU allows this allocation to be made. Since the assignment of frequency bands to electrodes is done by merely placing the appropriate numbers into the EPROM in the WSP, this may be done according to a number of mapping algorithms.

The second facet of mapping is the scaling of acoustic loudness to stimulation current. This is a particularly complicated subject, particularly in this embodiment where the subject of acoustic to psychophysical mapping is obscured by the AGC and Squelch characteristics of the WSP front end, and the nonlinear circuits used in the WSP front end to generate the STAMP signal. The DPU/IU system can be used to present stimuli of various current level to the patient on selected electrodes to determine the threshold level (i.e., the lowest level at which stimulation is reliably perceived), and maximum comfortable loudness, which is the maximum stimulus level which the patient can tolerate for sustained periods. The problem then becomes one of mapping the acoustic signal range as represented by the STAMP signal into this stimulation range.

One way of generating this map is to present stimuli to the patient at all possible levels between threshold and maximum comfortable loudness, and ask the patient to scale the perceived loudness, e.g., on ab arbitrary scale between 1 and 100. This loudness scaling data may then be incorporated into the map so that acoustic loudness is correctly represented to the patient as perceived loudness. The software required in the DPU to perform this is quite straightforward.

However, the time required to perform these tests is great, as each electrode must have loudness scaling tests performed individually. We have found from measurements on a number of patients that it is adequate to model the loudness growth function between stimulus level and perceived loudness analytically, and use this to generate the map. Thus the loudness mapping between acoustic loudness, stimulus level, and perceived loudness can be generated sufficiently accurately by measurement only of threshold and comfortable levels.

Assume a function between perceived loudness, L, to the stimulus charge delivered, c. For constant width pulses (Phi 1 and Phi 2 equal, and constant), the charge delivered is related to stimulus current, i, and a power law is assumed, thus $L = k*i^x$ where k and x are constants, with x found to be in the order of 10. Thus $\log(L) = \log(k) + X*\log(i)$. The stimulus current i, and the number encoded into the stimulus amplitude burst length, C, are related by another power law. This power law is determined by the stimulator integrated circuit characteristics and choice of components, and is approximately $i = a*b^C$ and $a*b^C = 2$ mA approximately, when the number transmitted is 0, and a is a constant and b is the ratio of successive current steps, (about 0.97). Actually, the exponent should be not C but C-16 since the programmable current generator circuit requires 16 pulses to start up, but this factor is ignored for the moment, as it represents a constant to be added to the number to be stored in the map. Thus, $\log(i) = \log(a) + C*\log(b)$ The amplitude of the second formant, A, is related to the loudness of the acoustic second formant signal, L', by a power law $L' = d*A^{0.6}$ where d is a constant and the exponent, 0.6 has been determined experimentally and published, as will be known by those skilled in the art.

The speech processor must relate the current level C, to the measured amplitude, A. Thus a relationship between the loudness of the input signal, L', and the perceived loudness, L, must be proposed. The simplest one is $L' = L$, and could be used. This implies that the patient is being presented with a stimulus level which is an analogue of the speech amplitude at the AGC output, not the original speech signal.

Combining the above equations yields $$\log(L) = \text{Log}(k) + x^*(\log(a) + C^*\log(b))$$

$$= f + g \cdot C$$

where f and g are constants to be determined from the loudness scaling data on each particular patient. However, tests on a number of patients allow the constant f and g to be determined empirically, and are used with the threshold and maximum comfortable levels determined for each electrode to establish the mapping between acoustic level and stimulus amplitude.

The system as described herein has provision for only 31 loudness levels to be mapped into the range of stimulus levels between threshold and maximum comfortable loudness level. Experiments have shown that this should be adequate. However, the system is not limited to varying stimulus level by varying stimulus current alone, as it is also possible to change the amount of delivered charge in the stimulus by altering the durations of Phi 1 and Phi 2. Different scaling algorithms, or different speech processing strategies as may be discovered in the future could use this mechanism of varying stimulus level to achieve finer control. The design of the encoder chip allows any or all of the bursts to be sent to the receiver/stimulator to be variable, and thus different mapping or encoding strategies may be easily developed.

An additional part of the Diagnostic and Programming System not shown in the Figures is a means for acoustically monitoring the information output of the speech processor which is transmitted to the implantable receiver/stimulator. The purpose of such a device is as a troubleshooting aid, for when a patient reports a malfunction. The audiologist is able to apply the patient's own speech processor and coil to a simulator, and listen to an acoustic simulation of the stimulator output. In addition, in our embodiment, the simulator includes a display of which electrode is being stimulated for each stimulation frame. This feature allows a visual interpretation of the extent of use of each electrode, and may assist the audiologist in best configuring the pitch ranking of the map to make best use of the available electrodes in the acoustic environment.

In its simplest embodiment, such a simulator comprises a complete receiver/stimulator circuit as described in this invention. However, instead of the outputs of the receiver stimulator being connected to an electrode array, each output is connected via a light emitting diode to a dummy load such as a pair of headphones. Thus, when each stimulation pulse comes along, the active electrode will cause the LED associated with it to be illuminated for the duration of Phi 1 or Phi 2 (depending on polarity), and a sound pulse will be heard in the headphones, with the intensity of the sound proportional to the stimulation current.

Other embodiments have also been built which use conventional readily available integrated circuits to decode the data steam as defined in FIG. 8 to illuminate an indicator showing selected electrode, and to generate an auditory pulse whose amplitude is related to coded stimulus current amplitude. It is also possible to incorporate circuitry (such as a number of tuned filters) to generate a pulse burst at a frequency proportional to electrode selected to give an indication of frequency percept to be expected from the patient.

SAFETY FEATURES

Several features of the system combine to prevent painful or uncomfortable stimuli to the patient or incorrect stimuli, e.g., wrong electrode:

1. In terms of gross safety, because the system is powered externally through an inductive link, it is physically impossible to transmit enough power to electrocute the patient.
2. In terms of prevention of harmful stimuli, several factors play a part:

The amplitude pulse burst is coded so that more pulses equal lower amplitude. Thus there is an absolute maximum current which can be delivered, as set by the minimum width pulse burst, and any communication link errors (which usually result in extra pulses) will result in lower current.

The comfortable levels for each electrode for each patient are measured after implantation using the WSP, DPU and IU. This maximum level is then stored in the map in the WSP and thus it is not possible to encode stimulus current greater than the maximum comfortable level, no matter what acoustic input is received.

Because the same current source is used for Phi 1 and Phi 2, and the durations are (equal and) set by the program in the EPROM in the WSP, excellent charge symmetry is maintained. This is further improved by shorting all electrodes together when not stimulating. Thus, over long time scales, electrode corrosion will not be a problem.

3. The prevention of delivery of incorrect stimuli is achieved also with serveral means in addition to those mentioned above:

The information bursts which must communicate numbers (i.e., electrode select and mode select bursts) are encoded to be tolerant of the wrong number of pulses received.

The receiver stimulator has circuits to detect the power supply voltage, and delivery of stimulus is inhibited if insufficient voltage is available to provide voltage compliance for the current to be delivered.

The receiver/stimulator has circuits to detect the correct sequence of pulse bursts. If the correct sequence is not detected, then stimulation is inhibited.

Thus, it can be seen that there is a combination of factors which act to prevent harmful, incorrect, or unwanted stimuli.

The above description of embodiments of this invention is intended to be illustrative and not limiting. Other embodiments of this invention will be obvious to those skilled in the art in view of the above disclosure.

We claim:

1. In a cochlear implant system having a sound-to-electrical stimulation encoder means, a body-implantable receiver-stimulator and electrodes for receiving electrical signals from said encoder means, the improvement comprising means in said receiver-stimulator for preventing the delivery of a stimulation signal to the electrodes except after the receipt of a correct predetermined sequence of numerical information from said encoder means and means in said encoder means for encoding each item of numerical information as a number of pulses in a burst of pulses.

2. The cochlear implant system of claim 1 wherein the receiver-stimulator includes means for dividing the number of received pulses in each burst of pulses by an integer, thus decoding the numerical information transmitted.

3. The cochlear implant system of claim 1 including at least one cochlear electrode array and means for independently controlling the current amplitudes, burst rate, pulse separation and pulse widths of the stimulation signal to be delivered to said electrodes, said stimulation signal comprising pulses of an equal amplitude biphasic stimulus current waveform.

4. The cochlear implant system of claim 3 wherein each of said pulses of said waveform has equal pulse widths.

5. The cochlear implant system of claim 3 including one current source for determining the current during both phases of the biphasic stimulus current pulse.

6. The cochlear implant system of claim 3 including a single current source for providing stimulus signals for all electrodes.

7. In a cochlear implant system having a speech processor located external to a patient's body, said speech processor including sound-to-stimulation encoding means, a body-implantable receiver-stimulator and an electrode array implantable in the cochlea of a patient for receiving electrical signals from said encoding means, the improvement comprising
means for performing psychophysical testing on the auditory nervous system of the patient while said receiver-stimulator is receiving said electrical signals,
means, using the results of said testing, for preparing data in a map representing a patient stimulation strategy;
means for converting audio signal information to electrical signals in said sound-to-stimulation encoding means for that patient; and
means for erasably programming and storing said mapped data in said encoding means, such that stimulation parameters for speech signals are optimized utilizing said stored data to enhance the ability of the patient to recognize speech signals.

8. The cochlear implant system of claim 7 including patient operated controls in said testing means for determining stimulation thresholds and comfort levels.

9. The cochlear implant system of claim 7 in which said sound-to-stimulation encoding means includes memory means fixed in said encoding means for storing said mapped data in said encoding means.

10. The cochlear implant system of claim 9 in which said memory means is an erasable programmable read-only-memory.

11. The cochlear implant system of claim 7 in which said means for performing psychophysical testing include means for stimulation, display, and storage of the results of said testing to provide a plurality of electrical stimulation inputs to the auditory nervous system of a patient.

12. The cochlear implant system of claim 7 in which psychophysical testing means includes means for determining the mapping between acoustic parameters and stimulation parameters, and means for testing the mapping before incorporating the mapping into the patient's stimulation encoding means.

13. A multichannel cochlear prosthesis system for use with a patient comprising:
a multichannel electrode array suitable for implantation in the ear of a person;
a multichannel stimulator connected to said electrode array, said stimulator being suitable for implantation in said person and being used to provide electrical signals to stimulate said electrode array;
means for encoding sound an electrical stimulation signal, said means for encoding being suitable to be worn externally by said person;
means for transmitting encoded electrical signals representative of speech stimulation parameters from said means for encoding to said multichannel stimulator;
means, external to the patient, for testing the patient's psychophysical responses to stimulation of the patient's auditory nerves by selected electrical signals applied to said electrode array by said multichannel stimulator through the means for encoding;
means for mapping the psychophysical responses in the form of data of the patient to stimulation of the patient's auditory nerves by said selected electrical signals applied to said electrode array by said multichannel stimulator through said means for encoding to optimize the ability of the patient to perceive certain sounds; and
means for storing data from the results of said responses in said means for encoding to encode said data, said results being utilized to determine a relationship between auditory input and said electrical stimulation parameters to optimize the ability of the patient to perceive sounds.

14. The system of claim 13 in which said electrode array comprises series of spaced platinum rings insulated from each other and fixed on a flexible strip carrier of tapering diameter.

15. The system of claim 13 including means in said stimulator for providing a leakage current to electrodes not selected for stimulation of less than 10 microamps.

16. The system of claim 13 in which said electrodes are stimulated with a biphasic constant current thereby to provide zero D.C. current to the electrodes and substantially prevent corrosion problems.

17. The system of claim 13 including selection means for selecting bipolar stimulation of any pair of said electrodes in said array.

18. The system of claim 17 in which said selection means is contained in said encoding means.

19. The prosthesis system of claim 13 wherein said means for mapping includes means for assigning bands of frequency to selected electrodes in said electrode array.

20. The prosthesis system of claim 13 wherein said means for mapping includes means for scaling acoustic loudness perceived by the patient.

21. A prosthesis comprising
a multi-electrode array for transmitting electrical stimulations to a patient's auditory nerves and adapted to be implantable in a patient,
a patient implantable stimulator means for detecting externally transmitted electrical signals identifying one or more electrodes in said array to act as a source or sink of stimulation current to selected electrodes;
current switching means including a controllable current sink in said stimulator means operable by external signals detected by said stimulator means; and a power supply in said implantable stimulator means, said power supply being chargeable by an externally generated power supply signal to connect at least two of any of said electrodes variously to said power supply or said current sink.

22. The prosthesis of claim 20 including means to switch the connections in said current switching means so as to supply biphasic signals of opposite polarity to said electrodes.

23. The prosthesis of claim 20 in which the electrode array is implanted in a patient's ear and the electrical signals are indicative of auditory information.

24. The prosthesis of claim 20 including means to connect two electrodes to the current sink and all other electrodes to said power supply.

25. A multichannel cochlear prosthesis system comprising:

a patient implantable tissue stimulating multichannel electrode array;

a patient implantable multichannel stimulator connected to said array;

a patient externally worn sound-to-electrical signal stimulation encoding means, said encoding means including memory means programmable after implantation of said electrode array and said stimulator in a patient;

means for programming said memory means based on the patient's auditory perceptions in response to various electrical stimulating pulse signals;

means for transmitting electrical stimulation signals representing speech parameters from said encoding means to said stimulator and to said array for stimulating tissue in accord with said programmed perspections; and means for controlling said stimulator by said encoding means, such control including varieties of at least one or more of pulse rate, pulse amplitude, pulse duration interval between phases of a biphasic current pulse, and selection of which two of any electrodes stimulus current is to be applied.

26. The system of claim 25 wherein the selection of which electrodes in said electrode array are to be used for stimulation is done in the external sound-to-stimulation encoding means.

27. The system of claim 25 wherein said memory means is a programmable read-only-memory.

28. The system of claim 25 wherein said memory means is an erasable programmable read-only-memory.

29. The system of claim 28 further including means for erasing and reprogramming said memory while it is plugged into said encoding means.

30. The system of claim 25 including means in said encoding means for preventing the delivery of uncomfortable stimuli to the patient.

31. The system of claim 31 wherein said means for preventing delivery of uncomfortable stimuli comprises a data map stored in said encoding means wherein the maximum allowable electrical stimulus to the patient capable of being generated by the data in said data map is beneath the level which causes discomfort.

32. The system of claim 31 wherein said means for preventing delivery of uncomfortable stimuli comprises means for providing a common current source for biphasic current stimulation of equal duration and amplitude.

33. The system of claim 25 wherein said means for programming said memory means includes means for separably attaching said means for programming to said encoding means when it is desired to program the memory means based on the patient's perceptions.

34. The system of claim 33 further including acoustic simulation means in said programming means for monitoring the stimulus signals delivered to the implanted stimulator.

35. The system of claim 25 wherein said means to input the memory means includes means to select subsets of up to all of the electrodes in said array to be used for stimulation in response to a given auditory input signal.

36. The system of claim 25 including means for selecting the order of pitch ranking of the electrodes in the array and for programming the encoding means in response to the patient's selections of such ranking.

37. The system of claim 25 including means for simultaneous independent selection of particular electrodes for stimulation, the stimulation rate and stimulation amplitude for each stimulation.

38. The system of claim 25 further including means for displaying continuously a visual indication of the electrode selected by the transmitted data from the sound-to-stimulation encoding means for the purpose of monitoring.

39. The system of claim 25 further including means, in the sound-to-stimulation encoding means, for generating information in the form of a known and unvarying train of stimulus pulses from the implantable stimulator and for conducting said pulses to selected electrodes to verify operation of the system.

40. The system of claim 25 in which said means for controlling the stimulator by said encoding means includes means for transmitting and separate means for receiving both power and data representing said pulse signals, said means for receiving power and data including a receiver coil means, said coil means being tunable.

41. The system of claim 40 in which said receiver coil means is coupled via a transformer to a power and data circuit in said stimulator.

42. The system of claim 25 including means in said encoding means for permitting selection of various stimulation strategies.

43. The system of claim 42 wherein said means in said encoding means for permitting selection of various stimulation strategies includes means for encoding the frequency of a second format of an acoustic signal into electrode selection, means for encoding a voicing frequency of said signal into stimulation rate and means for encoding the amplitude of the second formant into stimulation amplitude, each of said encodations being made in said encoding means.

44. The system of claim 42 wherein said means for selection of stimulation strategies includes means for encoding frequency of a second formant of an acoustic signal into electrode selection, means for encoding frequency of a first formant of said signal into stimulation rate and means for encoding the amplitude of the acoustic signal into stimulation amplitude.

45. The system of claim 40 or 41 wherein said means for loading said memory means includes means for choosing an optimal speech processing strategy.

46. The system of claim 25 including means in said encoding means for generating a signal to deactivate the encoding means during periods of relatively constant amplitude acoustic signal.

47. The system of claim 25 including means for configuring the program in said memory means for different patient psychophysical variables.

48. The system of claim 25 including means for preventing operation of said encoding means when an inadequate power supply voltage is present so as to prevent spurious pulses being transmitted to said stimulator.

49. The system of claim 25 including means for preventing delivery of stimuli by the stimulator to the electrode array when a power supply voltage to said stimulator is insufficient to give required voltage compliance to said electrode array.

50. The system of claim 25 including means for programming the memory means while the memory means is connected to said encoding means.

51. The system of claim 31 including pulse burst forming means in said encoding means and means for controlling said pulse burst forming means, said means for controlling including said memory means, said memory means being indicative of the patient auditory perceptions in response to electric stimuli perceived.

52. The system of claim 51 in which said encoding means and said implantable stimulator comprise integrated circuits, the circuit of said encoding means being programmed to produce sequences of constant frequency pulses with the number of pulses and time between pulse bursts being determined by either of said control means.

53. The cochlear system of claim 52 further comprising means for keeping said circuit in a powered state between said data sequences.

54. The system of claim 51 wherein said pulse bursts are formatted in successive frames of data bursts, each frame comprising a reset start burst, an active electrode select burst, an electrode configuration mode burst, an amplitude burst, and two bursts for the two phases of stimulation pulses, and means to provide a time interval between each of said bursts within each said frame.

55. The system of claim 54 including means to utilize the top 10 to 20 dB of the current acoustic stimulus level to determine stimulus amplitude for said amplitude burst.

56. The system of claim 54 further including means to minimize energy consumption by said stimulator to allow said stimulator to be in an active state when subsequent stimulus data frames are transmitted, so as to eliminate the need for a start power pulse in every stimulation frame.

57. The system of claim 51 including a frame of data bursts including two phase simulation bursts of constant time duration.

58. The system of claim 51 further including means in said encoding means for determining amplitude of output current from said stimulator by duration of the pulse burst to control stimulus amplitude and means for reducing said stimulus amplitude by increasing duration of said pulse burst.

59. The system of claim 25 wherein said stimulator comprises a digital circuit including an error detection circuit to generate signals to a state counter, means for resetting said counter, said state counter being incremented through frame sequences of data bursts from said encoding means by a signal asserted at the end of every data burst other than reset.

60. The system of claim 25 wherein said means for programming said memory means includes means for tailoring each patient's perceptions and means for programming said memory means to reflect said perceptions.

61. The system of claim 60 further including means in said sound to-stimulation encoding means for selecting a subset of from one to all of said electrodes for stimulation.

62. The system of claim 25 further including means for providing a monotonic substantially exponentially decreasing relationship between a coded current amplitude of a stimulus to said electrodes and the actual current delivered to said electrodes.

63. The system of claim 62 including means for limiting the maximum current to be delivered to said electrodes.

64. The cochlear system of claim 25 further including means for conveying environmental sounds to the patient.

65. The cochlear system of claim 25 further including means in said encoding means for disabling the generation of speech stimulation signals during a delay period of constant background noise.

66. The cochlear system of claim 65 further including means permitting environmental impulsive, non-speech sounds to enter said encoding means when said encoding means is disabled from receiving speech sounds.

67. A speech processor encoding means for a cochlear prosthesis having electrodes for electrical stimulation of auditory nerves comprising
a memory means,
means for generating a data format, indicative of a patient's auditory perceptions of sound into said memory means;
means for generating from said data format into a map of electrode stimulation parameters to optimize the patient's ability to hear sounds; and
means for programming said resultant map of said parameters into said memory means.

68. The invention of claim 67 including means for preventing burst sequences to said receiver-stimulator of an uncomfortable perception to the patient.

* * * * *

UNITED STATES PATENT AND TRADEMARK OFFICE
CERTIFICATE OF CORRECTION

PATENT NO. : 4,532,930           Page 1 of 3

DATED : August 6, 1985

INVENTOR(S) : Peter A. Crosby et al.

It is certified that error appears in the above—identified patent and that said Letters Patent is hereby corrected as shown below:

In the abstract, line 20, change "Biphastic" to --Biphasic--.

Col. 1, line 37, change "air" to --aid--.

Col. 5, line 34, change "considerably" to --considerable--.

Col. 9, line 7, change "it" to --is--.

Col. 9, line 36, change "signals" to --signal--.

Col. 11, line 43, change "mo-" to --mi---.

Col. 19, line 46, change "IX" to --1X--.

Col. 22, line 62, change "Vthlp" to --Vth1p--.

Col. 22, line 64, change "Klp" to --K1p--; and "Vthlp" to --Vth1p--.

Col. 22, line 66, change "Klp" to --K1p--.

Col. 23, line 4, change Vthlp" to --Vth1p--.

Col. 23, line 6, change "Klp" to --K1p--.

Col. 23, line 11, change Klpl" to --K1p1--.

Col. 23, line 19, change Klpl" to --K1p1--.

Col. 23, line 46, "while with B closed" should not be italicize(

Col. 25, line 58, change "show" to --shows--.

UNITED STATES PATENT AND TRADEMARK OFFICE
CERTIFICATE OF CORRECTION

PATENT NO. : 4,532,930          Page 2 of 3

DATED : August 6, 1985

INVENTOR(S) : Peter A. Crosby et al.

It is certified that error appears in the above—identified patent and that said Letters Patent is hereby corrected as shown below:

Col. 27, line 41, change "generatin" to --generation--.

Col. 28, line 30, change "coventinal" to --conventional--.

Col. 28, line 32, change "functins" to --functions--.

Col. 36, line 56, after "instruction" insert a period.

Col. 41, line 53, change "bursts" to --burst--.

Col. 48, line 14, change "ab" to --an--.

Col. 48, line 38, change "+X*log(i)" to --+x*log(i)--.

Col. 53, line 36, change "spections;" to --ceptions;--.

Col. 56, line 17, change "sound to-stimulation" to --sound-to-stimulation--.

UNITED STATES PATENT AND TRADEMARK OFFICE
CERTIFICATE OF CORRECTION

PATENT NO. : 4,532,930

DATED : August 6, 1985

INVENTOR(S) : Peter A. Crosby et al.

It is certified that error appears in the above-identified patent and that said Letters Patent is hereby corrected as shown below:

```
Claims 22,23,24, line 1, change "20" to --21.
Claims 31 and 32, line 1, change "31" to --30--.
Claim 45, line 1, change "40 or 41" to --36 or 37--.
Claim 51, line 1, change "31" to --25--.
```

Signed and Sealed this

Eleventh Day of March 1986

[SEAL]

Attest:

DONALD J. QUIGG

Attesting Officer

Commissioner of Patents and Trademarks